(12) United States Patent
Yamada et al.

(10) Patent No.: US 8,501,706 B2
(45) Date of Patent: *Aug. 6, 2013

(54) DUPLEX OLIGONUCLEOTIDE COMPLEXES AND METHODS FOR GENE SILENCING BY RNA INTERFERENCE

(75) Inventors: Christina Yamada, Boulder, CO (US); Anastasia Khvorova, Northborough, MA (US); Rob Kaiser, Broomfield, CO (US); Emily Anderson, Lafayette, CO (US); Devin Leake, Denver, CO (US)

(73) Assignee: Dharmacon, Inc., Lafayette, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,709

(22) Filed: Jul. 19, 2012

(65) Prior Publication Data

US 2012/0322855 A1    Dec. 20, 2012

Related U.S. Application Data

(62) Division of application No. 11/858,829, filed on Sep. 20, 2007, now Pat. No. 8,252,755.

(60) Provisional application No. 60/826,702, filed on Sep. 22, 2006, provisional application No. 60/867,706, filed on Nov. 29, 2006.

(51) Int. Cl.
*C12N 15/11* (2006.01)

(52) U.S. Cl.
USPC .......................................................... 514/44 A

(58) Field of Classification Search
None
See application file for complete search history.

(56) References Cited

U.S. PATENT DOCUMENTS

| 8,188,060 | B2 | 5/2012 | Khovorva et al. | |
|---|---|---|---|---|
| 8,252,755 | B2 | 8/2012 | Yamada et al. | |
| 8,273,722 | B2 | 9/2012 | Ladine et al. | |
| 2004/0192626 | A1* | 9/2004 | McSwiggen et al. | 514/44 |
| 2005/0197315 | A1* | 9/2005 | Taira et al. | 514/44 |
| 2012/0259001 | A1 | 10/2012 | Khovorva et al. | |

* cited by examiner

*Primary Examiner* — Jennifer Pitrak McDonald
(74) *Attorney, Agent, or Firm* — Dorf & Nelson LLP; Scott D. Locke, Esq.

(57) ABSTRACT

Provided herein are duplex oligonucleotide complexes which can be administered to a cell, tissue or organism to silence a target gene without the aid of a transfection reagent(s). The duplex oligonucleotide complexes of the disclosure include a conjugate moiety that facilitates delivery to a cell, tissue or organism.

18 Claims, 44 Drawing Sheets

| Sense | | Antisense | |
|---|---|---|---|
| 1 | Unmod | 1 | Unmod, 3'PO Overhang, 5'P |
| 2 | 2'OMe C, 2'OMe U, 1st 2 bases - 2'OMe - no overhangs | 2 | 2'F C, 2'F U, PS on 3' PS Overhang |
| 3 | 2'OMe C, 2'OMe U, 1st 2 bases - 2'OMe | 3 | Unmod, blunt - 5'P |
| 4 | 2'OMe C, 2'OMe U, 1st 2 bases - 2'OMe | 4 | Unmod, 3'PS Overhang, 5'P |
| 5 | 2'OMe C, 2'OMe U, 1st 2 bases - 2'OMe | 5 | Unmod, 3'PO Overhang, 5'P |
| 6 | 2'OMe C, 2'OMe U, 1st 2 bases - 2'OMe | 6 | Unmod, 2'OMe 2nd pos from 5', 3'PS, 5'P |
| 7 | 2'OMe C, 2'OMe U, 1st 2 bases - 2'OMe | 7 | Unmod, 2'OMe 2nd pos from 5', 3'PO, 5'P |

DUPLEX OLIGONUCLEOTIDE COMPLEXES AND METHODS FOR GENE SILENCING BY RNA INTERFERENCE

CROSS-REFERENCE TO RELATED APPLICATIONS

This application is a divisional of U.S. Ser. No. 11/858,829, filed Sep. 20, 2007, which claims the benefit of U.S. Provisional Application Ser. Nos. 60/826,702, filed Sep. 22, 2006, and 60/867,706 filed Nov. 29, 2006, the disclosure of each of the aforementioned applications is herein incorporated by reference in its entirety.

FIELD OF THE INVENTION

The present disclosure relates to the field of gene silencing using modified polynucleotides. Specifically, the disclosure provides duplex oligonucleotide complexes that include a conjugate moiety which facilitates delivery of the oligonucleotides into a cell, tissue or organism and methods of making and using them to silence a target gene.

SEQUENCE LISTING

The present specification incorporates herein by reference the sequence listing provided electronically in the file entitled "Sequence Listing g4US_ST25.txt", created Sep. 19, 2007 which is 9,885 bytes in size.

BACKGROUND OF THE DISCLOSURE

RNA interference (RNAi) is a near-ubiquitous post-transcriptional gene regulatory mechanism that is mediated by microRNAs (miRNAs). Gene knockdown by these small, non-coding RNAs exploits the RNA Induced Silencing Complex (RISC) which utilizes the seed region (positions 2-7) of the miRNA guide strand to target the 3'UTR of mRNA for transcript cleavage and/or translational attenuation. Since the discovery that short, synthetic dsRNAs (referred to as small interfering RNAs, siRNAs) can enter the pathway, RNAi has been adopted as a tool for functional genomics.

SUMMARY

In one aspect, the present disclosure provides a duplex oligonucleotide complex comprising:

a. a sense strand that ranges in size from about 18 to about 30 nucleotides;

b. an antisense strand that ranges in size from about 18 to about 30 nucleotides, wherein the antisense strand has significant levels of complementarity to both the sense strand and a target gene, and wherein the sense strand and the antisense strand form a duplex;

c. a conjugate moiety that facilitates cellular delivery; and d. a linker molecule that is from about 3 to about 9 atoms in length and attaches the conjugate moiety to the sense strand.

Between about 40% to about 90% of the nucleotides of the sense strand and between about 40% to about 90% of the nucleotides of the antisense strand are chemically modified nucleotides.

In one embodiment, the duplex oligonucleotide complex comprises a mismatch between nucleotide 10, 11, 12, 13, or 14 on the antisense strand and the opposite nucleotide on the sense strand, preferably a mismatch between nucleotide 14 on the antisense strand and the opposite nucleotide on the sense strand.

In another embodiment, each chemically modified nucleotide in the duplex oligonucleotide complex is selected from the group consisting of 2' F modified nucleotides and 2'-O-methyl modified nucleotides. Preferably, nucleotides 1 and 2 and all C nucleotides and all U nucleotides on the sense strand are 2' O-methyl modified and all C nucleotides and all U nucleotides on the antisense strand are 2' F modified.

In another embodiment, the conjugate moiety is selected from the group consisting of cholesterol, cholestanol, stigmasterol, cholanic acid, and ergosterol.

In another embodiment, the linker molecule is 5 to 8 atoms in length.

In another embodiment, the duplex oligonucleotide complex also comprises at least one dye molecule attached to the 5' end of the sense strand.

In another embodiment, the linker molecule attaches the conjugate moiety to the 3' end of the sense strand.

In another embodiment, the conjugate moiety is cholesterol, the linker molecule is 8 atoms in length, and the linker molecule attaches the cholesterol to the 3' end of the sense strand such that the sense strand of the duplex oligonucleotide complex can have the structure:

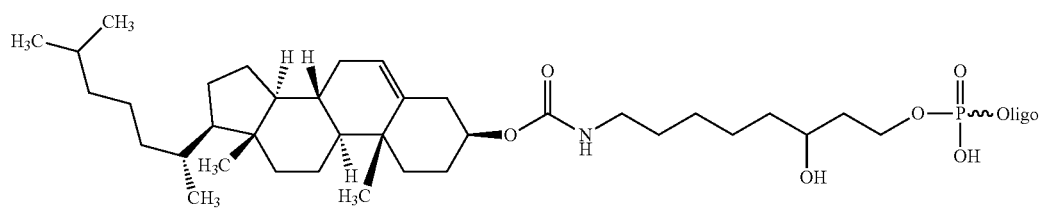

In another embodiment, the conjugate moiety is cholesterol, the linker molecule is 5 atoms in length, and the linker molecule attaches the cholesterol to the 3' end of the sense strand such that the sense strand of the duplex oligonucleotide complex can have the structure:

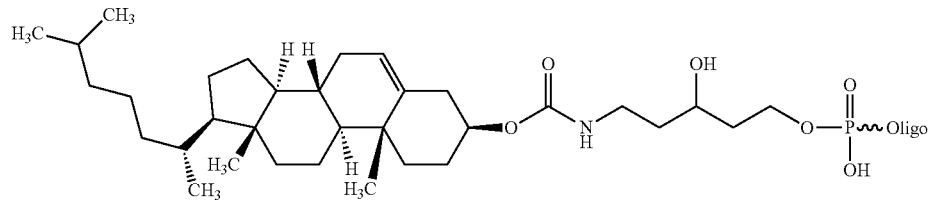

Preferably, in this embodiment nucleotides 1 and 2 and all C nucleotides and all U nucleotides on the sense strand are 2' O-methyl modified and all C nucleotides and all U nucleotides on the antisense strand are 2' F modified. In addition, the duplex oligonucleotide complex of this embodiment may comprise a phosphate at the 5' end of the antisense strand. The sense strand in this embodiment is preferably between about 19 nucleotides and about 23 nucleotides in length and the antisense strand is between about 19 nucleotides and about 23 nucleotides in length. The duplex oligonucleotide complex of this embodiment preferably includes a mismatch between nucleotide 10, 11, 12, 13, or 14 on the antisense strand and the opposite nucleotide on the sense strand, more preferably between nucleotide 14 on the antisense strand and the opposite nucleotide on the sense strand. The duplex oligonucleotide complex of this embodiment may also comprise an overhang at the 3' end of the antisense strand which overhang comprises phosphorothioate linkages.

In another aspect, the disclosure provides a duplex oligonucleotide complex comprising:
  a. a sense strand that ranges in size from about 18 to about 30 nucleotides;
  b. an antisense strand that ranges in size from about 18 to about 30 nucleotides, wherein the antisense strand has significant levels of complementarity to both the sense strand and a target gene and wherein the sense strand and the antisense strand form a duplex;
  c. a cholesterol molecule attached to the 3' end of the sense strand via a C5 linker molecule wherein the cholesterol-linker-sense strand has the structure:

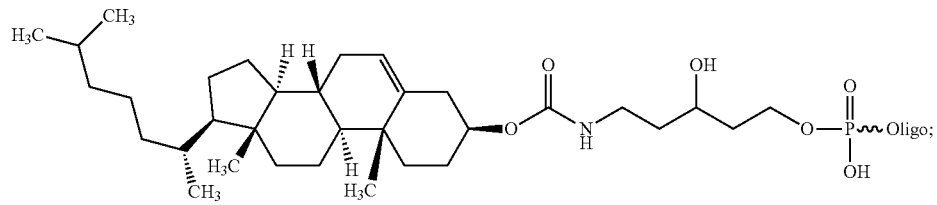

and
  d. a phosphate group at the 5' end of the antisense strand.

Between about 40% to about 90% of the nucleotides of the sense strand and between about 40% to about 90% of the nucleotides of the antisense strand are chemically modified nucleotides. Preferably, on the sense strand, nucleotides 1 and 2 and all C nucleotides and all U nucleotides are 2'O-methyl modified; and wherein on the antisense strand, all C nucleotides and all U nucleotides are 2' F modified. Preferably, a mismatch exists between nucleotide 10, 11, 12, 13, or 14 on the antisense strand and the opposite nucleotide on the sense strand, more preferably between nucleotide 14 on the antisense strand and the opposite nucleotide on the sense strand. Preferably, the duplex oligonucleotide complex also comprises a 2 nucleotide overhang at the 3' end of the antisense strand comprising phosphorothioate linkages.

In another aspect, the disclosure provides a method for inhibiting expression of a target gene in a cell. The method involves delivering to the cell the duplex oligonucleotide complex of any of the preceeding embodiments. In one embodiment, the duplex oligonucleotide complex is delivered to the cell by reverse transfection. In another embodiment, the duplex oligonucleotide complex is delivered to the cell in vivo.

In another aspect, the disclosure provides a pharmaceutical composition comprising a duplex oligonucleotide complex according to any of the preceeding embodiments, and further comprising at least one pharmaceutically acceptable carrier or diluent.

In another aspect, the disclosure provides a kit comprising a container. The container includes a duplex oligonucleotide complex according to any of the preceeding embodiments and further comprises a reduced serum tissue culture medium.

Further aspects and embodiments will be apparent upon reading the disclosure.

BRIEF DESCRIPTION OF THE FIGURES

The preferred embodiments of the present disclosure have been chosen for purposes of illustration and description but are not intended to restrict the scope of the disclosure in any way. The benefits of the preferred embodiments of certain aspects of the disclosure are shown in the accompanying figures, wherein:

FIG. 22 shows the relative levels of expression of each gene (e.g. mouse or human) following G4 siRNA knockdown by individual or pools of targeting duplexes. Y axis represent fraction of target gene expressed. X axis references genes being targeted with individual G4 siRNAs. "F75" represents 75% knockdown.

DETAILED DESCRIPTION OF THE DISCLOSURE

Figure 1:
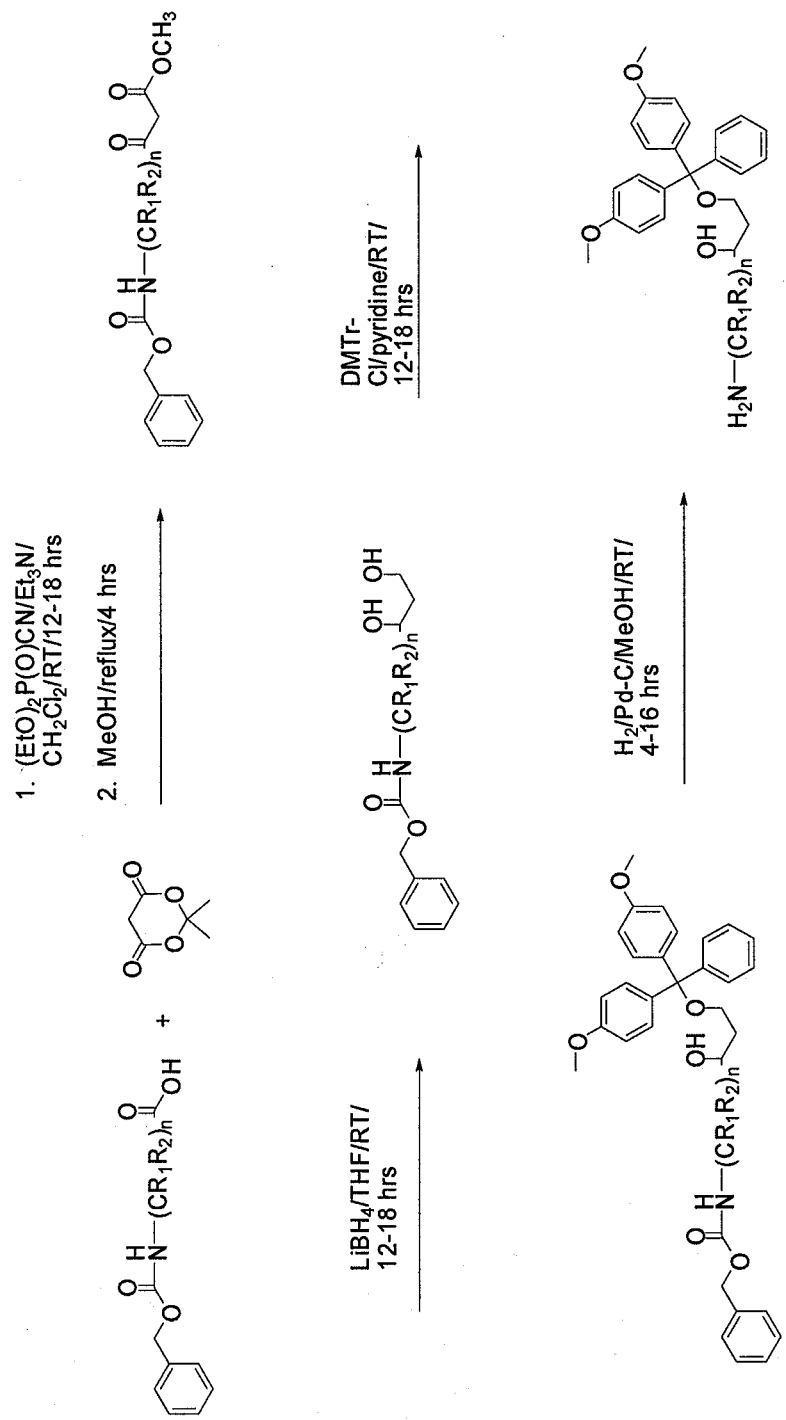
FIG. 1 shows a generalized synthesis scheme for the preparation of an ω-amino-1,3-diol linker compound.

The present disclosure will now be described in connection with preferred embodiments. These embodiments are presented to aid in an understanding of the present disclosure and are not intended, and should not be construed, to limit the disclosure in any way. All alternatives, modifications and equivalents that may become apparent to those of ordinary skill upon reading this disclosure are included within the spirit and scope of the present disclosure.

This disclosure is not a primer on compositions and methods for performing RNA interference. The present disclosure is directed to compositions and methods for performing RNA interference, including siRNA and miRNA-induced gene silencing, miRNA inhibition, and more. Through the use of the present disclosure, modified polynucleotides, and derivatives thereof, one may improve the efficiency of RNA interference applications.

In general the terms and phrases used herein have art-recognized meanings, which can be found by reference to standard texts, journal references and contexts known to those skilled in the art. The following definitions are provided to clarify their specific use in the context of the disclosure.

The term "alkyl" refers to a hydrocarbyl moiety that can be saturated or unsaturated, and substituted or unsubstituted. It may comprise moieties that are linear, branched, cyclic and/or or heterocyclic, and contain functional groups such as ethers, ketones, aldehydes, carboxylates, etc.

Exemplary alkyl groups include but are not limited to substituted and unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and alkyl groups of higher number of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, and 2-ethylhexyl. The term alkyl also encompasses alkenyl groups, such as vinyl, allyl, aralkyl and alkynyl groups. Unless otherwise specified, alkyl groups are not substituted.

Substitutions within alkyl groups, when specified as present, can include any atom or group that can be tolerated in the alkyl moiety, including but not limited to halogens, sulfurs, thiols, thioethers, thioesters, amines (primary, secondary, or tertiary), amides, ethers, esters, alcohols and oxygen. The substitutions within alkyl groups can by way of example also comprise modifications such as azo groups, keto groups, aldehyde groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Unless otherwise specified, alkyl groups do not comprise halogens, sulfurs, thiols, thioethers, thioesters, amines, amides, ethers, esters, alcohols, oxygen, or the modifications listed above.

Further, alkyl groups may also contain hetero substitutions, which are substitutions of carbon atoms, by for example, nitrogen, oxygen or sulfur. Heterocyclic substitutions refer to alkyl rings having one or more heteroatoms. Examples of heterocyclic moieties include but are not limited to morpholino, imidazole, and pyrrolidino. Unless otherwise specified, alkyl groups do not contain hetero substitutions or alkyl rings with one or more heteroatoms (i.e., heterocyclic substitutions).

The preferred alkyl group for a 2' modification is a methyl group with an O-linkage to the 2' carbon of a ribosyl moiety, i.e., a 2'-O-alkyl that comprises a 2'-O-methyl group.

The phrase "2'-O-alkyl modified nucleotide" refers to a nucleotide unit having a sugar moiety, for example a deoxyribosyl moiety that is modified at the 2' position such that an oxygen atom is attached both to the carbon atom located at the 2' position of the sugar and to an alkyl group. In various embodiments, the alkyl moiety consists essentially of carbons and hydrogens. A particularly preferred embodiment is one wherein the alkyl moiety is methyl.

The phrase "antisense strand" as used herein, sometimes abbreviated to "AS", refers to a polynucleotide or region of a polynucleotide that is substantially (i.e., 80% or more) or 100% complementary to a target nucleic acid of interest. An antisense strand may be comprised of a polynucleotide region that is RNA, DNA or chimeric RNA/DNA. For example, an antisense strand may be complementary, in whole or in part, to a molecule of messenger RNA, an RNA sequence that is not mRNA (e.g., tRNA, rRNA and hnRNA) or a sequence of DNA that is either coding or non-coding. The phrase "antisense strand" includes the antisense region of the polynucleotides that are formed from two separate strands, as well as unimolecular siRNAs that are capable of forming hairpin structures. The phrases "antisense strand" and "antisense region" are intended to be equivalent and are used interchangeably. The antisense strand can be modified with a diverse group of small molecules and/or conjugates.

The phrase "2' carbon modification" refers to a nucleotide unit having a sugar moiety that is modified at the 2' position of the sugar subunit. A "2'-O-alkyl modified nucleotide" is modified at this position such that an oxygen atom is attached both to the carbon atom located at the 2' position of the sugar and to an alkyl group, e.g., 2'-O-methyl, 2'-O-ethyl, 2'-O-propyl, 2'-β-isopropyl, 2'-O-butyl, 2-O-isobutyl, 2'-O-ethyl-O-methyl ($—OCH_2CH_2OCH_3$), and 2'-O-ethyl-OH($—OCH_2CH_2OH$). A "2' carbon sense modification" refers to a modification at the 2' carbon position of a nucleotide on the sense strand or within a sense region of polynucleotide. A "2' carbon antisense modification" refers to a modification at the 2' carbon position of a nucleotide on the antisense strand or within an antisense region of polynucleotide.

The term "complementary" refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G), or in any other manner that allows for the formation of stable duplexes.

Perfect complementarity or 100% complementarity refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other. For example, for two 20-mers, if only two base pairs on each strand can hydrogen bond with each other, the polynucleotide strands or regions exhibit 10% complementarity. In the same example, if 18 base pairs on each strand or each region can hydrogen bond with each other, the polynucleotide strands exhibit 90% complementarity. Substantial complementarity refers to polynucleotide strands or regions exhibiting 80% or greater complementarity.

The term "duplex" refers to a region of double-stranded structure formed by two antiparallel polynucleotide strands as a result of base-pairing between the strands. A duplex may be formed between two separate polynucleotides, or the strands may be contained with a single polynucleotide sequence e.g. a hairpin structure where the "loop" portion of the hairpin allows the two strands to adopt an antiparallel configuration relative to each other. A duplex structure may be interrupted by, e.g., mismatches and loops. For example, where two antiparallel strands are the same length but are not 100% complementary in sequence, duplex regions will be interrupted by regions where base-pairing does not occur due to the presence of mismatches.

The term "deoxynucleotide" refers to a nucleotide or polynucleotide lacking an OH group at the 2' or 3' position of a sugar moiety with appropriate bonding and/or 2',3' terminal dideoxy, instead having a hydrogen bonded to the 2' and/or 3' carbon.

The terms "deoxyribonucleotide" and "DNA" refer to a nucleotide or polynucleotide comprising at least one ribosyl moiety that has an H at its 2' position of a ribosyl moiety instead of an OH.

The term "gene" is defined to include both transcribed and non-transcribed elements. Thus, for instance, a gene can include any non-transcribed enhancer and/or promoter (i.e. genomic DNA) that plays a role in determining the level, timing, or tissue specificity of expression of a particular mRNA transcript or non-coding RNA. In addition, the 5' UTR, ORF, 3' UTR, introns, as well as non-coding RNAs such as miRNAs, piRNAs, tRNAs, rRNAs, and more, are included as elements of a gene.

The term "lipid-independent delivery reagent" refers to any number of molecules that can be conjugated to e.g.

nucleic acids to enhance delivery in the absence of art-recognized nucleic acid delivery reagents (e.g. Lipofectamine, Lipofectamine 2000, DharmaFECTs). Such conjugates can themselves be lipid in nature, or consist of proteins, carbohydrates, or more.

The term "mismatch" includes a situation in where Watson-Crick base pairing does not take place between a nucleotide of a sense strand and a nucleotide of an antisense strand. An example of a mismatch would be an A across from a G, a C across from an A, a U across from a C, an A across from an A, a G across from a G, a C across from a C, and so on. Mismatches are also meant to include an abasic residue across from a nucleotide or modified nucleotide, an acyclic residue across from a nucleotide or modified nucleotide, a gap, or an unpaired loop. In its broadest sense, a mismatch as used herein includes any alteration at a given position which decreases the thermodynamic stability at or in the vicinity of the position where the alteration appears, such that the thermodynamic stability of the duplex at the particular position is less than the thermodynamic stability of a Watson-Crick base pair at that position. Preferred mismatches include a G across from an A, and an A across from a C. A particularly preferred mismatch comprises an A across from an A, G across from a G, C across from a C, and U across from a U.

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Preferably, a "nucleotide" comprises a cytosine, uracil, thymine, adenine, or guanine moiety.

Nucleotide analogs include chemically modified nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety as defined herein. Nucleotide analogs are also meant to include nucleotides with bases such as inosine, queuosine, xanthine, sugars such as 2'-methyl ribose, non-natural phosphodiester internucleotide linkages such as methylphosphonates, phosphorothioates and peptides.

Modified bases refer to nucleotide bases such as, for example, adenine, guanine, cytosine, thymine, and uracil, xanthine, inosine, and queuosine that have been modified by the replacement or addition of one or more atoms or groups. Some Examples of types of modifications that can comprise nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine.

Further, the term nucleotide also includes those species that have a detectable label, such as for example a radioactive or fluorescent moiety, or mass label attached to the nucleotide.

The term "off-target" and the phrase "off-target effects" refer to any instance in which an siRNA or shRNA directed against a given target causes an unintended effect by interacting either directly or indirectly with another mRNA sequence, a DNA sequence, a cellular protein, or other moiety. For example, an "off-target effect" may occur when there is a simultaneous degradation of other transcripts due to partial homology or complementarity between that other transcript and the sense and/or antisense strand of the siRNA or shRNA The term "overhang" refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. The single-stranded region extending beyond the 3' and/or 5' end of the duplex is referred to as an overhang.

The term "ribonucleotide" and the phrase "ribonucleic acid" (RNA), refer to a modified or unmodified nucleotide or polynucleotide comprising at least one ribonucleotide unit. A ribonucleotide unit comprises an oxygen attached to the 2' position of a ribosyl moiety having a nitrogenous base attached in N-glycosidic linkage at the 1' position of a ribosyl moiety, and a moiety that either allows for linkage to another nucleotide or precludes linkage.

The phrase "RNA interference" and the term "RNAi" are synonymous and refer to the process by which a single, double, or tripartite molecule (e.g. an siRNA, an shRNA, an miRNA, a piRNA) exerts an effect on a biological process by interacting with one or more components of the RNAi pathway including but not limited to Drosha, RISC, Dicer, etc. The process includes, but is not limited to, gene silencing by degrading mRNA, attenuating translation, interactions with tRNA, rRNA, hnRNA, cDNA and genomic DNA, inhibition of as well as methylation of DNA with ancillary proteins. In addition, molecules that modulate RNAi (e.g. siRNA, piRNA, or miRNA inhibitors) are included in the list of molecules that enhance the RNAi pathway (Tomari, Y. et al. Genes Dev. 2005, 19(5):517-29).

The phrase "sense strand" refers to a polynucleotide or region that has the same nucleotide sequence, in whole or in part, as a target nucleic acid such as a messenger RNA or a sequence of DNA. When a sequence is provided, by convention, unless otherwise indicated, it is the sense strand (or region), and the presence of the complementary antisense strand (or region) is implicit.

The phrase "silencing" is defined as an RNAi-mediated reduction in gene expression that can be measured by any number of methods including PCR-based methods, Northern blot analysis, Branched DNA, western blot analysis, and other art recognized techniques.

The term "siRNA" and the phrase "short interfering RNA" refer to unimolecular nucleic acids and to nucleic acids comprised of two separate strands that are capable of performing RNAi and that have a duplex region that is from about 18 to about 30 base pairs in length. Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides.

The phrase "pharmaceutically acceptable carrier" means a pharmaceutically acceptable salt, solvent, suspending agent or vehicle for delivering a composition of the present disclosure to the animal or human. The carrier may be liquid, semisolid or solid, and is often synonymously used with diluent, excipient or salt. The phrase "pharmaceutically acceptable" means that an ingredient, excipient, carrier, diluent or component disclosed is one that is suitable for use with humans and/or animals without undue adverse side effects (such as toxicity, irritation, and allergic response) commensurate with a reasonable benefit/risk ratio. See Remington's Pharmaceutical Sciences 16th edition, Osol, A. Ed. (1980).

The following embodiments are presented in order to aid in an understanding of the present disclosure and are not intended, and should not be construed, to limit the disclosure in any way. All alternatives, modifications and equivalents that may become apparent to those of ordinary skill upon reading this disclosure are included within the spirit and scope of the present disclosure.

According to a first aspect, the present disclosure is directed to duplex oligonucleotide complexes. The duplex oligonucleotide complexes of the disclosure comprise:
1. a sense strand that ranges in size from about 18 to about 30 nucleotides,
2. an antisense strand that ranges in size from about 18 to about 30 nucleotides, and has significant levels of complementarity to the sense strand as well as a target gene, wherein the sense strand and the antisense strand form a duplex;
3. a conjugate moiety that facilitates cellular delivery; and
4. a linker molecule that is from about 3 to about 9 atoms in length and attaches the conjugate to the sense strand.

By "significant levels of complementarity to the sense strand as well as a target gene" is meant that the antisense strand possesses sufficient complementarity with the sense strand to allow a duplex to form, and also possesses sufficient complementarity with a target gene to allow RNA interference to occur following Dicer processing of the duplex oligonucleotide complex. The antisense strand preferably exhibits at least 80% complementary to the sense strand and to the target gene i.e. substantial complementarity. The individual features of the duplex oligonucleotide complexes of the disclosure are now disclosed.

Conjugate Moieties

Conjugate moieties of the disclosure (also referred to simply as "conjugates") can vary widely and target entry into the cell by a variety of means. For instance, conjugate moieties can be lipid in nature and deliver their payload (e.g. siRNA or other nucleic acid), by inserting themselves into the membrane and being absorbed into the cell by one of several mechanisms including endocytosis. As such, lipid-based conjugate moieties can include cationic lipids, neutral lipids, sphingolipids, and fatty acids including stearic, oleic, elaidic, linoleic, linoleaidic, linolenic, and myristic acids. Alternatively, the conjugate moieties can be proteinaceous in nature including peptides that are membrane translocating (e.g. TAT, penetratin, MAP) or cationic (e.g. poly(lys), poly(arg), poly (his), poly(lys/arg/his), or protamine).

Alternatively, the conjugate moiety can be a small molecule that, for instance, targets a particular receptor or (again) is capable of inserting itself into the membrane and being absorbed by endocytic pathways. Thus, small molecules based on adamantanes, polyaromatic hydrocarbons (e.g. napthalenes, phenanthrenes, or pyrenes), macrocyles, steroids, or other chemical scaffolds, are all potential conjugates for the disclosure.

In yet another alternative, conjugate moieties can be based on cationic polymers. Numerous studies have demonstrated that cationic polymers such as cationic albumin can greatly enhance delivery to particular cell types and/or tissues (e.g. brain delivery, see Lu, W. et. al. (2005) J of Control Release 107:428-448). Given the benefits of these molecules, the conjugate moieties can be cationic polymers such as polyethyleneimine, dendrimers, poly(alkylpyridinium) salts, or cationic albumin.

In some cases, the conjugate moieties are ligands for receptors or can associate with molecules that (in turn) associate with receptors. Included in this class are bile acids, small molecule drug ligands, vitamins, aptamers, carbohydrates, peptides (including but not limited to hormones, proteins, protein fragments, antibodies or antibody fragments), viral proteins (e.g. capsids), toxins (e.g. bacterial toxins), and more. Also included are conjugates that are steroidal in nature e.g. cholesterol, cholestanol, cholanic acid, stigmasterol, pregnolone, progesterones, corticosterones, aldosterones, testosterones, estradiols, ergosterols, and more), Preferred conjugate moieties of the disclosure are cholesterol (CHOL), cholestanol (CHLN), cholanic acid (CHLA), stigmasterol (STIG), and ergosterol (ERGO). In certain preferred embodiments, the conjugate moiety is cholesterol.

In the case of cholesterol, the molecule can associate with one or more proteins or protein complexes in e.g. the blood (e.g. albumin, LDLs, HDLs, IDLs, VLDLs, chylomicron remnants, and chylomicrons) and be delivered to the cell through association with the appropriate receptor for that complex (e.g. the LDLR, low density lipoprotein receptor). The example of delivery via the cholesterol-LDL association is particularly attractive since the opportunity for dozens or hundreds of siRNA to be delivered in a single LDL particle is feasible. For that reason, the inventors can envision packaging cholesterol conjugated siRNAs or siRNA conjugated to derivatives of cholesterol, in one or more natural carriers (e.g. LDLs) in vitro, and using this as an in vivo delivery system.

In yet another embodiment, the molecules that target a particular receptor are modified to eliminate the possible loss of conjugated siRNAs to other sources. For instance, when cholesterol-conjugated siRNAs are placed in the presence of normal serum, a significant fraction of this material will associate with the albumin and/or other proteins in the serum, thus making the siRNA unavailable for e.g. interactions with LDLs. For this reason, the conjugate moieties of the disclosure can be modified in such a way that they continue to bind or associate with their intended target (e.g. LDLs) but have lesser affinities with unintended binding partners (e.g. serum albumin).

The Linker

Though not wishing to be limited by definitions or conventions, in this application the length of the linker is described by counting the number atoms that represents the shortest distance between the atom that joins the conjugate moiety to the linker and the oxygen atom of the terminal phosphate moiety associated with the oligonucleotide through which the linker is attached to the oligonucleotide. For example, in embodiments where the conjugate moiety is joined to the linker via a carbamate linkage, the length of the linker is described as the number of atoms that represents the shortest distance between the nitrogen atom of the carbamate linkage and the oxygen atom of the phosphate linkage. In cases where ring structures are present, counting the atoms around the ring that represent the shortest path is preferred.

Non-limiting examples of structures of the conjugate-linker which may be used in the compositions and methods of the disclosure are provided in Table I. Alternative chemistries can be used and provide a similar length linker to linkers exemplified in Table I. For example, linkers/linker chemistries that are based on ω-amino-1,3-diols, hydroxyprolinols, ω-amino-alkanols, diethanolamines, ω-hydroxy-1,3-diols, ω-hydroxy-1,2-diols, ω-thio-1,2-diols, ω-carboxy-1,3-diols, ω-carboxy-1,2-diols, ω-hydroxy-alkanols, ω-thio-alkanols, ω-carboxy-alkanols, functionalized oligoethylene glycols, allyl amine, acrylic acid, alkyl alcohol, propargyl amine, propargyl alcohol, and more, can be applied in this context to generate linkers of the appropriate length.

In some embodiments a linker not only provides a site of attachment to the conjugate moiety, but also provides functional sites for attachment to the support and for initiation of oligonucleotide synthesis. Preferably, these sites are hydroxyl groups; most preferably, they are a primary hydroxyl group and a secondary hydroxyl group, to allow them to be chemically distinguished during synthesis of the conjugate-modified solid support. One hydroxyl group, preferably the primary hydroxyl group, is protected with a protecting group that can be removed as the first step in the synthesis of the oligonucleotide, according to methods well understood by those of ordinary skill in the art. Preferably, this protecting group is chromophoric and can be used to estimate the amount of the conjugate moiety attached to the solid support; most preferably, the group is chosen from triphenylmethyl (Tr), monomethoxytriphenylmethyl (MMTr), dimethoxytriphenylmethyl (DMTr) and trimethoxytriphenylmethyl (TMTr). Another hydroxyl group, preferably a secondary hydroxyl group, is derivatized with a functionalized tether that can covalently react with a functional group on the solid synthesis support, according to methods well understood by those of ordinary skill in the art. Preferable tethers are, by way of example, dicarboxylic acids such as succinic, glutaric, terephthalic, oxalic, diglycolic, and hydroquinone-O,O'-diacetic. One of the carboxylic acid functionalities of the tether is reacted with the hydroxyl to provide an ester linkage that is cleavable using basic reagents (hydroxide, carbonate or amines), while the other carboxylic acid functionality is reacted with the synthesis support, usually through formation of an amide bond with an amine functionality on the support.

The linker may also confer other desirable properties on the oligonucleotide conjugate: improved aqueous solubility, optimal distance of separation between the conjugate moiety and the oligonucleotide, flexibility (or lack thereof), specific orientation, branching, and others.

Preferably, the chemical bond between the linker and the conjugate moiety is a carbamate linkage; however, alternative chemistries are also within the scope of the disclosure. Examples of functional groups on linkers which form a chemical bond with a conjugate moiety include, but are not limited to, hydroxyl, amine, carboxylic acid, carboxylic acid halide, carboxylic acid active ester, carbonyl, chlorocarbonyl, imidazolylcarbonyl, thiol, maleimide, haloalkyl, sulfonyl, allyl and propargyl. Examples of chemical bonds that are formed between a linker and a conjugate include, but are not limited to, those based on carbamates, ethers, esters, amides, disulfides, thioethers, phosphodiesters, phosphorothioates, phorphorodithioate, sulfonamides, sulfonates, fulfones, sulfoxides, ureas, hydrazide, oxime, photolabile linkages, C—C bond forming groups such as Diels-Alder cyclo-addition pairs or ring-closing metathesis pairs, and Michael reaction pairs. In general, the conjugate moiety will have an appropriate functional group either naturally or chemically installed; the linker will then be synthesized with a functional group chosen to efficiently and stably react with the functional group on the conjugate moiety.

Linkers that have the same length, but are capable of associating with two or more conjugates, are also specifically contemplated.

In another embodiment, the linker may be a nucleoside derivative. The nucleoside may be, for example, a ribonucleoside, 2'-deoxyribonucleoside, or 2'-modified-2'-deoxyribonucleoside, such as 2'-O-methyl or 2'-fluoro. The nucleoside may be, for example, an arabinonucleoside or a 2'-modified arabinonucleoside. Using methods well known to those of ordinary skill in the art, purine and pyrimidine nucleosides may be modified at particular sites on the base to provide linkers and functional groups for attachment of conjugate moieties. For example, pyrimidine nucleosides, such as uridine and cytidine, may be modified at the 5-position of the uracil or cytosine base using mercuric acetate, a palladium catalyst, and an allylic reagent such as allylamine, allyl alcohol, or acrylic acid. Alternatively, 5-iodopyrimidines may be modified at the 5-position with a palladium catalyst and a propargylic reagent such as propargyl amine, propargyl alcohol or propargylic acid. Alternatively, uridine may be modified at the 4-position through activation with triazole or a sulfonyl chloride and subsequent reaction with a diamine, amino alcohol or amino acid. Cytidine may be similarly modified at the 4-position by treatment with bisulfite and subsequent reaction with a diamine, amino alcohol or amino acid. Purines may be likewise modified at the 7, 8 or 9 positions using similar types of reaction sequences.

In preferred embodiments, the linker is from about 3 to about 9 atoms in length. Thus, the linker may be 3, 4, 5, 6, 7, 8, or 9 atoms in length. Preferably, the linker is 5, 6, 7, or 8 atoms in length. More preferably, the linker is 5 or 8 atoms in length. Most preferably the linker is a straight chain C5 linker i.e., there are 5 carbon atoms between the atom that joins the conjugate moiety to the linker and the oxygen atom of the terminal phosphate moiety associated with the oligonucleotide through which the linker is attached to the oligonucleotide. Thus, where the conjugate moiety is joined to a C5 linker via a carbamate linkage, there are 5 carbon atoms between the nitrogen atom of the carbamate linkage and the oxygen atom of the phosphate linkage.

In one preferred embodiment, the conjugate moiety is cholesterol and the linker is a C5 linker (a 5 atom linker) attached to the cholesterol via a carbamate group, thus forming a Chol-C5 conjugate-linker (see Table I). When attached via a phosphodiester linkage to the 5' and/or 3' terminus of a sense and/or antisense oligonucleotide of a duplex, the resulting conjugate-linker-oligonucleotide can have the structure:

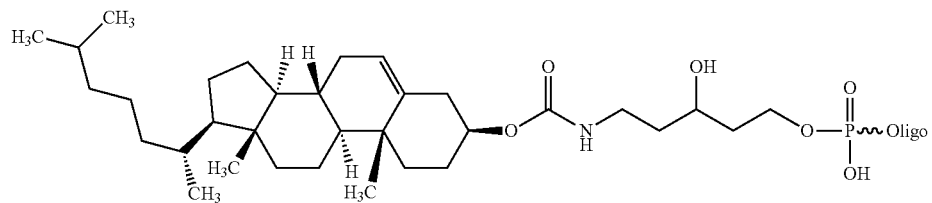

In another preferred embodiment, the conjugate moiety is cholesterol and the linker is a C3 linker attached to the cholesterol via a carbamate group, thus forming a Chol-C3 conjugate-linker (see Table I). When attached via a phosphodiester linkage to the 5' and/or 3' terminus of a sense and/or antisense oligonucleotide, the resulting conjugate-linker-oligonucleotide can have the structure:

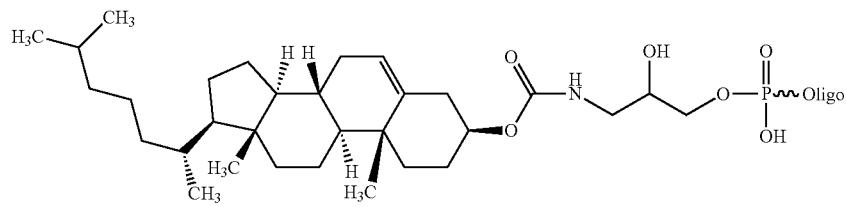

In another preferred embodiment, the conjugate moiety is cholesterol and the linker is a C8 linker (a 8 atom linker) attached to the cholesterol via a carbamate group, thus forming a Chol-C8 conjugate-linker (see Table I). When attached via a phosphodiester linkage to the 5' and/or 3' terminus of a sense and/or antisense oligonucleotide, the resulting conjugate-linker-oligonucleotide can have the structure:

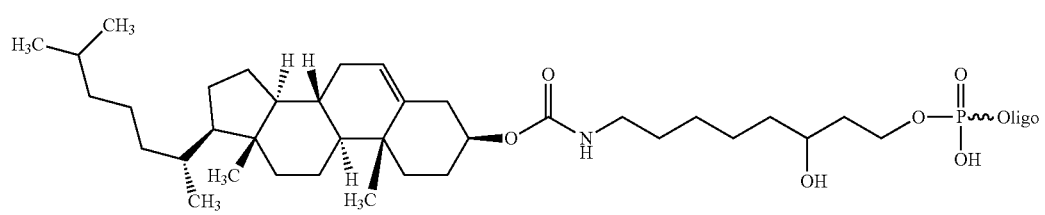

In another preferred embodiment, the conjugate moiety is cholesterol and the linker is a PRO linker (a 4 atom linker) attached to the cholesterol via a carbamate group, thus forming a Chol-PRO conjugate-linker (see Table I). When attached via a phosphodiester linkage to the 5' and/or 3' terminus of a sense and/or antisense oligonucleotide, the resulting conjugate-linker-oligonucleotide can have the structure:

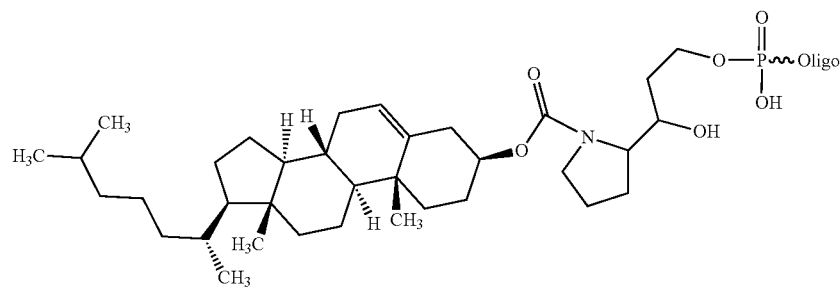

In another preferred embodiment, the conjugate moiety is cholesterol and the linker is a PIP linker (a 6 atom linker) attached to the cholesterol via a carbamate group, thus forming a Chol-PIP conjugate-linker (see Table I). When attached via a phosphodiester linkage to the 5' and/or 3' terminus of a sense and/or antisense oligonucleotide, the resulting conjugate-linker-oligonucleotide can have the structure:

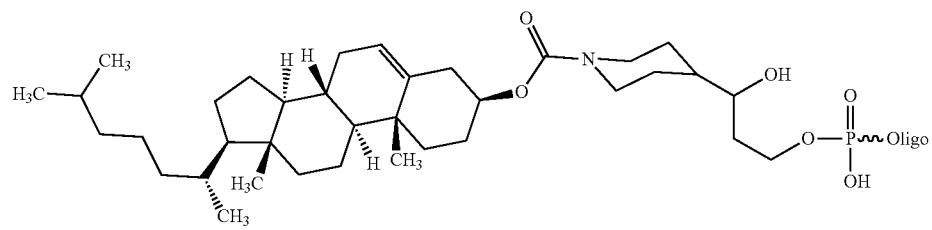

In another preferred embodiment, the conjugate moiety is cholesterol and the linker is a C6-HP (also referred to as "HP6") linker (a 9 atom linker) attached to the cholesterol via a carbamate group, thus forming a Chol-C6-HP conjugate-linker (see Table I). When attached via a phosphodiester linkage to the 5' and/or 3' terminus of a sense and/or antisense oligonucleotide, the resulting conjugate-linker-oligonucleotide can have the structure:

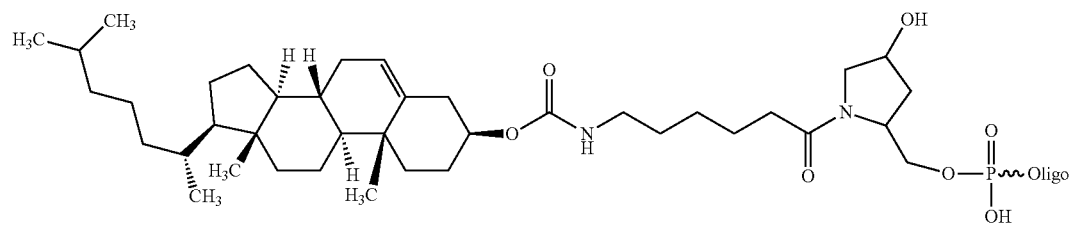

It is explicitly contemplated that the C5, C3, C8, PRO, C6-HP and PIP linkers in the foregoing embodiments (along with the additional linkers shown in Table I) can be used with conjugate moieties other than cholesterol, including, for example, cholestanol (CHLN), cholanic acid (CHLA), stigmasterol (STIG), and ergosterol (ERGO). It will also be understood that while the C5, C3, C8, PRO, C6-HP, and PIP linkers exemplified above (and the additional linkers shown in Table I) are shown with a carbamate group attaching the conjugate to the linker, other attachment chemistries may be used (see below). Finally, while the C5, C3, C8, PRO, C6-HP, and PIP linkers in the foregoing embodiments are shown attached to oligonucleotides via a phosphodiester linkage, it will be appreciated that other sites of attachment to oligonucleotides, and other chemistries for attachment to oligonucleotides, may be used (see below).

In some embodiments, the duplex oligonucleotide complex also includes a detectable label, such as a dye molecule or a radiolabel. Suitable dye molecules include, but are not limited to, fluorescent dye molecules and phosphorescent dye molecules. Suitable fluorescent dyes include TAMRA, BODIPY, Cyanine derivatives such as Cy3 or Cy5 Dabsyl, fluoroscein, or any other suitable fluorophore known in the art. A detectable label may be attached at any position in the duplex oligonucleotide complex, preferably at the 5' or 3' end of one or more of the strands. Most preferably, the detectable label is a fluorescent dye molecule which is attached to the 5' end of the sense strand. The detectable label may be attached using any method known in the art. In addition, the detectable label may be attached using any of the aforementioned linkers. The use of dye molecules allows one skilled in the art to monitor the transfection efficiency of the duplex oligonucleotide complexes.

Conjugate-Linker Position on the Duplex Oligonucleotide Complex

The position of the conjugate-linker on the duplex oligonucleotide complex can vary with respect to the strand or strands that are conjugated (e.g. the sense strand, the antisense strand, or both the sense and antisense strands), the position or positions within the strand that are modified (i.e. the nucleotide positions within the strand or strands), and the position on the nucleotide(s) that are modified (e.g. the sugar, the base). Conjugate-linkers can be placed on the 5' and/or 3' terminus of one or more of the strands of the disclosure. For example, a conjugate-linker can be placed on the 5' end of the sense strand and/or the 3' end of the sense strand and/or the 5' end of the antisense strand and/or the 3' end of the antisense strand. A conjugate-linker can be attached the 5' and/or 3' end of a strand via a phosphodiester bond. In preferred embodiments, a conjugate-linker is attached to the one or both ends of the sense strand via a phosphodiester bond, more preferably to the 3' end of the sense strand.

A conjugate-linker can also be attached to internal positions of the sense strand and/or antisense strand. In addition, multiple positions on the nucleotides including the 5-position of uridine, 5-position of cytidine, 4-position of cytidine, 7-position of guanosine, 7-position of adenosine, 8-position of guanosine, 8-position of adenosine, 6-position of adenosine, 2'-position of ribose, 5'-position of ribose, 3'-position of ribose, can be employed for attachment of the conjugate to the nucleic acid.

The Duplex Formed by the Sense and Antisense Strands

The sense and the antisense strands range in size from about 18 to about 30 nucleotides. For example, the sense and antisense strands may be 18, 19, 20, 21, 22, 23, 24, 25, 26, 27, 28, 29, or nucleotides in length. Preferably, the sense and antisense strands are between 19 and 23 nucleotides long, most preferably 19 nucleotides long (not including any overhang(s) which may be present (see below)). The sequences of the sense and/or antisense strands of the duplex oligonucleotide complex can be selected by a variety of methods known in the art including random selection based on the sequence of the gene and rational design methods (using any one of a number of art-recognized algorithms and/or neural networks) as long as the sequence can effectively silence a target gene with no or minimal off-target, or deleterious effects. Detailed descriptions of the criteria for the rational design of antisense strands for efficient gene silencing can be found in WO 2004/045543, WO 2006/006948, WO 2005/078095, WO 2005/097992, and WO 2005/090606.

A broad range of modifications can be included in the sense and antisense strands to enhance stability, Dicer or RISC processing, functionality, and/or specificity. In addition, modifications can be used to minimize the innate immune response that cells typically have against dsRNAs that are longer than e.g. 23 bp (see Reynolds, A. et al (2006) RNA. 12(6):988-930). Modifications to the internucleotide linkages that can enhance overall stability or enzymatic processing can include phosphorothioates, phosphorodithioates, alkylphosphonates, phosphonoacetates, phosphonoacetamides, phosphonoacetic acid esters, phosphonamidates, phosphonoalcohols, phosphonoalcohol esters, phosphonoformates, boranophosphonates, peptide nucleic acids, and more. Similarly, chemically modified nucleotides having modifications to the sugar structures can be included to enhance or alter oligonucleotide stability, functionality, enzymatic processing, and specificity. Possible modifications to the sugar ring structure include 2'-O-alkylribose, 2'-halo-2'-deoxyribose, 2'-deoxyribose, 2' amino-2'-deoxyribose, 2'-thio-2'-deoxyribose, arabinose, L-ribose, 2'-halo-2'-deoxyarabinose, 2'-O-alkylarabinose, 2'-amino-2'-deoxyarabinose, 2'-thio-2'-deoxyarabinose, 2'-O, 4'-C-methylene bicycloribose ("locked nucleic acid"), 4'-aminoalkylribose, 5'-aminoalkylribose, 4-thioribose, and more.

Preferably, between about 40% and about 90% of the nucleotides of the sense strand and between about 40% and about 90% of the nucleotides of the antisense strand are chemically modified nucleotides. Preferred sets of chemical modifications include 1) 2' O-alkyl modification, preferably 2'-O-methyl modification, of nucleotides 1 and/or 2 of the sense strand (numbered from the 5' end), and/or 2) 2' O-alkyl modification, preferably 2'-O methyl modification, of some or all of the Cs and Us of the sense strand, and/or 3) 2' halogen modification, preferably 2'F modification, of some or all of the Cs and Us of the antisense strand. In one preferred embodiment, nucleotides 1 and 2, and all C and U nucleotides, of the sense strand are 2' O-methyl modified, and all C and U nucleotides in the antisense strand are 2' F modified.

In addition to internucleotide and sugar modifications, a number of base analogs can be included in the sense strand and/or the antisense strand. Such analogs can be included to enhance, or minimize base pairing at desired positions so as to increase specificity or functionality, enhance or minimize interaction with one or more proteins in the RNAi pathway or targets, and to minimize activation of the innate immune response. Base analogs include iso-cytidine/iso-guanosine, 2-aminopurine, pseudouridine, 5-methyluridine, 3-methyluridine, nitroindoles, imidazoles, pyridines, 5-azapyrimidines, 6-azapyrimidines, 7-deazapurines, 5-halopyriomidines, 8-halopurines, 8-oxopurines, 2-thiopyrimidines, 6-thioguanosine, 4-thiouridine, 2,6-diaminopurine, and more. Lastly, in addition to the three classes of modifications described above, nucleoside modifications that include morpholino nucleosides, 1',5'-anhydrohexitol nucleosides, 2,3-dideoxyhexopyranosyl nucleoside, carbocyclic nucleosides, C-nucleosides, and acyclic nucleosides (e.g. acyclovir, ganciclovir, penciclovir, and deciclovir), and any number of chemistries that can lead to universal base pairing, can be included in the disclosure.

In addition, the duplex formed by the sense strand and the antisense strand can comprise at least one overhang, each overhang comprising at least one nucleotide. The overhang(s) can be located:

- at the 5' end of the sense strand;
- at the 3' end of the sense strand;
- at the 5' and 3' end of the sense strand;
- at the 5' end of the antisense strand;
- at the 3' end of the antisense strand;
- at the 5' and 3' end of the antisense strand;
- at the 5' end of the sense strand and the 5' end of the antisense strand; or
- at the 3' end of the sense strand and the 3' end of the antisense strand In preferred embodiments, an overhang is present at the 3' end of the antisense strand. More preferably, the overhang on the 3' end of the antisense strand is a 2 nucleotide overhang. The selection of the bases for nucleotides in the overhang is made in an arbitrary manner i.e., the overhang nucleotides may or may not base pair with a target mRNA. For convenience and simplicity, a 2 nucleotide overhang is usually a UU overhang (although AA, GG, CC, AC, CA, AG, GA, GC, and CG 2 nucleotide overhangs, and others, are also contemplated, see Vermeulen et al, (2005) RNA 11(5):674-682). The nucleotides and/or the internucleotide linkages in the overhang may be modified with any of the nucleotide or internucleotide linkage modifications described above. Preferably, the internucleotide linkages in the overhang comprises phosphorothioate linkages. In one particularly preferred embodiment, the antisense strand comprises a 2 nucleotide UU overhang located at the 3' end of the antisense strand with a phosphorothioate linkage linking the 3' terminal U to the second U nucleotide, and with a phosphorothioate linkage linking the second U nucleotide to the next nucleotide (in the 5' direction) in the antisense strand.

In some embodiments, the 5' end of the sense strand and/or the 3' end of the sense strand and/or the 5' end of the antisense strand and/or the 3' end of the antisense strand comprises a terminal phosphate. Preferably, a terminal phosphate is located at the 5' end of the antisense strand.

In some embodiments, there is at least one mismatch between a nucleotide on the antisense strand and the opposite nucleotide on the sense strand, preferably a mismatch between nucleotide 10, 11, 12, 13, or 14 on the antisense strand (numbered from the 5' end and not counting any overhang which may be present at the 5' end) and the opposite nucleotide(s) on the sense strand. In certain preferred embodiments, the duplex comprises a single mismatch between nucleotide 14 on the antisense strand (numbered from the 5' end) and the opposite nucleotide on the sense strand. Where the sense and antisense strands are 19 nucleotides in length (not counting any overhangs), position 14 of the antisense strand is opposite position 6 of the sense strand (both numbered from the 5' end of the respective strand, but not counting any overhangs). Where the sense and antisense strands are 18, 20, 21, 22, 23, 24, 25, 26, 27, 28, 29, or 30 nucleotides in length (not counting any overhangs), position 14 of the antisense strand is opposite position 5, 7, 8, 9, 10, 11, 12, 13, 14, 15, 16, or 17 respectively of the sense strand (both numbered from the 5' end of the respective strand, and not counting any overhangs).

Relative to the same duplex without the mismatch, a duplex with a mismatch comprises a single nucleotide substitution on the sense strand, thus preserving perfect complementarity between the antisense strand and the target mRNA. Preferably, the mismatched nucleotide on the sense strand in such a mismatched duplex has the same base as nucleotide 14 on the antisense strand, thereby forming a A/A (if nucleotide 14 on the antisense strand is A), U/U (if nucleotide 14 on the antisense strand is U), G/G (if nucleotide 14 on the antisense strand is G), or C/C mismatch (if nucleotide 14 on the antisense strand is C).

Combinations of the Features

One skilled in the art will appreciate that there are many ways in which to combine the features disclosed above—the design of the duplex formed by the sense and antisense strands, the identity of the linker(s), the identity of the conjugate moiety(s), conjugate-linker position, positions of chemically modified nucleotides etc—in order to provide duplexes oligonucleotide complexes within the scope of the disclosure. Every possible combination of features is explicitly contemplated. The following duplex oligonucleotide complexes are provided solely as non-limiting Examples of the manner in which the novel features disclosed herein may be combined.

One example of a duplex oligonucleotide complex comprises:
1. a sense strand that ranges in size from about 18 to about 30 nucleotides wherein nucleotides 1 and 2 (numbered from the 5' end) are 2' O-methyl modified and wherein all C nucleotides and U nucleotides are 2'O-methyl modified;
2. an antisense strand that ranges in size from about 18 to about 30 nucleotides, wherein all C nucleotides and all U nucleotides are 2' F modified, wherein the antisense strand has significant levels of complementarity to the sense strand as well as a target gene and wherein the sense strand and the antisense strand form a duplex;
3. a 2 nucleotide overhang at the 3' end of the antisense strand comprising phosphorothioate linkages;
4. a cholestanol molecule attached to the 3' end of the sense strand via a C5 linker molecule wherein the cholestanol-linker-sense strand can have the structure:

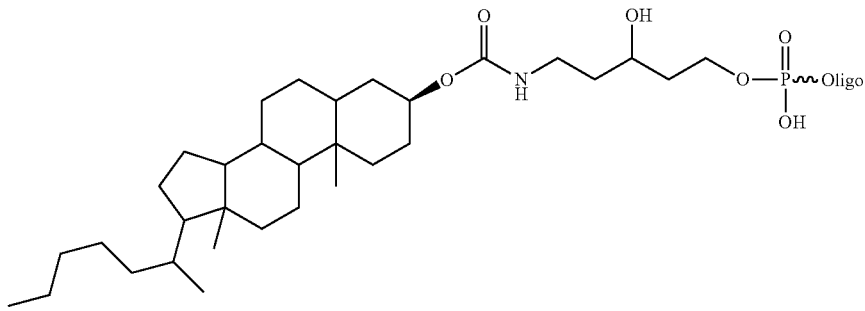

5. a phosphate group at the 5' end of the antisense strand; and
6. optionally, a mismatch between nucleotide 14 on the antisense strand (numbered from the 5' end) and the opposite nucleotide on the sense strand.

Another example of a duplex oligonucleotide complex comprises:

1. a sense strand that ranges in size from about 18 to about 30 nucleotides wherein nucleotides 1 and 2 (numbered from the 5' end) are 2' O-methyl modified and wherein all C nucleotides and U nucleotides are 2'O-methyl modified;
2. an antisense strand that ranges in size from about 18 to about 30 nucleotides, wherein all C nucleotides and all U nucleotides are 2' F modified, wherein the antisense strand has significant levels of complementarity to the sense strand as well as a target gene and wherein the sense strand and the antisense strand form a duplex;
3. a 2 nucleotide overhang at the 3' end of the antisense strand comprising phosphorothioate linkages;
4. a stigmasterol molecule attached to the 3' end of the sense strand via a C5 linker molecule wherein the stigmasterol-linker-sense strand can have the structure:

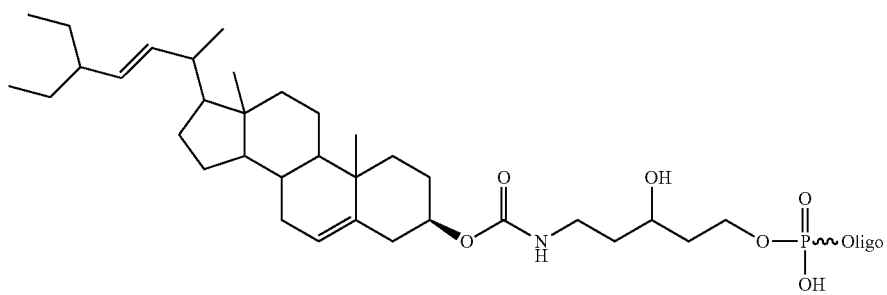

5. a phosphate group at the 5' end of the antisense strand.
6. optionally, a mismatch between nucleotide 14 on the antisense strand (numbered from the 5' end) and the opposite nucleotide on the sense strand.

Another example of a duplex oligonucleotide complex comprises:

1. a sense strand that ranges in size from about 18 to about 30 nucleotides wherein nucleotides 1 and 2 (numbered from the 5' end) are 2' O-methyl modified and wherein all C nucleotides and U nucleotides are 2'O-methyl modified;
2. an antisense strand that ranges in size from about 18 to about 30 nucleotides, wherein all C nucleotides and all U nucleotides are 2' F modified, wherein the antisense strand has significant levels of complementarity to the sense strand as well as a target gene and wherein the sense strand and the antisense strand form a duplex;
3. a 2 nucleotide overhang at the 3' end of the antisense strand comprising phosphorothioate linkages;
4. a ergosterol molecule attached to the 3' end of the sense strand via a C5 linker molecule wherein the ergosterol-linker-sense strand can have the structure:

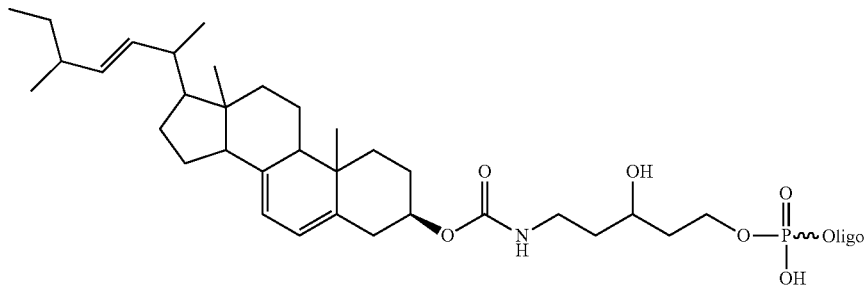

5. a phosphate group at the 5' end of the antisense strand.
6. optionally, a mismatch between nucleotide 14 on the antisense strand (numbered from the 5' end) and the opposite nucleotide on the sense strand.

Another example of a duplex oligonucleotide complex comprises:

1. a sense strand that ranges in size from about 18 to about 30 nucleotides wherein nucleotides 1 and 2 (numbered from the 5' end) are 2' O-methyl modified and wherein all C nucleotides and U nucleotides are 2'O-methyl modified;
2. an antisense strand that ranges in size from about 18 to about 30 nucleotides, wherein all C nucleotides and all U nucleotides are 2' F modified, wherein the antisense strand has significant levels of complementarity to the sense strand as well as a target gene and wherein the sense strand and the antisense strand form a duplex;
3. a 2 nucleotide overhang at the 3' end of the antisense strand comprising phosphorothioate linkages;
4. a cholesterol molecule attached to the 3' end of the sense strand via a C5 linker molecule wherein the cholesterol-linker-sense strand can have the structure:

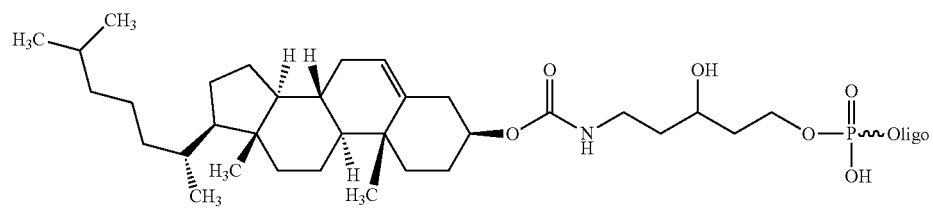

5. a phosphate group at the 5' end of the antisense strand; and
6. optionally, a mismatch between nucleotide 14 on the antisense strand (numbered from the 5' end) and the opposite nucleotide on the sense strand.

Such Chol-05 complexes are generically referred to herein as "G4 complexes" "G4 siRNA," or simply as "G4." When referring to a specific G4 siRNA, the suffix "(+mm)" indicates that the G4 siRNA includes a mismatch between nucleotide 14 on the antisense strand (numbered from the 5' end) and the opposite nucleotide on the sense strand, and the suffix "(−mm)" indicate that the G4 siRNA lacks such a mismatch.

Indirect Conjugates and Formulations

A number of indirect conjugates can be used in conjunction with any of the duplex oligonucleotide complexes of the disclosure. Thus, any of the duplex oligonucleotide complexes previously described, e.g., G4, can be used jointly with protein (e.g. antibody) fusion constructs, polycations, cationic peptides, zinc fingers, aptamers, histones, dsRNA binding proteins, single stranded nucleic acid binding proteins, heparin binding domains, KH domains, PAZ domains, viral capsid proteins and transcription factors or domains. Formulations based on peptides, lipo- or poly-plexes, dendrimers, heparin, cholesterol, albumin, LDL blocking molecules, receptor blocking molecules, endosomal disrupting compounds or mixtures, neutral lipids, poly histidines, protamine, amino acids, taxol, time-released formulations, and nanoparticles (e.g., quantum dots, calcium phosphate or carbon nanotubes) are all compatible with the duplex oligonucleotide complexes of the disclosure.

Methods of Delivery

The duplex oligonucleotide complexes of the disclosure may be employed in methods related to RNAi. As stated previously, methods related to RNAi include, but are not limited to targeting a gene or genes with siRNA, shRNA, miRNAs, or piRNAs. In addition, the targeting of miRNAs, siRNAs, shRNAs, or piRNAs with inhibitors are included as methods related to RNAi.

The duplex oligonucleotide complexes of the disclosure are particularly potent in silencing genes by the RNAi pathway. Duplex oligonucleotide complexes of the disclosure which comprise cholesterol (CHOL), cholestanol (CHLN), cholanic acid (CHLA), stigmasterol (STIG), or ergosterol (ERGO) as a conjugate, especially when linked to the 3' end of a sense strand via a C5 linker (such as G4 complexes), are particularly useful because they can be used to passively deliver (i.e., deliver without additional transfection reagents) their attached duplex oligonucleotide to cells in culture or other environments in order to silence or knockdown genes. It is expressly contemplated that such molecules (e.g., G4) are passively delivered to cells in culture (e.g., in culture plates, culture dishes, multiwell plates etc without limitation). It is also expressly contemplated that such molecules (e.g., G4) are passively delivered to cells under reduced serum conditions, including under 0% serum (i.e., serum free) conditions. Such conditions include cells cultured in standard, art-tested reduced-serum media that are commercially available from numerous companies including Invitrogen, and HyClone. In one example, cells are first plated in serum medium, then the serum medium is replaced with reduced serum medium comprising a duplex oligonucleotide complex of the disclosure (e.g., G4) for 24 hours, then the reduced serum medium is replaced with serum medium.

Cell lines in which passively-delivered G4 siRNA has been effectively employed in gene silencing include, but are not limited to: Human Adherent Cells: SH-SY5Y: Neuroblastoma, IMR32: Neuroblastoma, LAN5; Neuroblastoma, HeLa: Cervix; Adenocarcinoma, HeLa S3: Cervix; Adenocarcinoma, LNCap: Prostate; Metastatic, MCF10A: Epithelial; mammary gland, 293T: Epithelial; kidney, MCF-7: Breast Cancer, SK-BR3: Breast Cancer, Huh7: Hepatoma, DU145: Prostate; mets: brain carcinoma, GTM-3: Glaucomatour trabecular meshwork, HT1080: Connective Tissue; Fibrosarcoma, U2OS: Bone, osteosarcoma, epithelial, DLD-1: Epithelial, colon, colorectal adenocarcinoma, A-375: Epithelial, skin, malignant melanoma, HepG2: Liver, Hepatocellular carcinoma, THP-1: Monocyte; Acute Monocytic Leukemia, Jurkat: T-Lymphocyte, Acute T cell Leukemia, Human Differentiated Stem Cells: Osteoblasts: From hMSC, Adipocytes: From hMSC, Primary Cells: HUVEC: Primary cells; Umbilical vein; endothelial, HUASMC (60% KD): Primary Smooth Muscle, Hepatocytes: Mouse, Liver, hMSC: Undifferentiated mesenchymal, PBMC: Peripheral blood mononuclear cells, NHA: Human astrocytes, Other Species: 3T3 NIH: Mouse, Embryo; Fibroblast, 3T3 L1: Mouse, Embryo; Fibroblast, ES-D3: Mouse, Pluripotent embryonic stem cells, C2C12: Mouse, muscle myoblast, and H9c2: Rat, Heart, Myocardium.

The duplex oligonucleotide complexes of the disclosure may be conveniently supplied to end-users premixed in reduced serum media (including serum-free media). The duplex oligonucleotide complexes of the disclosure can be stored in such media at 4° C. for extended periods of time without significant loss of gene silencing activity. Thus, in one aspect, the disclosure provides a kit comprising one or more containers, each container comprising reduced serum media and a duplex oligonucleotide complex(es) of the disclosure such as G4 complexes. The kit may also comprise instructions that instruct one skilled in the art how to passively-deliver the duplex oligonucleotide complex to cells in accordance with the teachings of the disclosure. In this way, the duplex oligonucleotide complexes of the disclosure may be purchased by a consumer in a stable and ready-to-use formulation. Gene silencing may then be carried out by simply culturing cells in the supplied formulation without additional transfection steps. In addition, if the supplied formulation comprises a plurality of duplex oligonucleotide complexes, each specific for a particular gene, then a single supplied formulation may be used for the simultaneous silencing of a plurality of genes. If a single gene is to be silenced, then the supplied formulation may comprise a single duplex oligonucleotide complex of the disclosure, or it may comprise a pool of duplex oligonucleotide complexes, each targeting a different region of, for example, a single target mRNA of interest.

In another embodiment, the duplex oligonucleotide complexes of the disclosure are used to silence genes in cultured cells in a "reverse transfection" format. In this format, the duplex oligonucleotide complexes of the disclosure are first dispensed onto a solid support (such as a glass slide) and then cells are grown on the solid support. Cells that grow on the solid support take up the duplex oligonucleotide complexes through passive delivery. In preferred embodiments, a plurality of different duplex oligonucleotide complexes are attached at a plurality of spatially defined addresses on a solid support (for example, by printing or pipetting spots of duplex oligonucleotide complexes, e.g., G4, on the support), thus forming a microarray of duplex oligonucleotide complexes. Cells that are grown on the solid support thereby come into contact with different duplex oligonucleotide complexes in a position-dependent manner. The support can be modified or can be unmodified (e.g., with one or more polymers) that enhance retention or delivery of the duplex, or enhance adhesion of the cell population to the solid support.

Duplex oligonucleotide complexes of the disclosure which comprise cholesterol (CHOL), cholestanol (CHLN), cholanic acid (CHLA), stigmasterol (STIG), or ergosterol (ERGO) as a conjugate, especially when linked to the 3' end of a sense strand via a C5 linker (such as G4 complexes), are also particularly useful for continuous dosing of cells. Continuous dosing with the duplex oligonucleotide complexes of the disclosure is useful for achieving long term knockdown of a gene target. Moreover, cells continuously dosed with the duplex oligonucleotide complexes of the disclosure remain amenable to conventional lipid-mediated transfection. Thus, it is possible to use the duplex oligonucleotide complexes of the disclosure to knockdown a specific gene and then to use conventional lipid-mediated delivery of additional reagents that mediate RNAi (e.g., additional siRNAs) in order simultaneously to knockdown additional genes. In this way, it is possible to screen a panel of different siRNAs for a phenotype of interest in a "background" of a continuous knockdown of one specific gene.

In one embodiment, the compositions of the disclosure are used in basic research settings, in drug discovery settings, in ADME-tox applications, and in therapeutic/prophylactic applications.

In yet another embodiment, a method by which different combinations of linkers, conjugates, and delivery payloads are combined to screen for functional arrangement is described.

In yet another embodiment, a combi-chem approach to screen for conjugate structures that enhance nucleic acid delivery, preferably delivery of siRNAs, miRNAs, miRNA mimics, piRNAs, miRNA and piRNA inhibitors, is described.

In yet another embodiment, one or more compositions of the disclosure are used to perform small molecule screening.

In yet another embodiment, one or more compositions and/or methods of the disclosure are used to identify molecules that are capable of blocking the interaction of the molecules of the disclosure with another entity, such as a serum protein.

In yet another embodiment, one or more compositions and/or methods of the disclosure are used to optimize the backbone for universal attachment of ligands.

In yet another embodiment, one or more compositions of the disclosure are used in kits developed for transfection procedures. Such procedures can include 1) plating cells in e.g. a well and adding one or more compositions of the disclosure to the well for passive delivery or 2) depositing one or more compositions of the disclosure in a well or on a slide and adding cells to initiate passive delivery of the molecules of the disclosure. In both cases, such methods can be employed to introduce a homogeneous population of molecules into cells, or can be arrayed in such a way as to introduce larger collections (e.g. a genome wide collection of siRNA) into cells.

In another embodiment, the compositions of the disclosure are applied in high throughput screening methods.

In yet another embodiment, the compositions of the disclosure are employed to introduce nucleic acids e.g. siRNA into hard-to-transfect cells such as Jurkat cells, stem cells, cells of neuronal origin, and cells of a myeloid origin.

In another embodiment, the compositions of the disclosure are employed to introduce nucleic acids, e.g. siRNA into primary cells.

In another embodiment, the compositions of the disclosure are employed to introduce nucleic acids, e.g. siRNA into non-adherent, suspension cells.

In another embodiment, the compositions of the disclosure are employed to deliver a wide array of nucleic acids including but not limited to siRNA, miRNAs, miRNA mimics and inhibitors, piRNAs, piRNA inhibitors, plasmids, antisense molecules, modified and unmodified nucleic acids, hybrid nucleic acids (e.g. DNA-RNA hybrids), and more. Importantly, the present disclosure can be used to deliver miRNAs, siRNAs, and piRNAs of the human genome implicated in diseases such as diabetes, Alzheimer's, and cancer, as well as those associated with the genomes of pathogens (e.g. pathogenic viruses), or host-encoded genes that play a role in pathogen entry, replication, packaging, release, or any other critical step in pathogen replication.

In another embodiment, the compositions of the disclosure are used to deliver collections of nucleic acids such as pools of siRNA targeting multiple sites on a single gene, pools of siRNA targeting multiple genes, pools of miRNA or piRNA mimics, pools of miRNA or piRNA inhibitors, and more. Alternatively, pools of miRNA mimics or miRNA inhibitors, particularly those that are related to a particular disease, can be simultaneously delivered using the compositions of the disclosure.

In another embodiment, the compositions of the disclosure are used to deliver one or more randomly selected nucleic acids e.g. siRNA.

In another embodiment, the compositions of the disclosure are used to deliver one or more nucleic acids that have been selected by rational design methods.

In another embodiment, the compositions of the disclosure are control molecules that, for instance, are incapable of entering RISC, or can cause toxicity, or are labeled and can be used to assess transfection efficiency.

In another embodiment, the compositions of the disclosure are used to deliver molecules that target a specific gene or set of genes for RNAi. For instance, the set of genes might include a set of siRNA that target e.g. the kinome, or GPCRs, or genes associated with membrane remodelling, or the drugable genome set, or an entire genome.

In another embodiment, the duplex oligonucleotide complexes of the disclosure (e.g., G4) and related methods are used for diagnostic applications, prophylactics, therapeutics, agricultural applications, veterinary applications, research tools, cosmetic applications, and more. In the case of therapeutics and prophylactics, the compositions of the disclosure (e.g., G4) can be used in the manufacture of a medicament in animals, preferably mammals, more preferably humans in the treatment of diseases. Dosages of medicaments manufactured in accordance with the present disclosure may vary from micrograms per kilogram to hundreds of milligrams per kilogram of a subject. As is known in the art, dosage will vary according to the mass of the mammal receiving the dose, the nature of the mammal receiving the dose, the severity of the disease or disorder, and the stability of the medicament in the serum of the subject, among other factors well known to persons of ordinary skill in the art. For these applications, an organism suspected of having a disease or disorder that is amenable to modulation by manipulation of a particular target nucleic acid of interest is treated by administering compositions of the disclosure. Results of the treatment may be ameliorative, palliative, prophylactic, and/or diagnostic of a particular disease or disorder.

Furthermore, in the case of therapeutic or prophylactic applications, the duplex oligonucleotide complexes of the disclosure (e.g., G4) can be combined with a variety of therapeutic compositions, delivery agents, and methods of administration. Pharmaceutically acceptable carriers, excipients, and diluents are known to persons skilled in the art. Methods of administration to cells and organisms are also known to persons skilled in the art. Dosing regimens, for example, are known to depend on the severity and degree of responsiveness of the disease or disorder to be treated, with a course of treatment spanning from days to months, or until the desired effect on the disorder or disease state is achieved. Chronic administration of molecules of the disclosure may be required for lasting desired effects with some diseases or disorders. Suitable dosing regimens can be determined by, for example, administering varying amounts of one or more molecules of the disclosure in a pharmaceutically acceptable carrier or diluent, by a pharmaceutically acceptable delivery route, and amount of drug accumulated in the body of the recipient organism can be determined at various times following administration. Similarly, the desired effect can be measured at various times following administration of the molecule(s) of the disclosure, and this data can be correlated with other pharmacokinetic data, such as body or organ accumulation. Those of ordinary skill can determine optimum dosages, dosing regimens, and the like. Those of ordinary skill may employ $EC_{50}$ data from in vivo and in vitro animal models as guides for human studies.

In another embodiment, the compositions and methods of the disclosure are used in combinational therapies, in particular, combinational therapies directed toward alleviating or minimizing the effects of human diseases including cancer, Alzheimer's and other neural diseases such as epilepsy, and more.

In another embodiment, the compositions and methods of the disclosure are employed in structure/function studies to design and test alternative targeting scaffolds.

Because the molecules of the disclosure act independent of the cell type or species into which they are introduced, in another embodiment the present disclosure is used to deliver nucleic acids to a broad range of organisms, including but not limited to plants, animals, protozoa, bacteria, viruses and fungi. The present disclosure is particularly advantageous for use in mammals such as cattle, horse, goats, pigs, sheep, canines, rodents such as hamsters, mice, and rats, and primates such as, gorillas, bush babies, chimpanzees, and humans.

In another embodiment, the compositions and methods of the disclosure can be used to target specific tissues, particularly diseased tissues including heart tissues, neural tissues, tissues of the gastrointestinal tract, muscle tissues, pulmonary tissues, cancerous tissues, tissues infected with pathogens, and more. The present disclosure may be used advantageously with diverse cell types, including but not limited to primary cells, germ cell lines and somatic cells. For example, the cell types may be embryonic cells, oocytes, sperm cells, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes and cells of the endocrine or exocrine glands.

In another embodiment, the compositions of the disclosure are delivered to e.g. a subject by intravenous, inhalation, intramuscular, dermal, sub-dermal, cutaneous, subcutaneous, intranasal, oral, rectal, by eye drops, by tissue implantation of a device that releases the molecule(s) at an advantageous location, such as near an organ or tissue or cell type harboring e.g. a target nucleic acid of interest, or other art recognized methods for introducing nucleic acids to a subject. The molecules of the disclosure can be administered in a cream or ointment topically, an oral preparation such as a capsule or tablet or suspension or solution, and the like.

Methods of Synthesizing Duplex Oligonucleotide Complexes

In another aspect, the disclosure provides methods for preparing duplex oligonucleotide complexes (e.g., G4). In one embodiment, chemical derivatives of the conjugate moiety are incorporated at the desired position in the oligonucleotide chain while still attached to the solid synthesis support. Preferably, this is accomplished using the same chemistry as that used to assemble the oligonucleotide (e.g., phosphoramidite, H-phosphonate, etc.) or by using a solid synthesis support comprising the desired conjugate moiety as the initiation site for assembly of the oligonucleotide. Alternatively, protected chemical functionalities may be incorporated into the oligonucleotide during its synthesis, deprotected at an appropriate point in the synthesis under conditions compatible with the oligonucleotide protecting groups and the linkage to the solid support, and then covalently reacted with a suitably activated form of the conjugate moiety.

In another embodiment, completed oligonucleotides are reacted following cleavage and deprotection with a suitable derivative of the conjugate moiety of interest. This reaction can either be non-specific, that is, the conjugate moiety can either covalently react randomly with sites on the oligonucleotide or interact non-covalently (e.g., through ionic interactions, hydrogen bonding, or hydrophobic interactions) with the oligonucleotide; or specific, if a particular chemical functionality has been incorporated in to the oligonucleotide for reaction with a suitably reactive derivative of the conjugate moiety. In this embodiment, duplexed oligonucleotides may be utilized in the conjugation reactions as well as single strands.

As described above, conjugate moieties can be attached to solid oligonucleotide synthesis supports to act as the initiation site for oligonucleotide synthesis. In one embodiment, a linker is appended to the conjugate moiety to provide functional sites for attachment to the support and for initiation of oligonucleotide synthesis. Preferably, as described above, these sites are hydroxyl groups; most preferably, they are a primary hydroxyl group and a secondary hydroxyl group, to allow them to be chemically distinguished during synthesis of the conjugate-modified solid support.

In one embodiment, a conjugate moiety is incorporated into an oligonucleotide at sites other than the 3'-end by employing a derivative of the conjugate moiety that utilizes the same chemistry for its incorporation as the chemistry used to assemble the oligonucleotide chain. For example, the conjugate derivative may be placed in a reagent position on the automated synthesis instrument that is unused by the four standard nucleotide monomers, and then programmed into the desired sequence at the appropriate position(s). The addition of the conjugate is thus treated the same way as the other monomers, except perhaps for adjustments to the solution concentration or coupling time as needed for maximum efficiency of incorporation. Since the most common oligonucleotide chemistry currently in practice today is the phosphoramidite method, preferably the derivative of the conjugate moiety is a phosphoramidite.

Linkers of the sort described in the previous sections can be used as the scaffold on which to build the requisite phosphoramidite derivatives of the conjugate moiety. Similarly, covalent bonds of the sort described in the previous sections can be used to bond the linker and the conjugate moiety. One hydroxyl group of the linker, preferably a primary hydroxyl group, is protected with a protecting group suitable for use in oligonucleotide synthesis (e.g., dimethoxytrityl or silyl), according to methods well understood by those of ordinary skill in the art. Another hydroxyl group, preferably a secondary hydroxyl group, is reacted with an appropriately protected chlorophosphine in the presence of a tertiary base, or with an appropriately protected phosphorodiamidite in the presence of a tetrazole, triazole or imidazole derivative, to product the desired phosphoramidite, according to methods well understood by those of ordinary skill in the art. Such linker-conjugate moiety phosphoramidite derivatives may be used to place the conjugate moiety a virtually any position in the oligonucleotide sequence that does not impair the resulting utility of the oligonucleotide conjugate in the desired application.

In another embodiment, the linker may be a nucleoside derivative, as described above.

In another embodiment, the site of conjugation is the 5'-end of the oligonucleotide and the linker has only the functional group for covalent bond formation with the conjugate moiety and a hydroxyl group for conversion into the phosphoramidite derivative. This is because the conjugation at the 5'-end is the final step in the assembly of the oligonucleotide; no further monomers are added past this point. As such, the following types of linkers, by way of example, may be used in this case (in addition to those previously described): ω-aminoalkanols, ω-hydroxyalkanols, ω-hydroxyalkane thiols, and ω-hydroxyalkyl carboxylic acids.

Whenever a range is given in the specification, for example, a temperature range, a time range, a percent sequence identity, a sequence complementarity range, a length range, or a composition or concentration range, all intermediate ranges and subranges, as well as all individual values included in the ranges given are intended to be included in the disclosure.

All patents and publications mentioned in the specification are indicative of the levels of skill of those skilled in the art to which the disclosure pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known and available in the art prior to Applicant's disclosure, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

All references cited in the present application are incorporated in their entirety herein by reference to the extent not inconsistent herewith.

EXAMPLES

The following Examples are intended to illustrate but not to limit the invention as described previously.

Example 1

General Preparation of an ω-amino-1,3-diol Linker Compound

In Examples 1-51, all raw materials and solvents are available from commercial sources or were prepared using methods well known to those of ordinary skill in the art. The products of all reactions in Examples 1-51 were analyzed and the structures confirmed by $^1$H NMR spectroscopy and ESI-TOF mass spectrometry.

FIG. 1 describes a general synthetic scheme for preparing a class of linkers based upon an ω-amino-1,3-diol. Those of ordinary skill in the art will realize that the particular methods and materials described subsequently could be varied to produce the same product compounds. A benzyloxycarbonyl-protected (Cbz) amino acid is treated with 2,2-dimethyl-1,3-dioxane-4,6-dione (Meldrum's acid), diethyl cyanophosphonate, and triethylamine in methylene chloride solution at ambient temperature for 12-18 hours followed by refluxing in methanol for 4 hours. The resulting Cbz-protected ω-amino-β-ketoester is then treated with excess lithium borohydride in tetrahydrofuran solution for at ambient temperature 12-18 hours. The resulting Cbz-protected ω-amino-1,3-diol is treated with 4,4'-dimethoxytritylchloride in pyridine solution at ambient temperature 12-18 hours. The resulting Cbz-protected 1-O-DMTr-ω-amino-1,3-diol is treated with hydrogen and palladium on carbon catalyst in methanol solution at ambient temperature 4-16 hours. The resulting product is a 1-O-DMTr-ω-amino-1,3-diol.

Figure 2A:
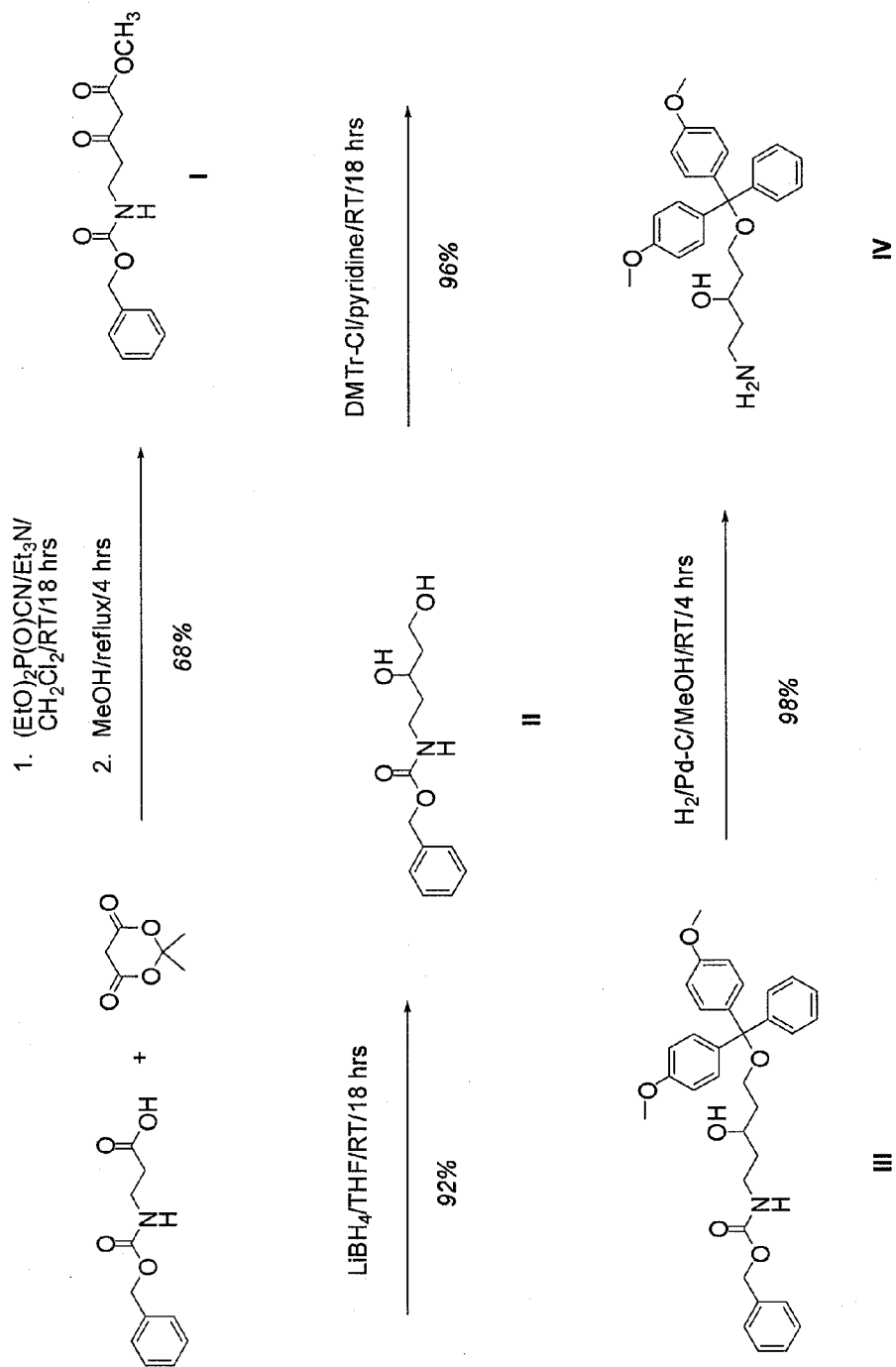
FIG. 2A is a synthetic scheme for the preparation of 1-amino-5-(bis(4-methoxyphenyl)(phenyl)methoxy)pentan-3-ol ("C5" linker).

The details of the preparation of 1-amino-5-(bis(4-methoxyphenyl)-(phenyl)methoxy)pentan-3-ol according to the above general scheme are given in the following Examples 2-5, and are illustrated in FIG. 2A.

Example 2

Preparation of methyl 5-(benzyloxycarbonylamino)-3-oxopentanoate (I)

3-(Benzyloxycarbonylamino)propanoic acid [N-Cbz-β-alanine] (5.0 g, 22.4 mmoles) is suspended in methylene chloride (100 mL) and 2,2-dimethyl-1,3-dioxane-4,6-dione (3.3 g, 22.9 mmoles), triethylamine (8.5 mL, 61.0 mmoles) and diethyl cyanophosphonate (3.7 mL, 22.8 mmoles) are added. All solids dissolve quickly, and the reaction quickly turns yellow. The solution is stirred for 16 hours at ambient temperature. The reaction mixture is then diluted with methylene chloride (100 mL) and carefully washed three times with aqueous hydrochloric acid (3 M, 50 mL each), three times with water (50 mL each) and once with saturated aqueous sodium chloride (50 mL). The reaction mixture is then dried over anhydrous sodium sulfate, filtered and evaporated to an orange syrup. The syrup is dissolved in anhydrous methanol (200 mL) and heated to reflux for 16 hours. The methanol is evaporated and the crude product purified on silica gel (150 mL bed volume) eluting with methylene chloride (500 mL) then methylene chloride:methanol (99.5:0.5 [v/v], 500 mL then 99:1 [v/v], 1000 mL). Fractions containing pure product by thin layer chromatography are pooled and evaporated to a pale yellow oil. The oil is dried well in vacuo. The yield is 4.5 g (68%).

Similarly, the following compounds are prepared:
i) Methyl 8-(benzyloxycarbonylamino)-3-oxooctanoate from 6-(Benzyloxycarbonyl-amino)-hexanoic acid.
ii) Methyl 10-(benzyloxycarbonylamino)-3-oxooctanoate from 8-(Benzyloxycarbonyl-amino)-octanoic acid.

iii) Methyl 14-(benzyloxycarbonylamino)-3-oxooctanoate from 10-(Benzyloxycarbonyl-amino)-decanoic acid.
iv) Methyl 3-(4-(benzyloxycarbonylamino)phenyl)-3-oxopropanoate from 4-(benzyloxy-carbonylamino)benzoic acid.
v) Benzyl 4-(3-methoxy-3-oxopropanoyl)piperidine-1-carboxylate from 1-(benzyloxy-carbonyl)piperidine-4-carboxylic acid.
vi) Benzyl 2-(3-methoxy-3-oxopropanoyl)pyrrolidine-1-carboxylate from 1-(benzyloxy-carbonyl)pyrrolidine-2-carboxylic acid.

Example 3

Preparation of benzyl 3,5-dihydroxypentylcarbamate (II)

Methyl 5-(benzyloxycarbonylamino)-3-oxopentanoate (4.5 g, 15.3 mmoles) is dissolved in anhydrous tetrahydrofuran (25 mL) and this solution is added slowly dropwise to an ice-cooled solution of lithium borohydride in anhydrous tetrahydrofuran (2 M, 25 mL, 50 mmoles). When the addition is complete, the cooling bath is removed and the reaction is stirred at ambient temperature for 16 hours. The clear, colorless solution is again cooled in an ice bath, and aqueous hydrochloric acid (1 M, 50 mL) is added slowly dropwise to decompose the excess reducing agent (gas is evolved). When a homogeneous solution is obtained, the mixture is concentrated to remove tetrahydrofuran. Ethyl acetate (100 mL) is added; the mixture is shaken well and poured into a separatory funnel. The layers are allowed to separate and the bottom aqueous layer is drawn off. The aqueous layer is then washed twice more with ethyl acetate (100 mL each), and the combined ethyl acetate solutions are washed with saturated aqueous sodium chloride (50 mL). The ethyl acetate solution is then dried over anhydrous sodium sulfate, filtered and evaporated to a pale brown syrup. The crude product is purified on silica gel (200 mL bed volume) eluting with ethyl acetate (500 mL) then ethyl acetate:methanol (99:1 [v/v], 500 mL then 95:5 [v/v], 1000 mL). Fractions containing pure product by thin layer chromatography are pooled and evaporated to a pale yellow oil. The oil is dried well in vacuo. The yield is 3.6 g (92%). The oil solidifies on standing at 4° C.

Similarly, the following compounds are prepared:
i) Benzyl 6,8-dihydroxyoctylcarbamate from methyl 8-(benzyloxycarbonylamino)-3-oxo-octanoate.
ii) Benzyl 8,10-dihydroxydodecylcarbamate from methyl 10-(benzyloxycarbonyl-amino)-3-oxo-octanoate.
iii) Benzyl 12,14-dihydroxytetradecylcarbamate from methyl 14-(benzyloxy-carbonylamino)-3-oxo-octanoate.
iv) Benzyl 4-(1,3-dihydroxypropyl)phenylcarbamate from methyl 3-(4-(benzyloxy-carbonylamino)phenyl)-3-oxopropanoate.
v) Benzyl 4-(1,3-dihydroxypropyl)piperidine-1-carboxylate from benzyl 4-(3-methoxy-3-oxopropanoyl)piperidine-1-carboxylate.
vi) Benzyl 2-(1,3-dihydroxypropyl)pyrrolidine-1-carboxylate from benzyl 2-(3-methoxy-3-oxopropanoyl)pyrrolidine-1-carboxylate.

Example 4

Preparation of benzyl 5-(bis(4-methoxyphenyl)(phenyl)methoxy)-3-hydroxy-pentylcarbamate (III)

Benzyl 3,5-dihydroxypentylcarbamate (7.3 g, 28.8 mmoles) is co-evaporated twice with anhydrous pyridine (100 mL each) and then is dissolved in anhydrous pyridine (300 mL). The solution is chilled in an ice bath, and 4,4'-dimethoxytritylchloride (9.8 g, 28.9 mmoles) is added. The reaction is allowed to warm to ambient temperature and is stirred for 16 hours. The yellow solution is then evaporated to near dryness, and the residue is dissolved in dry toluene (250 mL). The toluene mixture is chilled for 1 hour at 4° C., then filtered. The collected solid is washed with toluene (50 mL) and the combined toluene filtrates are evaporated to a dark yellow syrup. The syrup is dried in vacuo for at least 24 hours at ambient temperature. The crude product is purified on silica gel (500 mL bed volume) eluting with hexanes:ethyl acetate:triethylamine (90:5:5 [v/v/v], 300 mL, then 85:10:5 [v/v/v], 1000 mL, then 80:15:5 [v/v/v], 1000 mL, then 75:20:5 [v/v/v], 1000 mL, then 70:25:5 [v/v/v], 2000 mL, then 50:45:5 [v/v/v], 2000 mL). Fractions containing pure product by thin layer chromatography are pooled and evaporated to a pale yellow syrup. The syrup is dried well in vacuo. The yield is 15.4 g (96%).

Similarly, the following compounds are prepared:
i) Benzyl 8-(bis(4-methoxyphenyl)(phenyl)methoxy)-6-hydroxyoctylcarbamate from benzyl 6,8-dihydroxypentylcarbamate.
ii) Benzyl 10-(bis(4-methoxyphenyl)(phenyl)methoxy)-8-hydroxydodecylcarbamate from benzyl 8,10-dihydroxypentylcarbamate.
iii) Benzyl 14-(bis(4-methoxyphenyl)(phenyl)methoxy)-12-hydroxytetradecylcarbamate from benzyl 12,14-dihydroxypentylcarbamate.
iv) Benzyl 4-(3-(bis(4-methoxyphenyl)(phenyl)methoxy)-1-hydroxypropyl)phenyl-carbamate from benzyl 4-(1,3-dihydroxypropyl)phenylcarbamate.
v) Benzyl 4-(3-(bis(4-methoxyphenyl)(phenyl)methoxy)-1-hydroxypropyl)piperidine-1-carboxylate from benzyl 4-(1,3-dihydroxypropyl)piperidine-1-carboxylate.
vi) Benzyl 2-(3-(bis(4-methoxyphenyl)(phenyl)methoxy)-1-hydroxypropyl)pyrrolidine-1-carboxylate from benzyl 2-(1,3-dihydroxypropyl)pyrrolidine-1-carboxylate.

Example 5

Preparation of 1-amino-5-(bis(4-methoxyphenyl)(phenyl)methoxy)pentan-3-ol (IV)

Benzyl 5-(bis(4-methoxyphenyl)(phenyl)methoxy)-3-hydroxypentylcarbamate (15.4 g, 27.7 mmoles) is dissolved in methanol (250 mL) and the solution is poured into a hydrogenation flask. 10% Palladium on carbon (1.5 g, 50% water by weight) is added, and the flask is sealed. The atmosphere in the flask is evacuated using a diaphragm pump, and replaced with dry argon to 10 psi. This cycle of evacuation/argon purging is repeated four more times. The flask is then evacuated once more and filled with hydrogen to 30 psi. The suspension is stirred briskly at ambient temperature for 16 hours. Hydrogen is replaced to 30 psi as necessary during the first four hours of reaction. The flask is then evacuated to remove hydrogen, and refilled with argon to atmospheric pressure. The catalyst is removed by filtration using a 0.45 μm nylon membrane, and washed with methanol (100 mL). The combined methanol filtrates are evaporated to dryness to give a white glassy foam, which is further dried in vacuo. The yield is 11.4 g (98%).

Similarly, the following compounds are prepared:
i) 8-Amino-1-(bis(4-methoxyphenyl)(phenyl)methoxy)-octan-3-ol from benzyl 8-(bis(4-methoxyphenyl)(phenyl)methoxy)-6-hydroxyoctylcarbamate.

ii) 10-Amino-1-(bis(4-methoxyphenyl)(phenyl)methoxy)-dodecan-3-ol from benzyl 10-(bis(4-methoxyphenyl)(phenyl)methoxy)-8-hydroxydodecylcarbamate.

iii) 14-Amino-1-(bis(4-methoxyphenyl)(phenyl)methoxy)-tetradecan-3-ol from benzyl 14-(bis(4-methoxyphenyl)(phenyl)methoxy)-12-hydroxytetradecylcarbamate.

iv) 1-(4-Aminophenyl)-3-(bis(4-methoxyphenyl)(phenyl)methoxy)propan-1-ol from benzyl 4-(3-(bis(4-methoxyphenyl)(phenyl)methoxy)-1-hydroxypropyl)phenylcarbamate.

v) 3-(Bis(4-methoxyphenyl)(phenyl)methoxy)-1-(piperidin-4-yl)propan-1-ol from benzyl 4-(3-(bis(4-methoxyphenyl)(phenyl)methoxy)-1-hydroxypropyl)piperidine-1-carboxylate.

vi) 3-(Bis(4-methoxyphenyl)(phenyl)methoxy)-1-(pyrrolidin-2-yl)propan-1-ol from benzyl 2-(3-(bis(4-methoxyphenyl)(phenyl)methoxy)-1-hydroxypropyl)pyrrolidine-1-carboxylate.

Example 6

General Preparation of a Conjugate Moiety-ω-amino-1,3-diol Linker Compound

Covalent attachment of a conjugate moiety to an ω-amino-1,3-diol linker requires a derivative of the conjugate moiety that is reactive with the amine functionality on the linker. Suitable reactive derivatives include carboxylic acid anydrides, carboxylic acid chlorides, activated carboxylic acid esters such as N-hydroxysuccinimidyl, N-hydroxybenzotriazolyl, or pentafluorophenyl, chloroformates, 4-nitrophenyl carbonates and sulfonyl chlorides, to list a few Examples. Such reactive derivatives can be prepared and isolated as pure compounds, or can be prepared in situ immediately prior to use. In general, equivalent molar quantities of the reactive conjugate derivative and the aminated linker are dissolved together in an appropriate solvent and allowed to react at ambient temperature for 1 to 24 hours. Typical solvents depend on the solubility of the reagents and the type of reaction; for example, N,N-dimethylformamide is a useful solvent for the condensation of activated carboxylic acid esters with ω-amino-1,3-diol linkers, while pyridine is more appropriate for carboxylic acid anhydrides, chlorides or chloroformates where acid byproducts are produced.

Figure 2B:
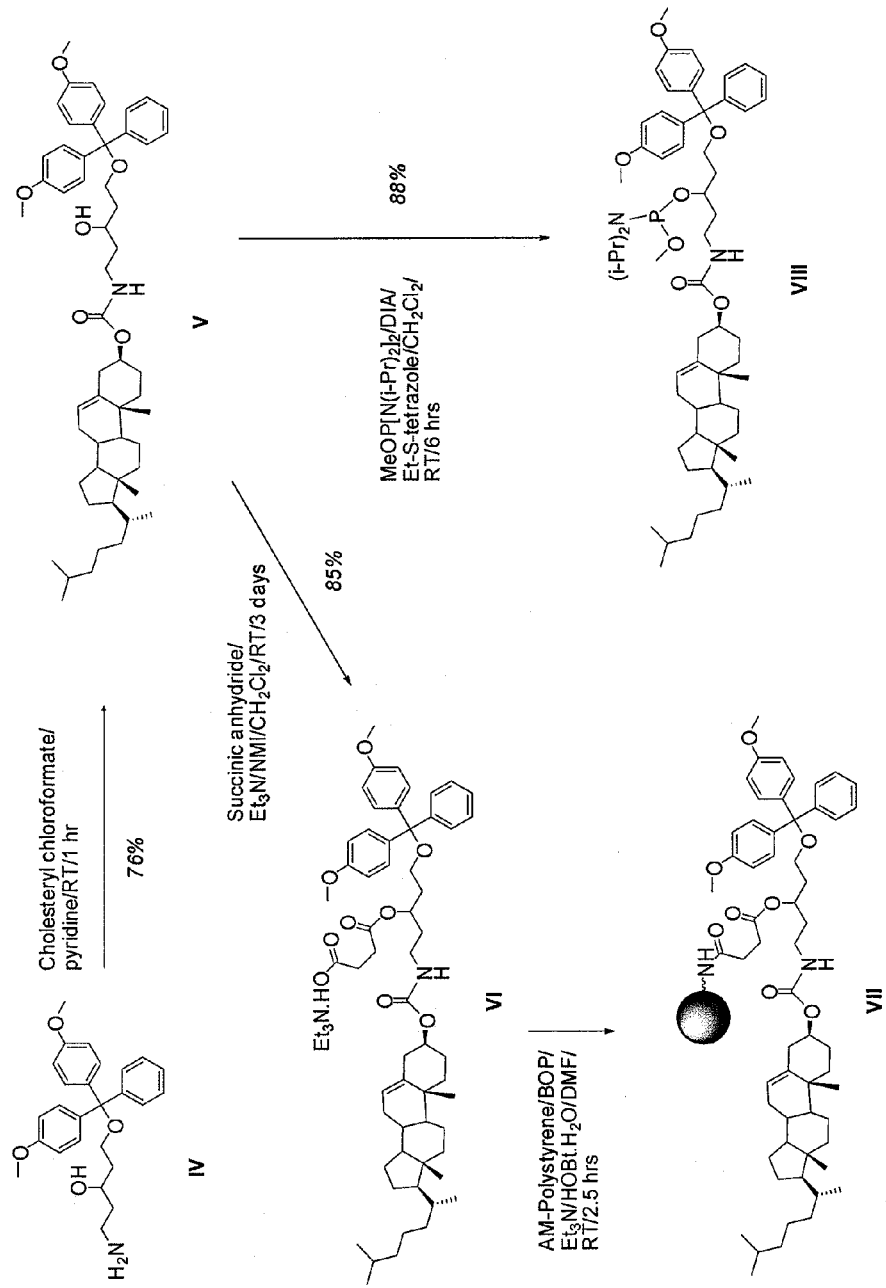
FIG. 2B is a synthetic scheme for the preparation of cholesteryl 5-(bis(4-methoxyphenyl)(phenyl) methoxy)-3-hydroxypentylcarbamate ("CHOL-C5"), a preferred embodiment of the present invention. Also, synthetic schemes for the preparation of a solid support and a phosphoramidite (cholesteryl 5-(bis(4-methoxyphenyl)-(phenyl)methoxy)-3-((diisopropylamino)(methoxy)phosphinooxy)pentylcarbamate) useful for oligonucleotide synthesis from CHOL-C5.

The details of the preparation of cholesteryl 5-(bis(4-methoxyphenyl)(phenyl)methoxy)-3-hydroxypentylcarbamate according to the above general scheme are given in the following Example 7, and are illustrated in FIG. 2B. In this case cholesterol is the conjugate moiety and cholesteryl chloroformate its reactive derivative. Examples 7-16 provide preparative details for steroidal conjugate moieties other than cholesterol.

Example 7

Preparation of cholesteryl 5-(bis(4-methoxyphenyl)(phenyl)methoxy)-3-hydroxypentylcarbamate (V)

1-amino-5-(bis(4-methoxyphenyl)(phenyl)methoxy)pentan-3-ol (4.3 g, 10.3 mmoles) is co-evaporated twice with anhydrous pyridine (50 mL each) and then is dissolved in anhydrous pyridine (70 mL). The solution is chilled in an ice bath, and cholesteryl chloroformate (4.8 g, 10.8 mmoles) in dry toluene (15 mL) is added slowly dropwise. The reaction is allowed to warm to ambient temperature and is stirred for 1 hour. Methanol (25 mL) is added, and the mixture is evaporated to near dryness. The residue is co-evaporated twice with dry toluene (50 mL each). The crude product is purified on silica gel (250 mL bed volume) eluting with hexanes:acetone:triethylamine (93:5:2 [v/v/v], 500 mL, then 88:10:2 [v/v/v], 1000 mL, then 78:20:2 [v/v/v], 1000 mL). Fractions containing pure product by thin layer chromatography are pooled and evaporated to a pale yellow resin. The resin is dried well in vacuo. The yield is 6.6 g (76%).

Similarly, the following compounds are prepared:

i) Cholesteryl 8-(bis(4-methoxyphenyl)(phenyl)methoxy)-6-hydroxyoctylcarbamate from 8-amino-1-(bis(4-methoxyphenyl)(phenyl)methoxy)-octan-3-ol and cholesteryl chloroformate in pyridine.

ii) Cholesteryl 10-(bis(4-methoxyphenyl)(phenyl)methoxy)-8-hydroxydodecylcarbamate from 10-amino-1-(bis(4-methoxyphenyl)(phenyl)methoxy)-dodecan-3-ol and cholesteryl chloroformate in pyridine.

iii) Cholesteryl 14-(bis(4-methoxyphenyl)(phenyl)methoxy)-12-hydroxytetradecylcarbamate from 14-amino-1-(bis(4-methoxyphenyl)(phenyl)methoxy)-octan-3-ol and cholesteryl chloroformate in pyridine.

iv) Cholesteryl 4-(3-(bis(4-methoxyphenyl)(phenyl)methoxy)-1-hydroxypropyl)phenylcarbam-ate from 1-(4-aminophenyl)-3-(bis(4-methoxyphenyl)(phenyl)methoxy)propan-1-ol and cholesteryl chloroformate in pyridine.

v) Cholesteryl 4-(3-(bis(4-methoxyphenyl)(phenyl)methoxy)-1-hydroxypropyl)piperidine-1-carboxylate from 3-(bis(4-methoxyphenyl)(phenyl)methoxy)-1-(piperidin-4-yl)propan-1-ol and cholesteryl chloroformate in pyridine.

vi) Cholesteryl 2-(3-(bis(4-methoxyphenyl)(phenyl)methoxy)-1-hydroxypropyl)pyrrolidine-1-carboxylate from 3-(bis(4-methoxyphenyl)(phenyl)methoxy)-1-(pyrrolidin-2-yl)propan-1-ol and cholesteryl chloroformate in pyridine.

vii) N-(8-(bis(4-methoxyphenyl)(phenyl)methoxy)-6-hydroxyoctyl)acetamide from 8-amino-1-(bis(4-methoxyphenyl)(phenyl)methoxy)-octan-3-ol and 4-nitrophenylacetate in N,N-dimethylformamide.

viii) Cholesteryl 6-(8-(bis(4-methoxyphenyl)(phenyl)methoxy)-6-hydroxyoctylamino)-6-oxo-hexylcarbamate from 8-amino-1-(bis(4-methoxyphenyl)(phenyl)methoxy)-octan-3-ol and 1H-benzo[d][1,2,3]triazol-1-yl 6-(benzyloxycarbonylamino)hexanoate in N,N-dimethylformamide. 1H-benzo[d][1,2,3]triazol-1-yl 6-(benzyloxycarbonylamino)hexanoate is prepared in situ from 6-(cholesteryloxycarbonylamino)hexanoic acid, 1-hydroxybenzotriazole hydrate and N,N' dicyclohexyl carbodiimide in N,N-dimethylformamide. 6-(Cholesteryloxycarbonylamino)-hexanoic acid is prepared from 6-aminohexanoic acid and cholesteryl chloroformate in pyridine.

ix) Cholesteryl 12-(8-(bis(4-methoxyphenyl)(phenyl)methoxy)-6-hydroxyoctylamino)-12-oxo-dodecylcarbamate from 8-amino-1-(bis(4-methoxyphenyl)(phenyl)methoxy)-octan-3-ol and 1H-benzo[d][1,2,3]triazol-1-yl 12-(cholesteryloxycarbonylamino)dodecanoate in N,N-dimethyl-formamide. 1H-benzo[d][1,2,3]triazol-1-yl12-(cholesteryloxycarbonylamino) dodecanoate is prepared in situ from 12-(cholesteryloxycarbonylamino) dodecanoic acid, 1-hydroxy-benzotriazole hydrate and N,N' dicyclohexylcarbodiimide in N,N-dimethylformamide. 12-(Cholesteryloxycarbonylamino)-dodecanoic acid is prepared from 12-aminododecanoic acid and cholesteryl chloroformate in pyridine.

Example 8

Preparation of 5α-cholestan-3β-ol 4-nitrophenyl carbonate

5α-cholestan-3β-ol (3.9 g, 10.0 mmoles) is co-evaporated with dry toluene (50 mL) and then is dissolved in dry toluene (100 mL). The solution is stirred at ambient temperature, and triethylamine (1.4 mL, 10.0 mmoles) is added, followed by 4-nitrophenyl chloroformate (2.0 g, 9.9 mmoles). The reaction mixture is stirred overnight, during which time a white precipitate of triethylammonium chloride forms. The mixture is evaporated to near dryness. The crude product is purified on silica gel (200 mL bed volume) eluting with hexanes:ethyl acetate (95:5 [v/v], 2000 mL). Fractions containing pure product by thin layer chromatography are pooled and evaporated to an amorphous white solid. The solid is dried well in vacuo. The yield is 3.5 g (63%).

Similarly, the following compounds are prepared:
i) Stigmasterol 4-nitrophenyl carbonate from stigmasterol and 4-nitrophenyl chloroformate and triethylamine in toluene.
ii) Ergosterol 4-nitrophenyl carbonate from ergosterol and 4-nitrophenyl chloroformate and triethylamine in toluene.
iii) Trans-androstenone 4-nitrophenyl carbonate from trans-adrosterone and 4-nitrophenyl chloroformate and triethylamine in ethyl acetate.
iv) Pregnenolone 4-nitrophenyl carbonate from pregnenolone and 4-nitrophenyl chloroformate and triethylamine in tetrahydrofuran. A catalytic quantity (10 mole percent) of N,N-dimethylaminopyridine was added to this reaction.
v) 5α-Androstan-3β-ol 4-nitrophenyl carbonate from 5α-androstan-3β-ol and 4-nitrophenyl chloroformate and triethylamine in toluene.
vi) 5α-Androstan-17β-ol 4-nitrophenyl carbonate from 5α-androstan-17β-ol and 4-nitrophenyl chloroformate and triethylamine in toluene.

Example 9

Preparation of 5α-cholestan-3β-yl 5-(bis(4-methoxyphenyl)(phenyl)methoxy)-3-hydroxypentylcarbamate 1-amino-5-(bis(4-methoxyphenyl)(phenyl)methoxy)pentan-3-ol (1.2 g, 2.8 mmoles) is dissolved in dry toluene (20 mL). The solution is stirred at room temperature, and triethylamine (0.4 mL, 2.9 mmoles) is added, followed by a solution of 5α-cholestan-3β-ol 4-nitrophenyl carbonate (1.6 g, 2.8 mmoles) in toluene (25 mL). The reaction is stirred at ambient temperature overnight. The mixture is evaporated to near dryness to give a yellow glassy foam. The crude product is purified on silica gel (150 mL bed volume) eluting with hexanes:ethyl acetate:triethylamine (80:20:2 [v/v/v], 700 mL, then 70:30:2 [v/v/v], 1000 mL). Fractions containing pure product by thin layer chromatography are pooled and evaporated to a white glassy foam. The foam is dried well in vacuo. The yield is 2.0 g (87%).

Similarly, the following compounds are prepared:
i) Stigmasteryl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and stigmasterol 4-nitrophenyl carbonate in toluene and triethylamine.
ii) Ergosteryl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and ergosterol 4-nitrophenyl carbonate in toluene and triethylamine.
iii) Trans-androsteronyl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and trans-androsterone 4-nitrophenyl carbonate in toluene and triethylamine.
iv) Pregnenolonyl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and pregnenolone 4-nitrophenyl carbonate in toluene and triethylamine.
v) 5α-Androstan-3β-yl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and 5α-androstan-3β-ol 4-nitrophenyl carbonate in toluene and triethylamine.
v) 5α-Androstan-17β-yl 5-(bis(4-methoxyphenyl)(phenyl)methoxy)-3-hydroxypentylcarbamate from 1-amino-5-(bis(4-methoxyphenyl)(phenyl)methoxy)-pentan-3-ol and 5α-androstan-17β-ol 4-nitrophenyl carbonate in toluene and triethylamine.

Example 10

Preparation of Cholanic Acid 4-nitrophenyl Ester

Cholanic acid (3.6 g, 10.0 mmoles) is suspended in methylene chloride (200 mL) and stirred well at ambient temperature. 4-Nitrophenol (1.4 g, 10.1 mmoles) and N,N'-dicylcohexylcarbodiimide (2.1 g, 10.2 mmoles) are added, and the mixture is stirred overnight. The mixture is then filtered, the solid washed with a little methylene chloride, and the filtrate is evaporated to dryness to give a yellow solid. The crude product is dissolved in ethyl acetate (100 mL). The solution is filtered and the filtrate si evaporated to give an off-white solid. The solid is crystallized from hot hexanes. The yield is 3.9 g (80%).

Example 11

Preparation of cholanyl 5-(bis(4-methoxyphenyl)(phenyl)methoxy)-3-hydroxypentylamide 1-amino-5-(bis(4-methoxyphenyl)(phenyl)methoxy)pentan-3-ol (1.2 g, 2.8 mmoles) is dissolved in dry toluene (20 mL). The solution is stirred at room temperature, and triethylamine (0.4 mL, 2.9 mmoles) is added, followed by a solution of cholanic acid 4-nitrophenyl ester (1.4 g, 2.9 mmoles) in toluene (25 mL). The reaction is stirred at ambient temperature overnight. The mixture is evaporated to near dryness to give a yellow syrup. The crude product is purified on silica gel (200 mL bed volume) eluting with hexanes:ethyl acetate:triethylamine (60:40:2 [v/v/v], 1500 mL). Fractions containing pure product by thin layer chromatography are pooled and evaporated to a pale yellow glassy foam. The foam is dried well in vacuo. The yield is 1.7 g (80%).

Example 12

Preparation of 3-O-acetyl-lithocholic acid

Lithocholic acid (5.5 g, 14.6 mmoles) is suspended in acetic anhydride (55 mL) and the mixture is stirred overnight while heating at 90-95° C. During this period, all solid dissolves. The mixture is then cooled to ambient temperature and evaporated to dryness to give a white solid. The solid is crystallized from hot methanol. The yield is 4.3 g. Approximately 35% of the solid obtained is 3'-O-acetyl-lithocholic acid methyl ester, presumably arising from some 3'-O-acetyl-lithocholic-acetic mixed anhydride in the crude product during the crystallization from methanol. This mixed product was carried forward in subsequent reactions without additional purification.

Example 13

3'-O-acetyl-lithocholic acid 4-nitrophenyl ester

The mixed product from Example 12 (4.3 g) is dissolved in methylene chloride (100 mL) and the solution is stirred at ambient temperature. 4-Nitrophenol (1.4 g, 10.1 mmoles) and N,N'-dicylcohexylcarbodiimide (2.1 g, 10.2 mmoles) are added, and the mixture is stirred overnight. The mixture is then filtered, the solid washed with a little methylene chloride, and the filtrate is evaporated to dryness to give a yellow syrup. The crude product is purified on silica gel (200 mL bed volume) eluting with hexanes:ethyl acetate (90:10 [v/v], 1500 mL). Fractions containing pure product by thin layer chromatography are pooled and evaporated to a white solid. The solid is crystallized from hot acetonitrile. The yield is 3.9 g. The product is a 70:30 (mole:mole) mixture of the desired 4-nitrophenyl ester and the methyl ester, and is carried forward in subsequent reactions without further purification.

Example 14

Preparation of 3-O-acetyl-lithocholyl 5-(bis(4-methoxyphenyl)(phenyl)methoxy)-3-hydroxypentylamide 1-amino-5-(bis(4-methoxyphenyl)(phenyl)methoxy)pentan-3-ol (1.0 g, 2.4 mmoles) is dissolved in dry toluene (20 mL). The solution is stirred at room temperature, and triethylamine (0.4 mL, 2.9 mmoles) is added, followed by a solution of 3-O-acetyl lithocholic acid 4-nitrophenyl ester (product of Example 13, 1.8 g, 2.4 mmoles) in toluene (25 mL). The reaction is stirred at ambient temperature overnight. The mixture is evaporated to near dryness to give a yellow syrup. The crude product is purified on silica gel (200 mL bed volume) eluting with hexanes:ethyl acetate:triethylamine (60:40:2 [v/v/v], 600 mL, then 50:50:2 [v/v/v], 1500 mL). Fractions containing pure product by thin layer chromatography are pooled and evaporated to a white glassy foam. The foam is dried well in vacuo. The yield is 1.4 g (71%).

Example 15

Preparation of Lithocholic Acid Methyl Amide

3'-O-acetyl-lithocholic acid 4-nitrophenyl ester (product of Example 13, 2.0 g) is suspended in cold 33% [w/v] methylamine:ethanol, and methylene chloride (20 mL) is added. The reaction flask is tightly stoppered, and the reaction mixture is allowed to stir at ambient temperature for three days. The yellow solution thus obtained is evaporated to dryness, and the residue is partitioned between methylene chloride (300 mL) and 1 M aqueous sodium hydroxide (200 mL). The layers are separated, and the methylene chloride solution is washed with additional 1 M aqueous sodium hydroxide (200 mL), followed by saturated aqueous sodium chloride (200 mL). The methylene chloride solution is dried over anhydrous sodium sulfate, filtered and evaporated to a pale yellow foam. $^1$H NMR (CDCl$_3$) indicates that the acetyl group is incompletely removed, so that the crude product is dissolved in chloroform (30 mL) and methanol (10 mL), and 10 M aqueous sodium hydroxide (1 mL) is added. The mixture is stirred for 4 hours at ambient temperature, after which time glacial acetic acid is added (1 mL) followed by ethyl acetate (50 mL). The solution is washed three times with water (50 mL each time), dried over anhydrous sodium sulfate, filtered, and evaporated to a white solid. The yield is 1.9 g. It should be noted that the treatment with methylamine in ethanol smoothly converted not only the 4-nitrophenyl ester, but also the methyl ester, to the methyl amide.

Example 16

Preparation of Lithocholic Acid Methyl Amide 4-nitrophenyl Carbonate

Lithocholic acid methyl amide (1.4 g, 3.6 mmoles) is co-evaporated with dry toluene (50 mL) and then is dissolved in dry toluene (50 mL) and chloroform (50 mL). The solution is stirred at ambient temperature, and triethylamine (0.6 mL, 4.3 mmoles) is added, followed by 4-nitrophenyl chloroformate (0.7 g, 3.5 mmoles). The reaction mixture is stirred overnight. Thin layer chromatography (1:1 [v/v] methylene chloride:ethyl acetate) indicates the reaction is incomplete, so additional triethylamine (0.6 mL, 4.3 mmoles) and 4-nitrophenyl chloroformate (0.7 g) are added, and the reaction is allowed to proceed for two days more. The mixture is evaporated to near dryness. The crude product is purified on silica gel (200 mL bed volume) eluting with methylene chloride (500 mL) then methylene chloride:ethyl acetate (3:1 [v/v], 1000 mL). Fractions containing pure product by thin layer chromatography are pooled and evaporated to an amorphous white solid. The solid is dried well in vacuo. The yield is 1.7 g (85%).

Example 17

Preparation of lithocholic acid methyl amide 5-(bis (4-methoxyphenyl)(phenyl)methoxy)-3-hydroxypentylcarbamate 1-amino-5-(bis(4-methoxyphenyl)(phenyl)methoxy)pentan-3-ol (1.2 g, 2.8 mmoles) is dissolved in dry toluene (20 mL). The solution is stirred at room temperature, and triethylamine (0.4 mL, 2.9 mmoles) is added, followed by lithocholic acid methyl amide 4-nitrophenyl carbonate (1.4 g, 2.9 mmoles) and toluene (25 mL). The reaction is stirred at ambient temperature for three days. The mixture is evaporated to near dryness to give a yellow syrup. The crude product is purified on silica gel (200 mL bed volume) eluting with methylene chloride:triethylamine (100:2 [v/v], 500 mL) then methylene chloride:ethyl acetate:triethylamine (80:20:2 [v/v/v], 1000 mL). Fractions containing pure product by thin layer chromatography are pooled and evaporated to a white glassy foam. The foam is dried well in vacuo. The yield is 2.5 g. NMR (CDCl$_3$) indicates the product is contaminated with about 25% (mole:mole) of starting lithocholic acid methyl amide 4-nitrophenyl carbonate. The mixture is carried forward in subsequent steps without further purification.

For additional clarity and ease of discussion in subsequent sections, Table I presents the structures of the above compounds and the abbreviated nomenclature associated therewith.

Example 18

General Preparation of a Conjugate moiety-ω-amino-1,3-diol Linker Compound Attached to a Solid Support Useful for Oligonucleotide Synthesis A conjugate moiety-ω-amino-1,3-diol linker compound may be attached to a solid synthesis support by providing a molecular tether between the compound and the support. As described previously, the most common tethers are dicarboxylic acids. For dicarboxylic acids that form cyclic anhydrides, approximately equivalent molar quantities of the conjugate moiety-ω-amino-1,3-diol linker compound and the cyclic anhydride are dissolved in methylene chloride containing triethylamine and 1-methylimidazole. The solution is stirred at ambient temperature for 12 hours to several days. For dicarboxylic acids that do not form cyclic anhydrides, the dicarboxylic acid is first activated with a carbodiimide reagent and then reacted in slight molar excess with the conjugate moiety-ω-amino-1,3-diol linker compound in the presence of a catalytic quantity of N,N-dimethylaminopyridine at ambient temperature for 12 hours to several days. In either case, the conjugate moiety-ω-amino-1,3-diol linker compound comprising a dicarboxylic acid tether is isolated as its triethylamine salt following chromatography.

The conjugate moiety-ω-amino-1,3-diol linker compound comprising a dicarboxylic acid tether is then attached to the solid synthesis support. Typical solid supports for oligonucleotide synthesis are either amine-functionalized controlled pore glass or cross-linked aminomethyl polystyrene. The free carboxylic acid moiety is activated using any of several carboxylic acid activating reagents corn conjugate moiety-ω-amino-1,3-diol linker compound inium hexafluorophosphate [HBTU] or benzotriazol-1-yl-oxy-tris(dimethylamino)phosphonium hexafluorophosphate [BOP], in N,N-dimethylformamide solution in the presence of a tertiary amine and 1-hydroxybenzotriazole hydrate. An aliquot of the activated carboxylic acid solution is added to a suspension of the solid synthesis support in N,N-dimethylformamide and the mixture shaken at ambient temperature for 1-2 hours. The quantity of the conjugate moiety-ω-amino-1,3-diol linker compound comprising a dicarboxylic acid tether attached to the solid support (the "loading") is then assayed by washing a small sample of the support with appropriate solvents, treating the sample with anhydrous acid solution (for example, 3% [v/v] dichloroacetic acid in methylene chloride) to remove the DMTr-protecting group, measuring the absorbance at 498 nm of the obtained acid solution, and calculating the quantity of DMTr-cation present using Beer's Law and a molar extinction coefficient of 70,000 $M^{-1}cm^{-1}$. This analytical procedure is well known to those of ordinary skill in the art. Additional aliquots of the activated carboxylic acid solution are added as necessary to the solid support until the desired loading is obtained. Typical loadings are from about 5 to about 35 μmoles of conjugate moiety-ω-amino-1,3-diol linker compound per gram of solid support.

The details of the preparation of 4-(1-(cholesteryloxycarbonylamino)-5-(bis(4-methoxyphenyl)-(phenyl)methoxy)pentan-3-yloxy)-4-oxobutanoic acid attached to a solid polystyrene support according to the above general scheme are given in the following Examples 19 and 20, and are illustrated in FIG. 2B. In this case the dicarboxylic acid tether is succinic acid.

Example 19

Preparation of 4-(1-(cholesteryloxycarbonylamino)-5-(bis(4-methoxyphenyl)-(phenyl)methoxy)pentan-3-yloxy)-4-oxobutanoic acid triethylamine salt (VI)

Cholesteryl 5-(bis(4-methoxyphenyl)(phenyl)methoxy)-3-hydroxypentylcarbamate (6.6 g, 7.9 mmoles), succinic anhydride (0.8 g, 8.0 mmoles), triethylamine (3.3 mL, 23.7 mmoles) and 1-methylimidazole (0.3 mL, 3.9 mmoles) are dissolved in methylene chloride (60 mL). The reaction is stirred at ambient temperature for three days, during which time the solution darkened. The solution is then diluted with methylene chloride (100 mL) and washed twice with ice-cold aqueous citric acid (10% [w/v], 50 mL) and once with saturated aqueous sodium chloride (50 mL). The methylene chloride solution is dried over anhydrous sodium sulfate, filtered and evaporated to a dark resin. The crude product is purified on silica gel (175 mL bed volume) eluting with methylene chloride:triethylamine (95:5 [v/v], 1000 mL), then methylene chloride:methanol:triethylamine (90:5:5 [v/v/v], 1000 mL). Fractions containing pure product by thin layer chromatography are pooled and evaporated to a pale yellow resin. The resin is dried well in vacuo to give an off-white glassy foam. The yield is 6.3 g (85%).

Similarly, the following compounds are prepared:
i) 4-(8-(Cholesteryloxycarbonylamino)-1-(bis(4-methoxyphenyl)-(phenyl)methoxy)octan-3-yloxy)-4-oxobutanoic acid triethylamine salt from cholesteryl 8-(bis(4-methoxyphenyl)(phenyl)methoxy)-6-hydroxyoctylcarbamate.
ii) 4-(10-(Cholesteryloxycarbonylamino)-1-(bis(4-methoxyphenyl)-(phenyl)methoxy)octan-3-yloxy)-4-oxobutanoic acid triethylamine salt from cholesteryl 10-(bis(4-methoxyphenyl)(phenyl)methoxy)-8-hydroxydodecylcarbamate.
iii) 4-(14-(Cholesteryloxycarbonylamino)-1-(bis(4-methoxyphenyl)-(phenyl)methoxy)octan-3-yloxy)-4-oxobutanoic acid triethylamine salt from cholesteryl 14-(bis(4-methoxyphenyl)(phenyl)methoxy)-12-hydroxytetradecylcarbamate
iv) 4-(1-(4-(Cholesteryloxycarbonylamino)phenyl)-3-(bis(4-methoxyphenyl)(phenyl)methoxy)-propoxy)-4-oxobutanoic acid triethylamine salt from cholesteryl 4-(3-(bis(4-methoxy-phenyl)(phenyl)methoxy)-1-hydroxypropyl) phenylcarbamate.
v) 4-(1-(1-(Cholesteryloxycarbonyl)piperidin-4-yl)-3-(bis(4-methoxyphenyl)(phenyl)methoxy)-propoxy)-4-oxobutanoic acid triethylamine salt from cholesteryl 4-(3-(bis(4-methoxy-phenyl)(phenyl)methoxy)-1-hydroxypropyl) piperidine-1-carboxylate.
vi) 4-(1-(1-(Cholesteryloxycarbonyl)pyrrolidin-2-yl)-3-(bis(4-methoxyphenyl)(phenyl)-methoxy)propoxy)-4-oxobutanoic acid triethylamine salt from cholesteryl 2-(3-(bis(4-methoxy-phenyl)(phenyl)methoxy)-1-hydroxypropyl) pyrrolidine-1-carboxylate.
vii) 4-(8-Acetamido-1-(bis(4-methoxyphenyl)(phenyl)methoxy)octan-3-yloxy)-4-oxobutanoic acid triethylamine salt from N-(8-(bis(4-methoxyphenyl)(phenyl)methoxy)-6-hydroxyoctyl)-acetamide.
viii) 4-(8-((6-Cholesteryloxycarbonyl)aminohexanamido)-1-(bis(4-methoxyphenyl)(phenyl)-methoxy)octan-3-yloxy)-4-oxobutanoic acid triethylamine salt from cholesteryl 6-(8-(bis(4-methoxyphenyl)(phenyl)methoxy)-6-hydroxyoctylamino)-6-oxo-hexylcarbamate.
ix) 4-(8-((12-Cholesteryloxycarbonyl)aminododecanamido)-1-(bis(4-methoxyphenyl)(phenyl)-methoxy)octan-3-yloxy)-4-oxobutanoic acid triethylamine salt from cholesteryl 12-(8-(bis(4-methoxyphenyl)(phenyl)methoxy)-6-hydroxyoctylamino)-12-oxododecyl-carbamate.

Example 20

Preparation of 4-(1-(cholesteryloxycarbonylamino)-5-(bis(4-methoxyphenyl)-(phenyl)methoxy)pentan-3-yloxy)-4-oxobutanoic acid attached to cross-linked aminomethyl-polystyrene (VII)

AM-Polystyrene (5.0 g, ~33 μmoles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(1-(cholesteryloxycarbonylamino)-5-(bis(4-methoxyphenyl)-(phenyl)methoxy)pentan-3-yloxy)-4-oxobutanoic acid triethylamine salt (105 mg, 113 µmoles), dry, amine-free N,N-dimethylformamide (25.0 mL), triethylamine (31 µL, 225.0 µmoles), 1-hydroxybenzotriazole hydrate (18 mg, 117.5 µmoles) and BOP (55 mg, 124 µmoles). The mixture is shaken well until all solids dissolve and then allowed to sit for five minutes at ambient temperature to activate the carboxylic acid. An aliquot of the activated carboxylic acid solution (16.7 mL, 75.4 µmoles) is added via syringe to the shaking solid support suspension. The mixture is shaken for 1.5 hours and a 40 mg aliquot of the solid is then removed and a loading of 11.0 µmoles/gram determined using the method outlined above. An additional aliquot of activated carboxylic acid (4.5 mL, 20.3 µmoles) is added and the suspension shaken for another hour. A loading of 14.5 µmoles/gram is determined. The solid suspension is poured into a coarse fitted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fitted glass funnel and the liquid drained under vacuum. The solid is then washed well with acetonitrile (500 mL) and dried overnight in vacuo.

Solid supports having the compounds listed in Example 19 (i)-(ix) attached and loadings of approximately 15.0±1.0 µmoles/gram are prepared similarly.

The details of the preparation of 4-(1-(cholestanyloxycarbonylamino)-5-((bis(4-methoxyphenyl)-(phenyl)methoxy)pentan-3-yloxy)-2-oxoethoxy)acetic acid attached to a solid polystyrene support according to the above general scheme are given in the following Examples 21 and 22. In this case the dicarboxylic acid tether is diglycolic acid.

Example 21

Preparation of 4-(1-(cholestanyloxycarbonylamino)-5-((bis(4-methoxyphenyl)-(phenyl)methoxy)pentan-3-yloxy)-2-oxoethoxy)acetic acid triethylamine salt Cholestanyl 5-(bis(4-methoxyphenyl)(phenyl)methoxy)-3-hydroxypentylcarbamate (2.0 g, 2.4 mmoles), diglycolic anhydride (0.4 g, 3.6 mmoles), triethylamine (1.0 mL, 7.2 mmoles) and 1-methylimidazole (0.2 mL, 2.4 mmoles) are dissolved in methylene chloride (25 mL). The reaction is stirred at ambient temperature for three days, during which time the solution darkened. The solution is then diluted with methylene chloride (200 mL) and washed with 5% (w/v) aqueous dipotassium phosphate (50 mL). The methylene chloride solution is dried over anhydrous sodium sulfate, filtered and evaporated to a brown syrup. The crude product is purified on silica gel (100 mL bed volume) eluting with methylene chloride:triethylamine (95:5 [v/v], 400 mL), then methylene chloride:methanol:triethylamine (93:2:5 [v/v/v], 1000 mL). Fractions containing pure product by thin layer chromatography are pooled and evaporated to a pale tan glassy foam. The foam is dried well in vacuo. The yield is 2.0 g (79%).

Similarly, the following compounds are prepared:
i) 4-(1-(cholesteryloxycarbonylamino)-5-((bis(4-methoxyphenyl)-(phenyl)methoxy)pentan-3-yloxy)-2-oxoethoxy)acetic acid triethylamine salt from cholesteryl 5-(bis(4-methoxyphenyl)(phenyl)methoxy)-3-hydroxypentylcarbamate.
ii) 4-(1-(stigmasteryloxycarbonylamino)-5-((bis(4-methoxyphenyl)-(phenyl)methoxy)pentan-3-yloxy)-2-oxoethoxy)acetic acid triethylamine salt from stirmasteryl 5-(bis(4-methoxyphenyl)(phenyl)methoxy)-3-hydroxypentylcarbamate.
iii) 4-(1-(ergosteryloxycarbonylamino)-5-((bis(4-methoxyphenyl)-(phenyl)methoxy)pentan-3-yloxy)-2-oxoethoxy)acetic acid triethylamine salt from ergosteryl 5-(bis(4-methoxyphenyl)(phenyl)methoxy)-3-hydroxypentylcarbamate.
iv) 4-(1-(trans-androsteronyloxycarbonylamino)-5-((bis(4-methoxyphenyl)-(phenyl)methoxy)-pentan-3-yloxy)-2-oxoethoxy)acetic acid triethylamine salt from trans-androsteronyl5-(bis(4-methoxyphenyl)(phenyl)methoxy)-3-hydroxypentylcarbamate.
v) 4-(1-(pregnenolonyloxycarbonylamino)-5-((bis(4-methoxyphenyl)-(phenyl)methoxy)pentan-3-yloxy)-2-oxoethoxy)acetic acid triethylamine salt from pregnenolonyl 5-(bis(4-methoxyphenyl)(phenyl)methoxy)-3-hydroxypentylcarbamate.
vi) 4-(1-(5α-androstan-3β-yloxycarbonylamino)-5-((bis(4-methoxyphenyl)-(phenyl)methoxy)-pentan-3-yloxy)-2-oxoethoxy)acetic acid triethylamine salt from 5α-androstan-3β-yl 5-(bis(4-methoxyphenyl)(phenyl)methoxy)-3-hydroxypentylcarbamate.
vii) 4-(1-(5α-androstan-17β-yloxycarbonylamino)-5-((bis(4-methoxyphenyl)-(phenyl)methoxy)-pentan-3-yloxy)-2-oxoethoxy)acetic acid triethylamine salt from 5α-androstan-17β-yl 5-(bis(4-methoxyphenyl)(phenyl)methoxy)-3-hydroxypentylcarbamate.
viii) 4-(1-(cholanylamido)-5-((bis(4-methoxyphenyl)-(phenyl)methoxy)pentan-3-yloxy)-2-oxoethoxy)acetic acid triethylamine salt from cholanyl 5-(bis(4-methoxyphenyl)(phenyl)methoxy)-3-hydroxypentylamide.
ix) 4-(1-(3-O-acetyllithocholylamido)-5-((bis(4-methoxyphenyl)-(phenyl)methoxy)pentan-3-yloxy)-2-oxoethoxy)acetic acid triethylamine salt from 3-O-acetyl-lithocholyl 5-(bis(4-methoxyphenyl)(phenyl)methoxy)-3-hydroxypentylamide.
x) 4-(1-N-methylamidolithocholylamido)-5-((bis(4-methoxyphenyl)-(phenyl)methoxy)pentan-3-yloxy)-2-oxoethoxy)acetic acid triethylamine salt from lithocholic acid methyl amide 5-(bis(4-methoxyphenyl)(phenyl)methoxy)-3-hydroxypentylcarbamate.

Example 22

Preparation of 4-(1-(cholestanyloxycarbonylamino)-5-(bis(4-methoxyphenyl)-(phenyl)methoxy)pentan-3-yloxy)-2-oxoethoxy)acetic acid attached to cross-linked aminomethyl-polystyrene AM-Polystyrene (5.0 g, ~33 moles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(1-(cholestanyloxycarbonylamino)-5-((bis(4-methoxyphenyl)-(phenyl)methoxy)pentan-3-yloxy)-2-oxoethoxy)acetic acid triethylamine salt (50 mg, 50 moles), dry, amine-free N,N-dimethylformamide (12.5 mL), triethylamine (10 µL, 90 moles), 1-hydroxybenzotriazole hydrate (10 mg, 50 moles) and BOP (20 mg, 50 moles). The mixture is shaken well until all solids dissolve and then allowed to sit for five minutes at ambient temperature to activate the carboxylic acid. An aliquot of the activated carboxylic acid solution (9.0 mL, 36 mmoles) is added via syringe to the shaking solid support suspension. The mixture is shaken for 1.5 hours and a 40 mg aliquot of the solid is then removed and a loading of 5.2 mmoles/gram determined using the method outlined above. An additional aliquot of activated carboxylic acid (1.3 mL, 5.2 µmoles) is added and the suspension shaken for another hour. A loading of 6.0 moles/gram is determined. The solid suspension is poured into a coarse fritted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fritted glass funnel and the liquid drained under vacuum. The solid is then washed well with acetonitrile (500 mL) and dried overnight in vacuo.

Solid supports having the compounds listed in Example 21 (i)-(x) attached and loadings of approximately 6.0±0.5 mmoles/gram are prepared similarly.

Example 23

General Preparation of a Conjugate moiety-ω-amino-1,3-diol Linker Compound Phosphoramidite A conjugate moiety-ω-amino-1,3-diol linker compound may be converted into a phosphoramidite derivative using methods well known to those of ordinary skill in the art.

The details of the preparation of cholesteryl 5-(bis(4-methoxyphenyl)(phenyl)methoxy)-3-((diisopropylamino)(methoxy)phosphinooxy)pentylcarbamate according to the above general scheme are given in the following Example 24, and are illustrated in FIG. 2B.

Example 24

Preparation of cholesteryl 5-(bis(4-methoxyphenyl) (phenyl)methoxy)-3-((diisopropylamino)(methoxy) phosphinooxy)pentylcarbamate (VIII)

Cholesteryl 5-(bis(4-methoxyphenyl)(phenyl)methoxy)-3-hydroxypentylcarbamate (1.3 g, 1.6 mmoles) is dissolved in dry methylene chloride (3.2 mL) containing N,N-diisopropylamine (224 µL, 1.6 mmoles). The solution is stirred at ambient temperature. In a separate flask, methyl N,N,N',N'-tetraisopropylphosphorodiamidite (0.6 g, 2.4 mmoles) is dissolved in a mixture of methylene chloride (3.2 mL), N,N-diisopropylamine (224 µL, 1.6 mmoles), and 5-ethylthio-1H-tetrazole in acetonitrile (0.5 M, 1.6 mL, 0.8 mmoles). This solution is stirred at ambient temperature for 5 minutes, then added in one portion to the first solution. The mixture is stirred for 6 hours. Methanol (5 mL) is added, and the solution is evaporated to a thick syrup. The crude product is purified on silica gel (75 mL bed volume) eluting with hexanes:acetone: triethylamine (95:5:2 [v/v/v], 500 mL). Fractions containing pure product by thin layer chromatography are pooled and evaporated to a clear colorless syrup. The syrup is co-evaporated twice with toluene (50 mL each). The resulting white glassy foam is dried well in vacuo. The yield is 1.4 g (88%).

Example 25

General Preparation of a Conjugate moiety-ω-amino-alcohol Linker Compound

Covalent attachment of a conjugate moiety to an ω-amino-alcohol linker requires a derivative of the conjugate moiety that is reactive with the amine functionality on the linker. Suitable reactive derivatives include carboxylic acid anydrides, carboxylic acid chlorides, activated carboxylic acid esters such as N-hydroxysuccinimidyl, N-hydroxybenzotriazolyl, or pentafluorophenyl, chloroformates, 4-nitrophenyl carbonates and sulfonyl chlorides, to list a few Examples. Such reactive derivatives can be prepared and isolated as pure compounds, or can be prepared in situ immediately prior to use. In general, equivalent molar quantities of the reactive conjugate derivative and the ω-amino-alcohol linker are dissolved together in an appropriate solvent and allowed to react at ambient temperature for 1 to 24 hours. Typical solvents depend on the solubility of the reagents and the type of reaction; for example, N,N-dimethylformamide is a useful solvent for the condensation of activated carboxylic acid esters with ω-amino-alcohol linkers, while pyridine is more appropriate for carboxylic acid anhydrides, chlorides or chloroformates where acid byproducts are produced.

Figure 3A:
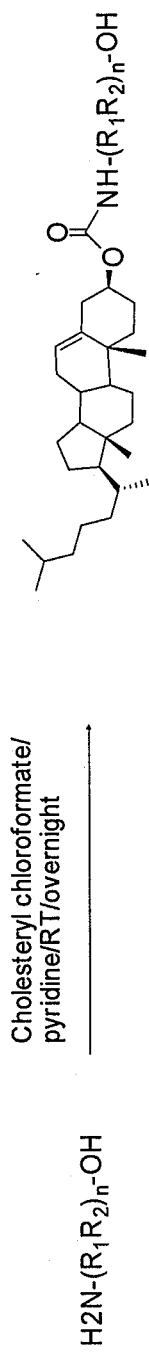
FIG. 3A is a generalized synthetic scheme for the preparation of a conjugate moiety-ω-amino-alcohol linker compound.

FIG. 3A describes a general synthetic scheme for preparing a conjugate moiety-ω-amino-alcohol linker compound. The details of the preparation of cholesteryl 2-hydroxyethylcarbamate according to the above general scheme are given in the following Example 26. In this case cholesterol is the conjugate moiety and cholesteryl chloroformate its reactive derivative.

Example 26

Preparation of cholesteryl 2-hydroxyethylcarbamate

2-Aminoethanol (0.4 mL, 6.7 mmoles) is dissolved in dry pyridine (150 mL) and cholesteryl chloroformate (3.0 g, 6.7 mmoles) is added. The reaction mixture is stirred overnight at ambient temperature. The mixture is evaporated to dryness. The crude product is purified on silica gel (500 mL bed volume) eluting with methylene chloride:methanol (100:4 [v/v], 2000 mL). Fractions containing pure product by thin layer chromatography are pooled and evaporated to a white glassy foam. The foam is dried well in vacuo. The yield is 2.8 g (87%).

Similarly, the following compounds are prepared:
i) Cholesteryl 3-hydroxypropylcarbamate from cholesteryl chloroformate and 3-aminopropan-1-ol.
ii) Cholesteryl 4-hydroxybutylcarbamate from cholesteryl chloroformate and 4-aminobutan-1-ol.
iii) Cholesteryl 5-hydroxypentylcarbamate from cholesteryl chloroformate and 5-aminopentan-1-ol.
iv) Cholesteryl 6-hydroxyhexylcarbamate from cholesteryl chloroformate and 6-aminohexan-1-ol.
v) Cholesteryl 8-hydroxyoctylcarbamate from cholesteryl chloroformate and 8-aminooctan-1-ol. 8-Aminooctan-1-ol is prepared from 8-bromooctan-1-ol and sodium azide in refluxing 95% ethanol, followed by catalytic hydrogenation (10% Pd/C catalyst, 30 psi hydrogen) in methanol.
vi) Cholesteryl 12-hydroxydodecylcarbamate from cholesteryl chloroformate and 12-aminododecan-1-ol. 12-Aminododecanl-1-ol is prepared from 12-bromododecan-1-ol and sodium azide in refluxing 95% ethanol, followed by catalytic hydrogenation (10% Pd/C catalyst, 30 psi hydrogen) in methanol.
vii) Cholesteryl 4-(hydroxymethyl)phenylcarbamate from cholesteryl chloroformate and 4-aminobenzyl alcohol.
viii) Cholesteryl 4-hydroxypiperidine-1-carboxylate from cholesteryl chloroformate and 4-hydroxypiperidine.

For additional clarity and ease of discussion in subsequent sections, Table II presents the structures of the above compounds and the abbreviated nomenclature associated therewith.

Example 27

General Preparation of a Conjugate moiety-ω-amino-alcohol Linker Compound Phosphoramidite A conjugate moiety-ω-amino-alcohol linker compound may be converted into a phosphoramidite derivative using methods well known to those of ordinary skill in the art.

Figure 3B:
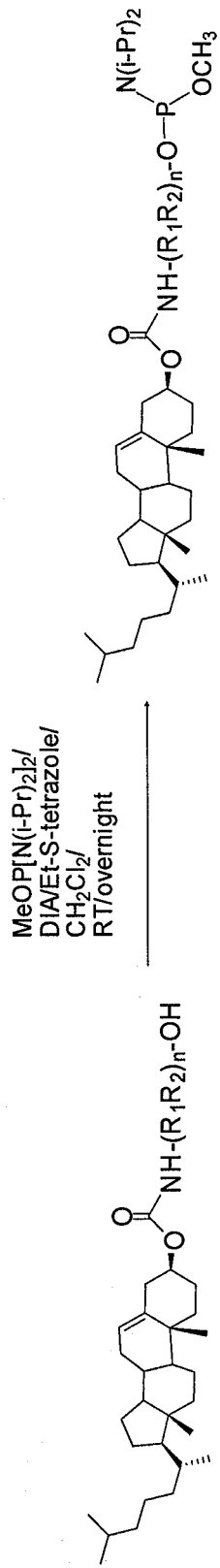
FIG. 3B is a generalized scheme for the preparation of a conjugate moiety-ω-amino-alcohol linker compound phosphoramidite.

FIG. 3B describes a general synthetic scheme for preparing a conjugate moiety-ω-amino-alcohol linker compound phosphoramidite. The details of the preparation of cholesteryl 2-((diisopropylamino)(methoxy)phosphinooxy)-ethylcarbamate according to the above general scheme are given in the following Example 28.

Example 28

Preparation of cholesteryl 2-((diisopropylamino) (methoxy)phosphinooxy)-ethylcarbamate Cholesteryl 2-hydroxyethylcarbamate (2.8 g, 5.8 mmoles) is dissolved in dry methylene chloride (11.6 mL) containing N,N-diisopropylamine (810 μL, 5.8 mmoles). The solution is stirred at ambient temperature. In a separate flask, methyl N,N,N',N'-tetraisopropylphosphorodiamidite (2.3 g, 8.7 mmoles) is dissolved in a mixture of methylene chloride (11.6 mL), N,N-diisopropylamine (810 μL, 5.8 mmoles), and 5-ethylthio-1H-tetrazole in acetonitrile (0.5 M, 5.8 mL, 2.9 mmoles). This solution is stirred at ambient temperature for 5 minutes, and then added in one portion to the first solution. The mixture is stirred overnight at ambient temperature, and then evaporated to a thick syrup. The crude product is purified on silica gel (400 mL bed volume) eluting with hexanes:acetone:triethylamine (94:3:3 [v/v/v], 1000 mL). Fractions containing pure product by thin layer chromatography are pooled and evaporated to a clear colorless syrup. The syrup is co-evaporated twice with toluene (50 mL each). The resulting syrup is dried well in vacuo. The yield is 3.1 g (85%).

Similarly, the following compounds are prepared:
i) Cholesteryl 3-((diisopropylamino)(methoxy)phosphinooxy)propylcarbamate from cholesteryl 3-hydroxypropylcarbamate.
ii) Cholesteryl 4-((diisopropylamino)(methoxy)phosphinooxy)butylcarbamate from cholesteryl 4-hydroxybutylcarbamate.
iii) Cholesteryl 5-((diisopropylamino)(methoxy)phosphinooxy)pentylcarbamate from cholesteryl 5-hydroxypentylcarbamate.
iv) Cholesteryl 6-((diisopropylamino)(methoxy)phosphinooxy)hexylcarbamate from cholesteryl 6-hydroxyhexylcarbamate.
v) Cholesteryl 8-((diisopropylamino)(methoxy)phosphinooxy)octylcarbamate from cholesteryl 8-hydroxyoctylcarbamate.
vi) Cholesteryl 12-((diisopropylamino)(methoxy)phosphinooxy)dodecylcarbamate from cholesteryl 12-hydroxydodecylcarbamate.
vii) Cholesteryl 4-(((diisopropylamino)(methoxy)phosphinooxy)methyl)phenylcarbamate from cholesteryl 4-(hydroxymethyl)phenylcarbamate.
viii) Cholesteryl 4-((diisopropylamino)(methoxy)phosphinooxy)piperidine-1-carboxylate from cholesteryl 4-hydroxypiperidine-1-carboxylate.
ix) Cholesteryl methyl diisopropylphosphoramidite from cholesterol.

Example 29

General Preparation of a Hydroxymethylpyrrolidinol Linker Compound

Figure 4:
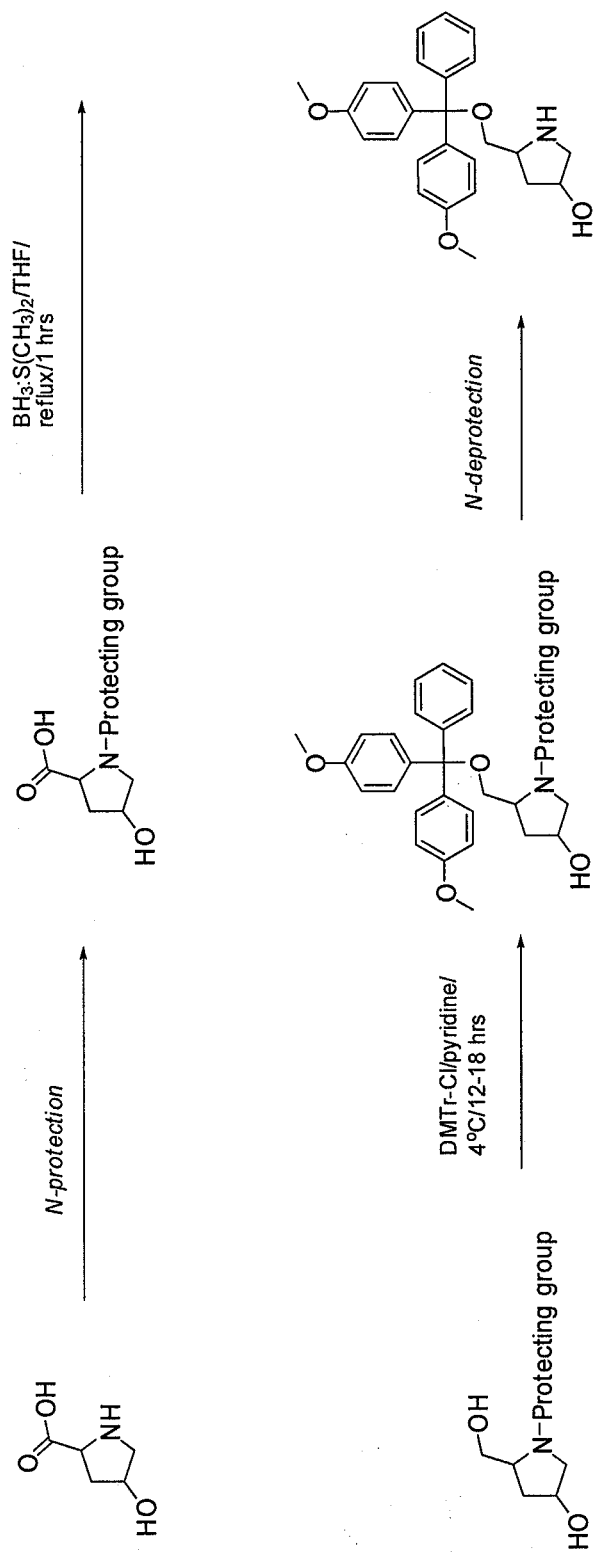
FIG. 4 is a generalized synthetic scheme for the preparation of a hydroxymethylpyrrolidinol linker compound.

FIG. 4 describes a general synthetic scheme for preparing a class of linkers based upon a hydroxymethylpyrrolidinol. Those of ordinary skill in the art will realize that the particular methods and materials described subsequently could be varied to produce the same product compounds. A hydroxyproline compound is reacted with a suitable N-protecting group (e.g., Fmoc, Boc, Cbz) to produce an N-protected hydroxyproline. This compound is reduced using borane-methyl sulfide complex in anhydrous tetrahydrofuran under reflux for 1 hour to produce the N-protected hydroxymethylpyrrolidinol. This compound is treated with 4,4'-dimethoxytritylchloride in pyridine solution at ambient temperature 12-18 hours to produce the N-protected O-DMT-protected hydroxymethylpyrrolidinol. The N-protecting group is then removed using a suitable reaction to yield the desired hydroxymethylpyrrolidinol linker compound.

Figure 5A:
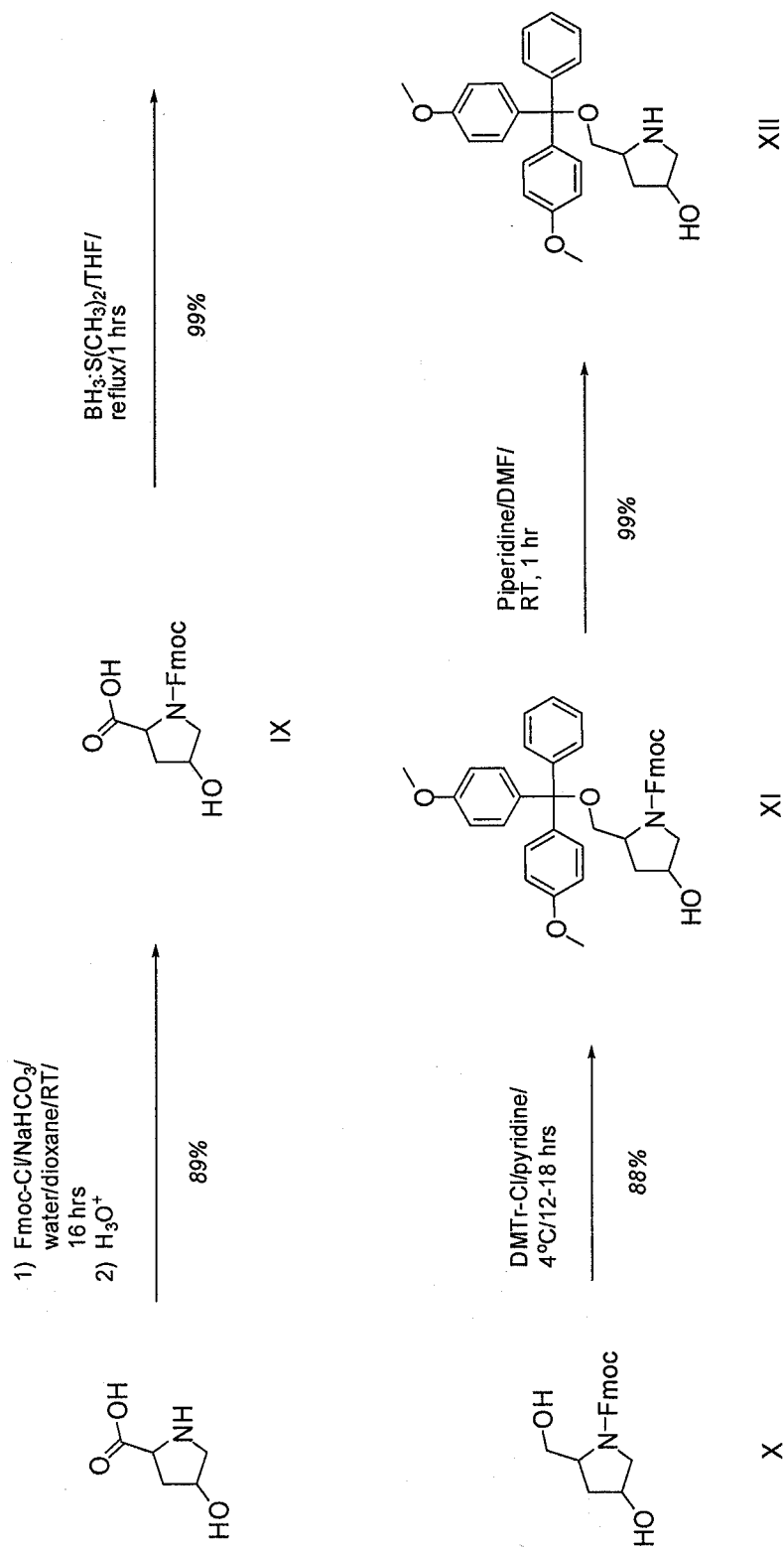
FIG. 5A is a synthetic scheme for the preparation of 5-((bis(4-methoxyphenyl)-(phenyl)methoxy)methyl)pyrrolidin-3-ol.

The details of the preparation of 5-((bis(4-methoxyphenyl)(phenyl)methoxy)methyl)pyrrolidin-3-ol according to the above general scheme are given in the following Examples 30-33, and are illustrated in FIG. 5A.

Example 30

Preparation of 1-(((9H-fluoren-9-yl)methoxy)carbonyl)-4-hydroxypyrrolidine-2-carboxylic acid (IX)

Trans-4-hydroxyproline (5.0 g, 38.1 mmoles) is suspended in a mixture of dioxane (75 mL) and water (75 mL), and stirred briskly at ambient temperature. Sodium bicarbonate (8.0 g, 95.2 mmoles) is added. And the mixture is stirred until all solids dissolve. A solution of 9-fluorenylmethyl chloroformate (11.4 g, 44.0 mmoles) in toluene (25 mL) is added slowly dropwise. The mixture is then stirred for 16 hours. Water (50 mL) and saturated aqueous sodium bicarbonate (50 mL) are added to the reaction mixture, which is then poured into a separatory funnel and washed with diethyl ether (100 mL). The layers are separated, and the aqueous layer is titrated to a pH of about 2 (as determined using pH paper) with concentrated aqueous hydrochloric acid. Ethyl acetate (150 mL) is added to the acidic solution; the mixture is shaken well, and then poured into a separatory funnel. The layers are separated and the aqueous layer extracted again with ethyl acetate (150 mL). The combined ethyl acetate extracts are dried over anhydrous sodium sulfate, filtered and evaporated to a white glassy foam. The crude product is purified on silica gel (400 mL bed volume) eluting with ethyl acetate:acetic acid (100:2 [v/v], 1800 mL), then ethyl acetate:methanol:acetic acid (95:5:2 [v/v/v], 1000 mL). Fractions containing pure product by thin layer chromatography are pooled and evaporated to a clear colorless syrup. The syrup is co-evaporated three time with toluene (150 mL each) to remove residual acetic acid. The resulting amorphous white solid is dried well in vacuo. The yield is 12.0 g (89%).

Example 31

Preparation of (9H-fluoren-9-yl)methyl 4-hydroxy-2-(hydroxymethyl)pyrrolidine-1-carboxylate (X)

1-(((9H-Fluoren-9-yl)methoxy)carbonyl)-4-hydroxypyrrolidine-2-carboxylic acid (13.3 g, 37.6 mmoles) is dissolved in anhydrous tetrahydrofuran (250 mL). The solution is stirred at ambient temperature, and borane-methyl sulfide complex in tetrahydrofuran (2 M, 40 mL, 80 mmoles) is added slowly via syringe. When the evolution of gas ceases, the flask is fitted with a condenser and Drierite drying tube and the solution is refluxed for 1 hour. During this time a white precipitate forms. Methanol (15 mL) is carefully added to the hot reaction mixture, which is refluxed for an additional 15 minutes, during which time the solid dissolves. The mixture is cooled and evaporated to a clear syrup. The syrup is coevaporated three times with methanol (100 mL each) to remove borate salts. The resulting brittle white solid is dried in vacuo. The yield is 12.7 g (99%).

Example 32

Preparation of (9H-fluoren-9-yl)methyl 2-((bis(4-methoxyphenyl)(phenyl)-methoxy)methyl)-4-hydroxypyrrolidine-1-carboxylate (XI)

(9H-Fluoren-9-yl)methyl 4-hydroxy-2-(hydroxymethyl)pyrrolidine-1-carboxylate (10.6 g, 31.2 mmoles) is coevaporated twice with anhydrous pyridine (50 mL each) and then dissolved in anhydrous pyridine (200 mL). The stirred solution is chilled in an ice bath, and 4,4'-dimethoxytritylchloride (11.0 g, 32.5 mmoles) is added in three approximately equal portions at thirty minute intervals. When the addition is complete, the flask is stoppered and place at 4° C. for 16 hours. The mixture is then evaporated to a thick yellow syrup, which is dissolved in toluene (100 mL), filtered and evaporated. The residue is dissolved in methylene chloride (350 mL) and washed successively with cold aqueous citric acid (10% [w/v], 150 mL), saturated aqueous sodium bicarbonate (150 mL) and saturated aqueous sodium chloride (150 mL). The methylene chloride solution is dried over anhydrous sodium sulfate, filtered and evaporated to a yellow foam. The crude product is purified on silica gel (500 mL bed volume) eluting with ethyl acetate:hexanes:triethylamine (50:50:1 [v/v/v], 1300 mL; then 67:33:1 [v/v/v], 1800 mL), then ethyl acetate:triethylamine (99:1 [v/v], 1000 mL). Fractions containing pure product by thin layer chromatography are pooled and evaporated to an off-white amorphous solid which is dried well in vacuo. The yield is 17.7 g (88%).

Example 33

Preparation of 5-((bis(4-methoxyphenyl)(phenyl)methoxy)methyl)pyrrolidin-3-ol (XII)

(9H-Fluoren-9-yl)methyl 2-((bis(4-methoxyphenyl)(phenyl)-methoxy)methyl)-4-hydroxypyrrol-idine-1-carboxylate (3.4 g, 5.3 mmoles) is dissolved in anhydrous N,N-dimethylformamide (15 mL). The solution is stirred at ambient temperature, and piperidine (1.1 mL, 11. mmoles) is added. After 1 hour, a copious white precipitate has formed. Water (100 mL) and ethyl acetate (75 mL) are added, and the mixture is stirred until all of the solid has dissolved. The layers are separated and the aqueous layer is extracted with ethyl acetate (75 mL). The combined ethyl acetate layers are washed with saturated aqueous sodium bicarbonate (50 mL) then saturated aqueous sodium chloride (50 mL), dried over anhydrous sodium sulfate and filtered. The filtrate is evaporated to an amorphous white solid. The crude product is purified on silica gel (150 mL bed volume) eluting with methylene chloride:methanol:triethylamine (94:1:5 [v/v/v], 700 mL; then 90:5:5 [v/v/v], 700 mL). Fractions containing pure product by thin layer chromatography are pooled and evaporated to a white glassy foam, which is dried well in vacuo. The yield is 2.2 g (99%).

Example 34

General Preparation of a Conjugate Moiety-Hydroxymethylpyrrolidinol Linker Compound The considerations for the preparation of these compounds are similar to those discussed previously for the case of conjugate moiety-ω-amino-1,3-diol linker compounds.

Figure 5B:
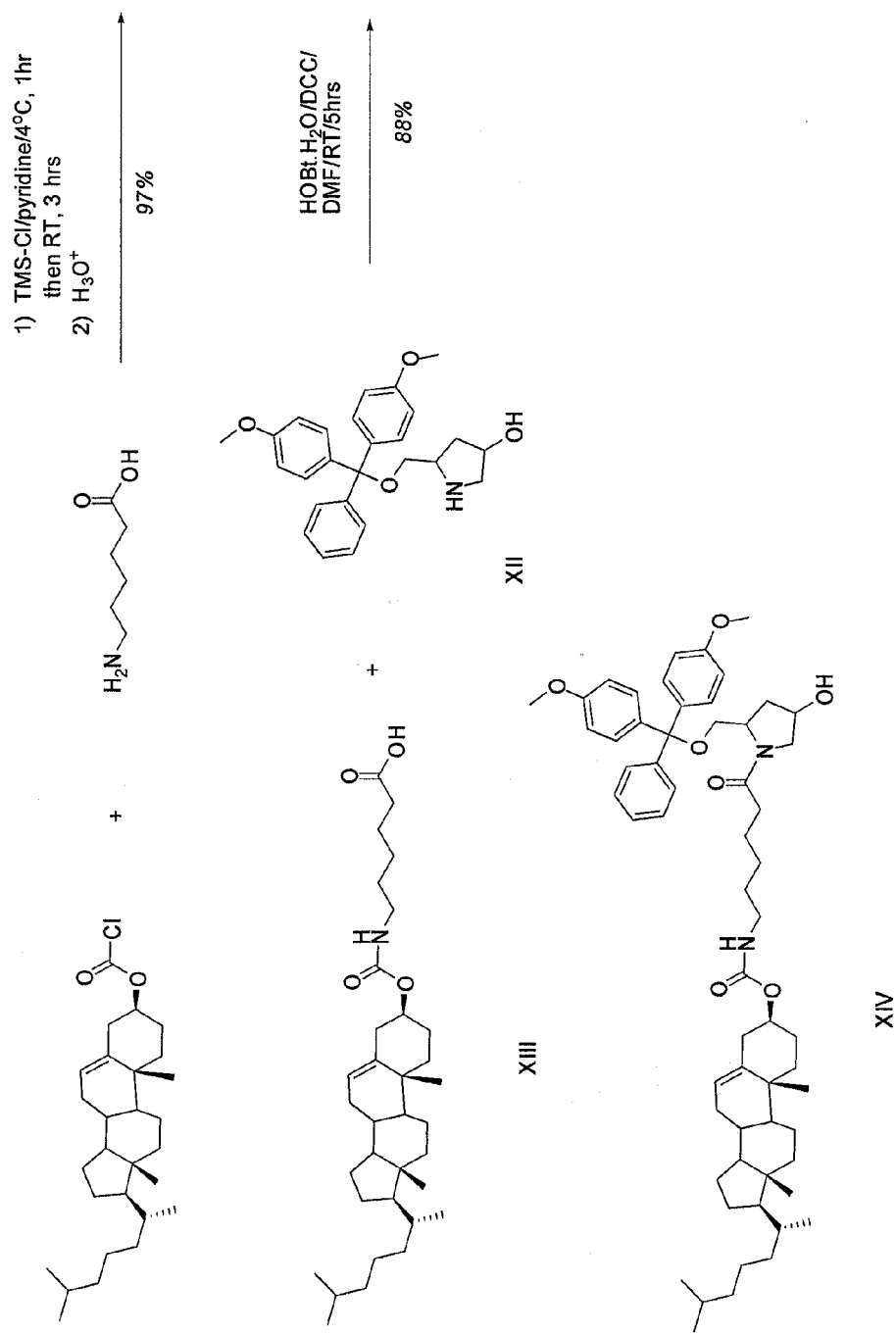
FIG. 5B is a synthetic scheme for the preparation of cholesteryl 6-(2-((bis(4-methoxyphenyl)(phenyl)methoxy)methyl)-4-hydroxypyrrolidin-1-yl)-6-oxohexylcarbamate ("CHOL-C6-HP").

The details of the preparation of cholesteryl 6-(2-((bis(4-methoxyphenyl)(phenyl)methoxy)-methyl)-4-hydroxypyrrolidin-1-yl)-6-oxohexylcarbamate according to the above general scheme are given in the following Examples 35 and 36, and are illustrated in FIG. 5B. In this case cholesterol is the conjugate moiety and 6-cholesteryloxycarbonylaminohexanoic acid its reactive derivative.

Example 35

Preparation of 6-cholesteryloxycarbonylaminohexanoic acid (XIII)

6-Aminohexanoic acid (3.9 g, 29.7 mmoles) is suspended in dry pyridine (60 mL) and the stirred suspension is chilled in an ice bath. Chlorotrimethylsilane (15 mL, 118.6 mmoles) is added via syringe and the mixture is stirred for 1 hour, during which time all solids dissolve. Cholesteryl chloroformate (7.0 g, 15.6 mmoles) is added to the cold solution, followed 1 hour later by a further portion of cholesteryl chloroformate (6.5 g, 14.5 mmoles). The ice bath is then removed and the mixture stirred at ambient temperature for 3 hours. The reaction is again chilled in an ice bath, and cold aqueous hydrochloric acid (0.7 M, 150 mL) is added slowly. After 15 minutes, the mixture is poured into a separatory funnel and methylene chloride is added (200 mL). The contents of the flask are shaken well and the layers separated. The aqueous layer is extracted further with methylene chloride (200 mL). The combined methylene chloride extracts are washed with aqueous hydrochloric acid (0.7 M, 200 mL) then saturated aqueous sodium chloride (200 mL), dried over anhydrous sodium sulfate, and filtered. The filtrate is evaporated to an amorphous white solid. The solid is dissolved in acetone (150 mL) and the product precipitated by the addition of aqueous hydrochloric acid (1 M, 200 mL). The solid is collected by filtration, washed with water, and dried well in vacuo. The yield is 15.8 g (97%).

Example 36

Preparation of cholesteryl 6-(2-((bis(4-methoxyphenyl)(phenyl)methoxy)-methyl)-4-hydroxypyrrolidin-1-yl)-6-oxohexylcarbamate (XIV)

6-cholesteryloxycarbonylaminohexanoic acid (2.9 g, 5.3 mmoles) is dissolved in methylene chloride (50 mL), and 1-hydroxybenzotriazole hydrate (0.9 g, 5.6 mmole) is added, followed by N,N'-dicyclohexylcarbodiimide (1.1 g, 5.3 mmoles). The mixture is stirred at ambient temperature for 1 hour, during which time a white precipitate of N,N'-dicyclohexylurea forms. 5-((bis(4-methoxyphenyl)(phenyl)methoxy)methyl)pyrrolidin-3-ol (2.2 g, 5.2 mmoles) is added, and the mixture is stirred for four hours. The mixture is then filtered and the filtrate is concentrated to a small volume (about 25 mL). Ethyl acetate (200 mL) is added, and the solution is washed three times with saturated aqueous sodium bicarbonate (100 mL each) and once with saturated aqueous sodium chloride (100 mL). The ethyl acetate solution is dried over anhydrous sodium sulfate, filtered and evaporated to a pale yellow glassy foam. The crude product is purified on silica gel (250 mL bed volume) eluting with methylene chloride:hexanes:triethylamine (75:20:5 [v/v/v], 1000 mL) then methylene chloride:triethylamine (95:5 [v/v], 500 mL). Fractions containing pure product by thin layer chromatography are pooled and evaporated to an off-white glassy foam, which is dried well in vacuo. The yield is 4.4 g (88%).

Example 37

General Preparation of a Conjugate Moiety-Hydroxymethylpyrrolidinol Linker Compound Attached to a Solid Support Useful for Oligonucleotide Synthesis The considerations for the preparation of these compounds are similar to those discussed previously for the case of conjugate moiety-ω-amino-1,3-diol linker compounds.

Figure 5C:
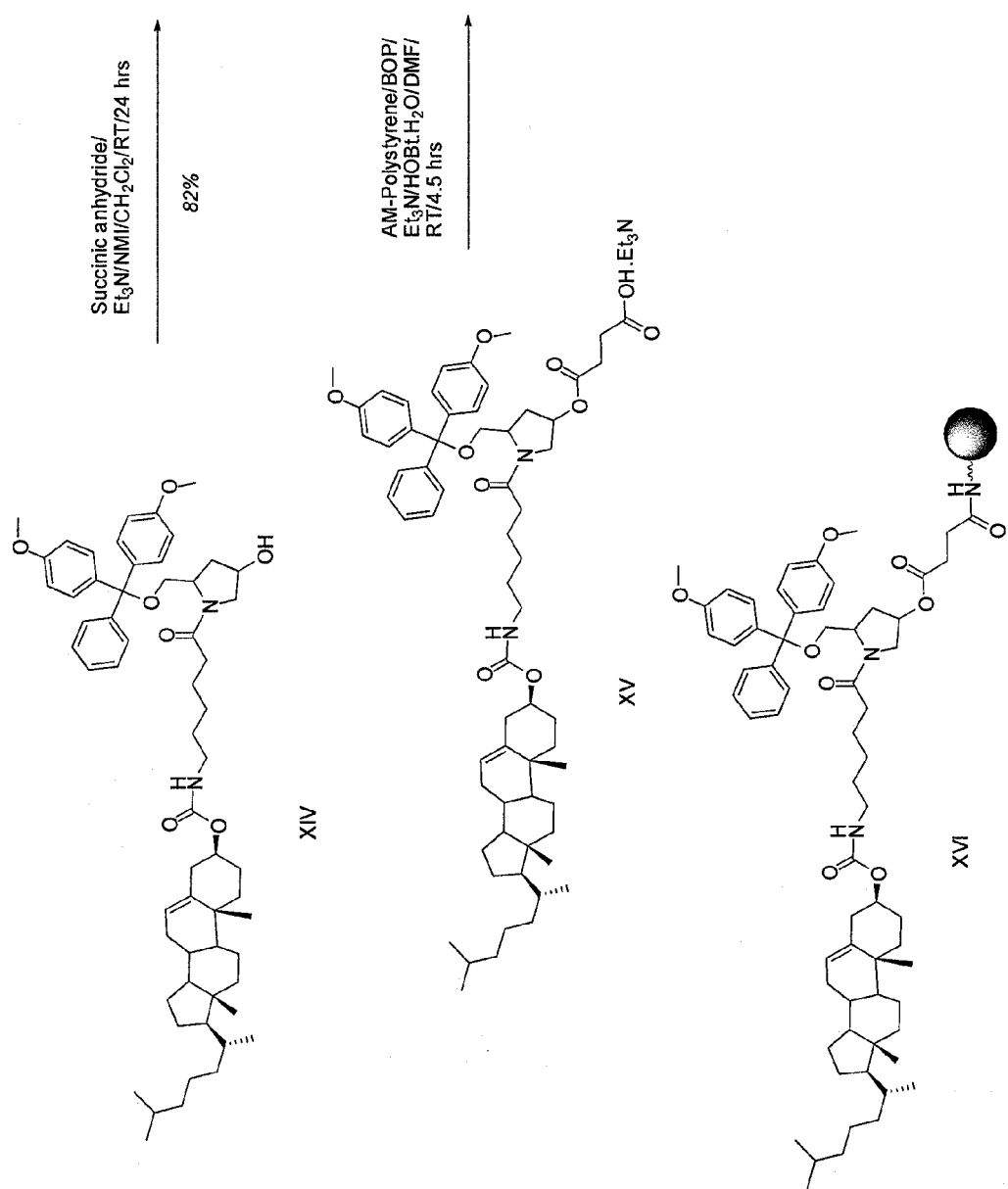
FIG. 5C is a synthetic scheme for preparation of a solid support useful for oligonucleotide synthesis from CHOL-C6-HP.

The details of the preparation of 4-(5-((bis(4-methoxyphenyl)(phenyl)methoxy)methyl)-1-(6-((cholesteryloxy)carbonylamino)hexanoyl)-pyrrolidin-3-yloxy)-4-oxobutanoic acid attached to a solid polystyrene support according to the above general scheme are given in the following Example 38 and 39, and are illustrated in FIG. 5C. In this case the dicarboxylic acid tether is succinic acid.

Example 38

Preparation of 4-(5-((bis(4-methoxyphenyl)(phenyl) methoxy)methyl)-1-(6-((cholesteryloxy)carbonylamino)hexanoyl)-pyrrolidin-3-yloxy)-4-oxobutanoic acid triethylamine salt (XV)

Cholesteryl 6-(2-((bis(4-methoxyphenyl)(phenyl)methoxy)-methyl)-4-hydroxypyrrolidin-1-yl)-6-oxohexylcarbamate (4.3 g, 4.6 mmoles), succinic anhydride (0.5 g, 5.0 mmoles), triethylamine (1.9 mL, 13.6 mmoles) and 1-methylimidazole (0.2 mL, 2.3 mmoles) are dissolved in methylene chloride (50 mL). The reaction is stirred at ambient temperature for 24 hours. The solution is then diluted with methylene chloride (100 mL) and washed twice with ice-cold aqueous citric acid (10% [w/v], 50 mL) and once with saturated aqueous sodium chloride (50 mL). The methylene chloride solution is dried over anhydrous sodium sulfate, filtered and evaporated to yellow resin. The crude product is purified on silica gel (150 mL bed volume) eluting with methylene chloride:triethylamine (95:5 [v/v], 500 mL), then methylene chloride:methanol:triethylamine (90:5:5 [v/v/v], 1000 mL). Fractions containing pure product by thin layer chromatography are pooled and evaporated to an off-white glassy foam which is dried well in vacuo. The yield is 4.3 g (82%).

Example 39

Preparation of 4-(5-((bis(4-methoxyphenyl)(phenyl) methoxy)methyl)-1-(6-((cholesteryloxy)carbonylamino)hexanoyl)-pyrrolidin-3-yloxy)-4-oxobutanoic acid attached to cross-linked aminomethyl-polystyrene (XVI)

AM-Polystyrene (5.0 g, ~33 μmoles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(5-((bis(4-methoxyphenyl)(phenyl)methoxy)methyl)-1-(6-((cholesteryloxy)carbonyl-amino)hexanoyl)-pyrrolidin-3-yloxy)-4-oxobutanoic acid triethylamine salt (241 mg, 210 μmoles), dry, amine-free N,N-dimethylformamide (25.0 mL), triethylamine (58 μL, 420 μmoles), 1-hydroxybenzotriazole hydrate (34 mg, 252 μmoles) and BOP (102 mg, 231 μmoles). The mixture is shaken well until all solids dissolve and then allowed to sit for five minutes at ambient temperature to activate the carboxylic acid. An aliquot of the activated carboxylic acid solution (9.0 mL, 75.6 μmoles) is added via syringe to the shaking solid support suspension. The mixture is shaken for 2.5 hours and a 40 mg aliquot of the solid is then removed and a loading of 12.2 μmoles/gram determined using the method outlined above. An additional aliquot of activated carboxylic acid (2.5 mL, 21.0 μmoles) is added and the suspension shaken for another 2 hours. A loading of 15.0 μmoles/gram is determined. The solid suspension is poured into a coarse fitted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fitted glass funnel and the liquid drained under vacuum. The solid is then washed well with acetonitrile (500 mL) and dried overnight in vacuo.

Example 40

General Preparation of a Conjugate moiety-ω-amino-1,2-diol Linker Compound

The considerations for the preparation of these compounds are similar to those discussed previously for the case of conjugate moiety-ω-amino-1,3-diol linker compounds.

Figure 6A:
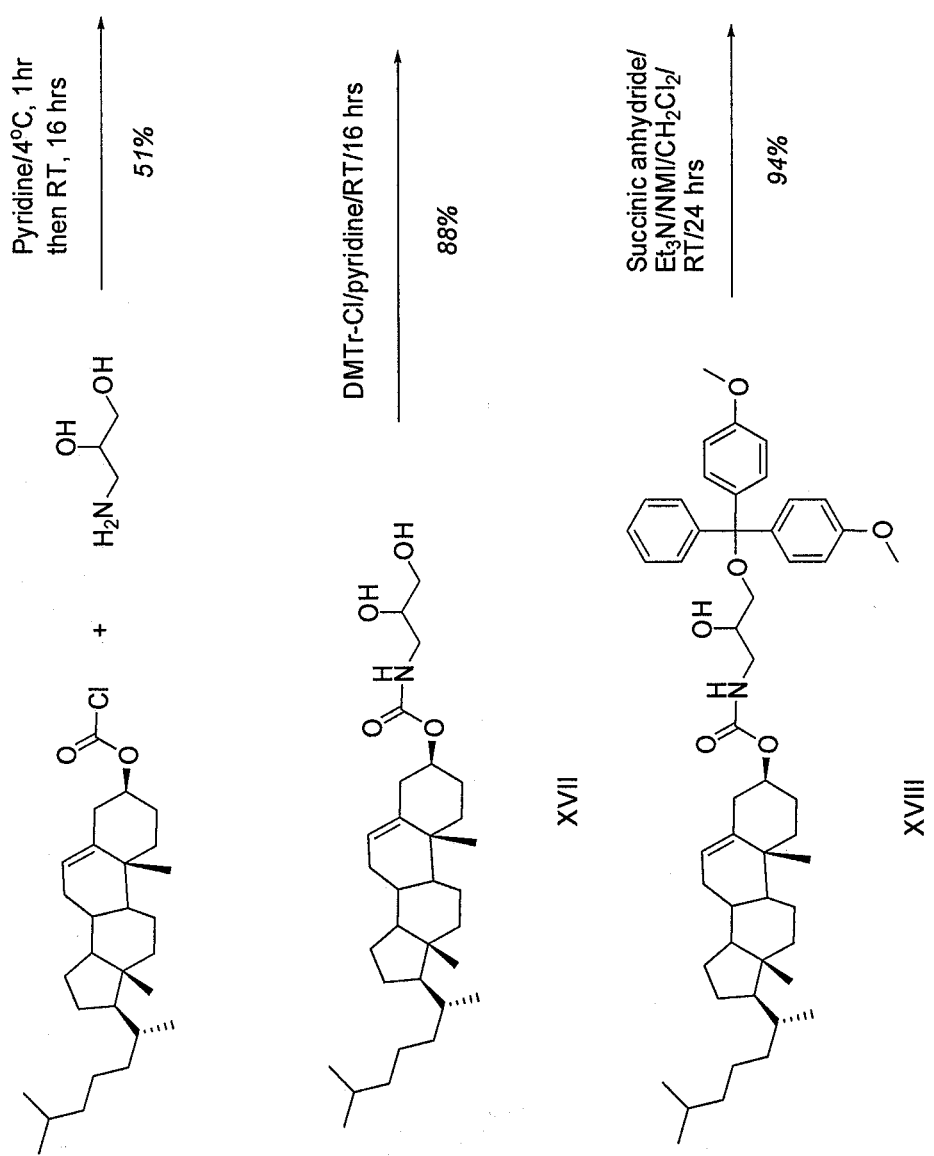
FIGS. 6A-6B depicts a synthetic scheme for the preparation of cholesteryl 3-(bis(4-methoxyphenyl)(phenyl)methoxy)-2-hydroxypropylcarbamate ("CHOL-C3") and preparation of a solid support useful for oligonucleotide synthesis from CHOL-C3.

The details of the preparation of cholesteryl 3-(bis(4-methoxyphenyl)(phenyl)methoxy)-2-hydroxypropylcarbamate according to the above general scheme are given in the following Examples 41 and 42, and are illustrated in FIG. 6A. In this case cholesterol is the conjugate moiety, and cholesteryl chloroformate its reactive derivative.

Example 41

Preparation of cholesteryl 2,3-dihydroxypropylcarbamate (XVII)

3-Amino-1,2-propanediol (2.0 g, 22.0 mmoles) is coevaporated twice with dry pyridine (50 mL each) then dissolved in dry pyridine (147 mL). The solution is stirred in an ice bath, and a solution of cholesteryl chloroformate (10.4 g, 23.1 mmoles) in toluene (50 mL) is added dropwise over 30 minutes. After addition, the ice bath is removed and the reaction mixture is stirred at ambient temperature for 16 hours. The solution is then evaporated, and the residue is coevaporated twice with toluene (50 mL each). The crude product is purified on silica gel (300 mL bed volume) eluting with hexanes:acetone (90:10 [v/v], 1000 mL; then 85:15 [v/v], 1000 mL; then 70:30 [v/v], 1000 mL; then 65:35 [v/v], 1000 mL). Fractions containing pure product by thin layer chromatography are pooled and evaporated to syrup which is dried well in vacuo. The yield is 5.7 g (51%).

Example 42

Preparation of cholesteryl 3-(bis(4-methoxyphenyl) (phenyl)methoxy)-2-hydroxypropylcarbamate (XVIII)

Cholesteryl 2,3-dihydroxypropylcarbamate (5.7 g, 11.4 mmoles) is dissolved in dry pyridine (50 mL) and stirred in an ice bath. A solution of 4,4'-dimethoxytritylchloride (4.1 g, 12.1 mmoles) in pyridine (26 mL) is added slowly dropwise. When the addition is complete, the cooling bath is removed and the mixture is stirred at ambient temperature for 16 hours. The mixture is then evaporated to a thick yellow syrup. The crude product is purified on silica gel (250 mL bed volume) eluting with hexanes:acetone:triethylamine (95:5:2 [v/v/v], 1000 mL; then 90:10:2 [v/v/v], 2000 mL). Fractions containing pure product by thin layer chromatography are pooled and evaporated to a resin which is dried well in vacuo. The yield is 8.1 g (88%).

Example 43

General Preparation of a Conjugate moiety-ω-amino-1,2-diol Linker Compound Attached to a Solid Support Useful for Oligonucleotide Synthesis The considerations for the preparation of these compounds are similar to those discussed previously for the case of conjugate moiety-ω-amino-1,3-diol linker compounds.

Figure 6B:
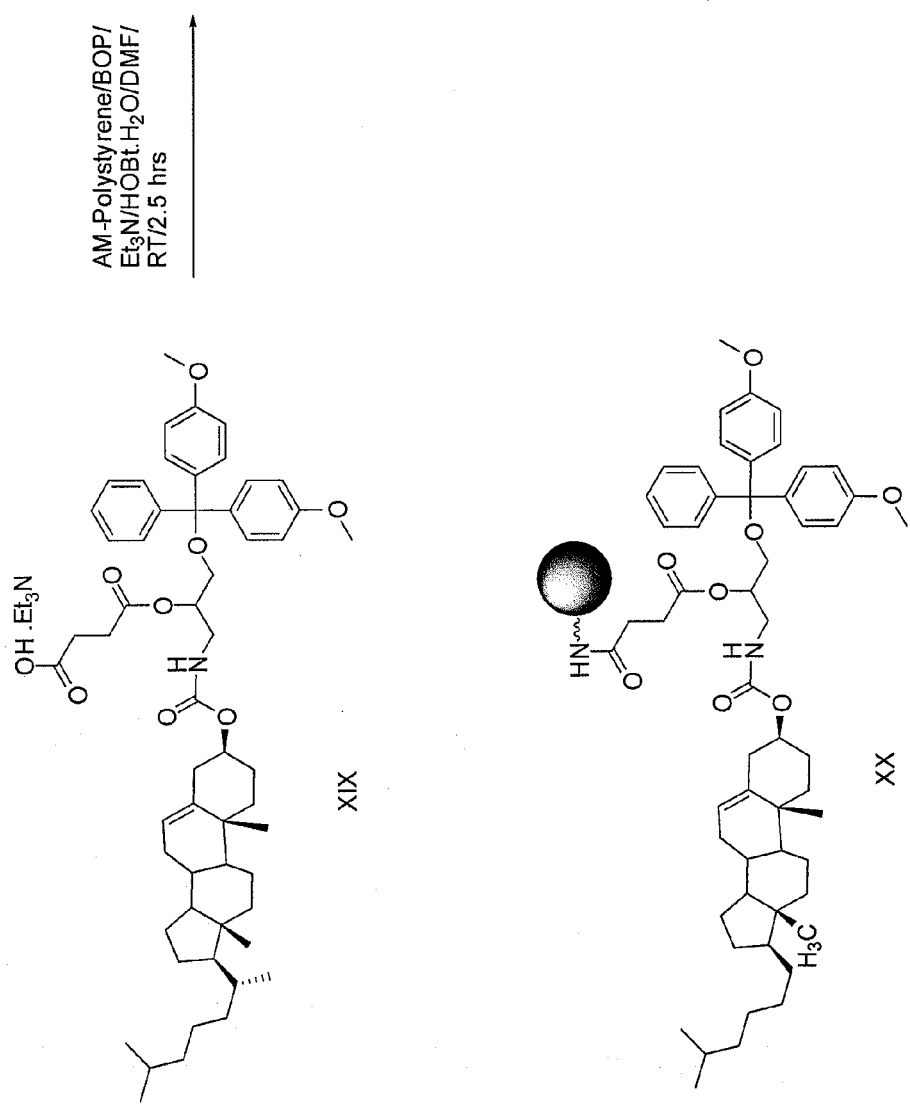

The details of the preparation of 4-(1-(bis(4-methoxyphenyl)(phenyl)methoxy)-3-((cholesteryloxy)carbonylamino) propan-2-yloxy)-4-oxobutanoic acid attached to a solid polystyrene support according to the above general scheme are given in the following Examples 44 and 45, and are illustrated in FIG. 6B. In this case the dicarboxylic acid tether is succinic acid.

Example 44

Preparation of 4-(1-(bis(4-methoxyphenyl)(phenyl) methoxy)-3-((cholesteryloxy)-carbonylamino)propan-2-yloxy)-4-oxobutanoic acid triethylamine salt (XIX)

Cholesteryl 3-(bis(4-methoxyphenyl)(phenyl)methoxy)-2-hydroxypropylcarbamate (8.1 g, 10.0 mmoles), succinic anhydride (1.0 g, 10.0 mmoles), triethylamine (4.2 mL, 30.0 mmoles) and 1-methylimidazole (0.4 mL, 5.0 mmoles) are dissolved in methylene chloride (81 mL). The reaction is stirred at ambient temperature for 24 hours. The solution is then diluted with methylene chloride (100 mL) and washed twice with ice-cold aqueous citric acid (10% [w/v], 50 mL) and once with saturated aqueous sodium chloride (50 mL).

The methylene chloride solution is dried over anhydrous sodium sulfate, filtered and evaporated to yellow resin. The crude product is purified on silica gel (200 mL bed volume) eluting with methylene chloride:triethylamine (95:5 [v/v], 1000 mL), then methylene chloride:methanol:triethylamine (93:2:5 [v/v/v], 1000 mL). Fractions containing pure product by thin layer chromatography are pooled and evaporated to a glassy foam which is dried well in vacuo. The yield is 8.6 g (94%).

Example 45

Preparation of 4-(1-(bis(4-methoxyphenyl)(phenyl) methoxy)-3-((cholesteryloxy)-carbonylamino)propan-2-yloxy)-4-oxobutanoic acid attached to cross-linked aminomethyl-polystyrene (XX)

AM-Polystyrene (5.0 g, ~33 µmoles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(1-(bis(4-methoxyphenyl) (phenyl)methoxy)-3-((cholesteryloxy)-carbonylamino)-propan-2-yloxy)-4-oxobutanoic acid triethylamine salt (113 mg, 113 moles), dry, amine-free N,N-dimethylformamide (25.0 mL), triethylamine (31 µL, 225 µmoles), 1-hydroxybenzotriazole hydrate (18 mg, 135 µmoles) and BOP (55 mg, 124 µmoles). The mixture is shaken well until all solids dissolve and then allowed to sit for five minutes at ambient temperature to activate the carboxylic acid. An aliquot of the activated carboxylic acid solution (16.7 mL, 75.4 µmoles) is added via syringe to the shaking solid support suspension. The mixture is shaken for 1.5 hours and a 40 mg aliquot of the solid is then removed and a loading of 12.5 µmoles/gram determined using the method outlined above. An additional aliquot of activated carboxylic acid (2.7 mL, 12.2 µmoles) is added and the suspension shaken for another hour. A loading of 14.7 µmoles/gram is determined. The solid suspension is poured into a coarse fritted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fitted glass funnel and the liquid drained under vacuum. The solid is then washed well with acetonitrile (500 mL) and dried overnight in vacuo.

Example 46

General Preparation of a Conjugate moiety-1,3-diol Linker Compound Attached to a Solid Support Useful for Oligonucleotide Synthesis Certain desirable conjugate moieties of this invention will have functional groups inherent in their structure that may be converted to provide linker capabilities directly. For example, conjugate moieties having a carboxylic acid group not critical to the function of the conjugate moiety can be directly converted into conjugate moiety-linker compounds using the same chemical transformations described previously for preparing ω-amino-1,3-diol linker compounds. Similarly, conjugate moieties having a hydroxyl group not critical to the function of the conjugate moiety can be directly converted into phosphoramidite derivatives using the same chemical transformations described previously.

Figure 7:
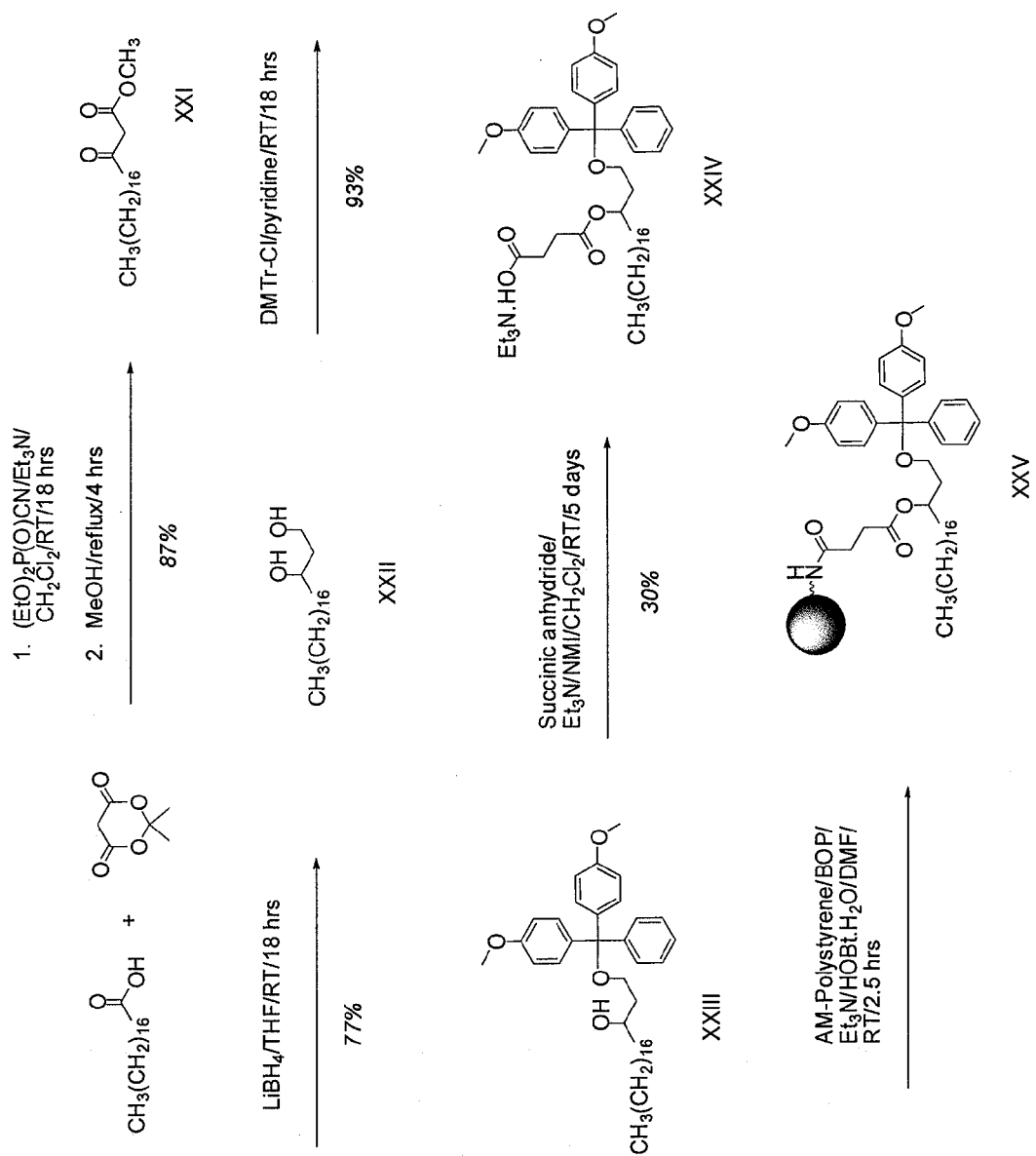
FIG. 7 is a generalized synthetic scheme for the preparation of a conjugate moiety-1,3-diol linker compound attached to a solid support useful for oligonucleotide synthesis.

The details of the preparation of 4-(1-(bis(4-methoxyphenyl)(phenyl)methoxy)icosan-3-yloxy)-4-oxobutanoic acid attached to a solid polystyrene support according to the above general scheme are given in the following Examples 47-51, and are illustrated in FIG. 7. In this case the dicarboxylic acid tether is succinic acid.

Example 47

Preparation of methyl 3-oxoicosanoate (XXI)

Stearic acid (5.0 g, 17.6 mmoles) is suspended in methylene chloride (88 mL) and 2,2-dimethyl-1,3-dioxane-4,6-dione (2.7 g, 18.5 mmoles), triethylamine (6.7 mL, 48.0 mmoles) and diethyl cyanophosphonate (2.7 mL, 17.6 mmoles) are added. All solids dissolve quickly. The solution is stirred for 16 hours at ambient temperature. The reaction mixture is then diluted with methylene chloride (100 mL) and carefully washed three times with aqueous hydrochloric acid (3 M, 50 mL each), three times with water (50 mL each) and once with saturated aqueous sodium chloride (50 mL). The reaction mixture is then dried over anhydrous sodium sulfate, filtered and evaporated. The resulting syrup is dissolved in anhydrous methanol (100 mL) and heated to reflux for 16 hours. The methanol is evaporated and the crude product dissolved in hexanes with slight heating. The crude product was then loaded on silica gel (150 mL bed volume) eluting with hexanes (500 mL) then hexane:acetone (98:2 [v/v], 1000 mL). Fractions containing pure product by thin layer chromatography are pooled and evaporated to dryness. The resulting oil is dried well in vacuo. The yield is 5.2 g (87%).

Similarly, the following compounds are prepared:
i) Methyl 3-oxodecanote from caprylic acid.
ii) (E)-Methyl 3-oxoicos-11-enoate from elaidic acid.
iii) (Z)-Methyl 3-oxoicos-1'-enoate from oleic acid.
iv) (11Z,14Z)-Methyl 3-oxoicosa-11,14-dienoate from linoleic acid.

Example 48

Preparation of icosane-1,3-diol (XXII)

Methyl 3-oxoicosanoate (5.2 g, 15.3 mmoles) is dissolved in anhydrous tetrahydrofuran (31 mL) and this solution is added slowly dropwise to an ice-cooled solution of lithium borohydride in anhydrous tetrahydrofuran (2 M, 31 mL, 61.2 mmoles). When the addition is complete, the cooling bath is removed and the reaction is stirred at ambient temperature for 16 hours. The clear, colorless solution is again cooled in an ice bath, and aqueous hydrochloric acid (1 M, 62 mL) is added slowly dropwise to decompose the excess reducing agent (gas is evolved). When a homogeneous solution is obtained, the mixture is concentrated to remove tetrahydrofuran. Methylene chloride (100 mL) is added; the mixture is shaken well and poured into a separatory funnel. The layers are allowed to separate and the bottom aqueous layer is drawn off. The aqueous layer is then washed once more with methylene chloride (100 mL), and the combined methylene chloride solutions are washed with saturated aqueous sodium chloride (50 mL). The methylene chloride solution is then dried over anhydrous sodium sulfate, filtered and co-evaporated five times with methanol (50 mL each) to dryness. The oil is dried well in vacuo. The yield is 3.7 g (77%).

Similarly, the following compounds are prepared:
i) Decane-1,3-diol from methyl 3-oxodecanote.
ii) (E)-Icos-11-ene-1,3-diol from (E)-methyl 3-oxoicos-11-enoate.
iii) (Z)-Icos-11-ene-1,3-diol from (Z)-methyl 3-oxoicos-11-enoate.
iv) (11Z,14Z)-Icosa-11,14-diene-1,3-diol from (11Z,14Z)-methyl 3-oxoicosa-11,14-dienoate.

Example 49

Preparation of 1-(bis(4-methoxyphenyl)(phenyl)methoxy)icosan-3-ol (XXIII)

Icosane-1,3-diol (3.7 g, 11.8 mmoles) is co-evaporated twice with anhydrous pyridine (50 mL each) and then is dissolved in anhydrous pyridine (60 mL). The solution is chilled in an ice bath, and 4,4'-dimethoxytritylchloride (4.2 g, 12.4 mmoles) is added. The reaction is allowed to warm to ambient temperature and is stirred for 16 hours. The remaining 4,4'-dimethoxytritylchloride is quenched with methanol (10 mL), and the yellow solution is then evaporated to near dryness. The residue is co-evaporated twice to dryness with toluene (50 mL each). The crude product is purified on silica gel (150 mL bed volume) eluting with hexanes:acetone:triethylamine (95.5:5:0:5 [v/v/v], 500 mL). Fractions containing pure product by thin layer chromatography are pooled and evaporated to a pale yellow syrup. The syrup is dried well in vacuo. The yield is 6.8 g (93%).

Similarly, the following compounds are prepared:
i) 1-(Bis(4-methoxyphenyl)(phenyl)methoxy)decan-3-ol from decane-1,3-diol.
ii) (E)-1-(Bis(4-methoxyphenyl)(phenyl)methoxy)icos-11-en-3-ol from (E)-icos-11-ene-1,3-diol.
iii) (Z)-1-(Bis(4-methoxyphenyl)(phenyl)methoxy)icos-11-en-3-ol from (Z)-icos-11-ene-1,3-diol.
iv) (11Z,14Z)-1-(Bis(4-methoxyphenyl)(phenyl)methoxy)icosa-11,14-dien-3-ol from (11Z,14Z)-icosa-11,14-diene-1,3-diol.

Example 50

Preparation of 4-(1-(bis(4-methoxyphenyl)(phenyl)methoxy)icosan-3-yloxy)-4-oxobutanoic acid triethylamine salt (XXIV)

1-(bis(4-methoxyphenyl)(phenyl)methoxy)icosan-3-ol (6.8 g, 11.0 mmoles), succinic anhydride (1.1 g, 11.0 mmoles), triethylamine (4.6 mL, 33.0 mmoles) and 1-methylimidazole (0.44 mL, 5.5 mmoles) are dissolved in methylene chloride (68 mL). The reaction is stirred at ambient temperature for five days, during which time the solution darkened. The solution is then diluted with methylene chloride (100 mL) and washed twice with ice-cold aqueous citric acid (10% [w/v], 50 mL) and once with saturated aqueous sodium chloride (50 mL). The methylene chloride solution is dried over anhydrous sodium sulfate, filtered and evaporated to a dark resin. The crude product is purified on silica gel (200 mL bed volume) eluting with methylene chloride:triethylamine (95:5 [v/v/v], 500 mL), then methylene chloride:methanol:triethylamine (93:2:5 [v/v/v], 1000 mL). Fractions containing pure product by thin layer chromatography are pooled and evaporated to a resin. The resin is dried well in vacuo. The yield is 2.4 g (30%).

Similarly, the following compounds are prepared:
i) 1-(Bis(4-methoxyphenyl)(phenyl)methoxy)decan-3-yloxy)-4-oxobutanoic acid triethylamine salt from 1-(bis(4-methoxyphenyl)(phenyl)methoxy)decan-3-ol.
ii) (E)-1-(Bis(4-methoxyphenyl)(phenyl)methoxy)icos-11-en-3-yloxy)-4-oxobutanoic acid triethylamine salt from (E)-1-(bis(4-methoxyphenyl)(phenyl)methoxy)icos-11-en-3-ol.
iii) (Z)-1-(Bis(4-methoxyphenyl)(phenyl)methoxy)icos-11-en-3-yloxy)-4-oxobutanoic acid triethylamine salt from (Z)-1-(bis(4-methoxyphenyl)(phenyl)methoxy)icos-11-en-3-ol.
iv) (11Z,14Z)-1-(Bis(4-methoxyphenyl)(phenyl)methoxy)icosa-11,14-dien-3-yloxy)-4-oxobutanoic acid triethylamine salt from (11Z,14Z)-1-(bis(4-methoxyphenyl)-(phenyl)methoxy)icosa-11,14-dien-3-ol.

Example 51

Preparation of 4-(1-(bis(4-methoxyphenyl)(phenyl)methoxy)icosan-3-yloxy)-4-oxobutanoic acid attached to cross-linked aminomethyl-polystyrene (XV)

AM-Polystyrene (5.0 g, ~33 µmoles amino groups per gram; Applied Biosystems) is suspended in dry, amine-free N,N-dimethylformamide (37.5 mL) in a single neck round bottom flask (250 mL) capped with a rubber septum. The flask is placed on a wrist-action shaker and shaken at ambient temperature to gently but thoroughly agitate the solid. In another flask (50 mL) are placed 4-(1-(bis(4-methoxyphenyl)methoxy)icosan-3-yloxy)-4-oxobutanoic acid triethylamine salt (49 mg, 60 µmoles), dry, amine-free N,N-dimethylformamide (25.0 mL), triethylamine (17 µL, 120.0 µmoles), 1-hydroxybenzotriazole hydrate (10 mg, 72 µmoles) and BOP (29 mg, 66 µmoles). The mixture is shaken well until all solids dissolve and then allowed to sit for five minutes at ambient temperature to activate the carboxylic acid. An aliquot of the activated carboxylic acid solution (16.7 mL, 40.0 µmoles) is added via syringe to the shaking solid support suspension. The mixture is shaken for 1.5 hours and a 40 mg aliquot of the solid is then removed and a loading of 11.9 µmoles/gram determined using the method outlined above. An additional aliquot of activated carboxylic acid (1.0 mL, 2.4 µmoles) is added and the suspension shaken for another hour. A loading of 16 µmoles/gram is determined. The solid suspension is poured into a coarse fitted glass funnel and the liquid drained under vacuum. The solid is then washed well with N,N-dimethylformamide (200 mL), acetone (200 mL) and acetonitrile (200 mL). It is dried overnight in vacuo. Residual amino groups on the support are capped by suspending the dried solid in a mixture of acetic anhydride in acetonitrile (10% [v/v], 25 mL) and 1-methylimidazole in acetonitrile (10% [v/v], 25 mL) and shaking for 2.5 hours at ambient temperature. The solid suspension is poured into a coarse fitted glass funnel and the liquid drained under vacuum. The solid is then washed well with acetonitrile (500 mL) and dried overnight in vacuo.

Solid supports having the compounds listed in Example 50 (i)-(iv) attached and loadings of approximately 15.0±1.0 moles/gram are prepared similarly.

TABLE I

| Compound Name | Structure | Abbreviation |
|---|---|---|
| Cholesteryl 5-(bis(4-methoxyphenyl)(phenyl)methoxy)-3-hydroxypentylcarbamate | 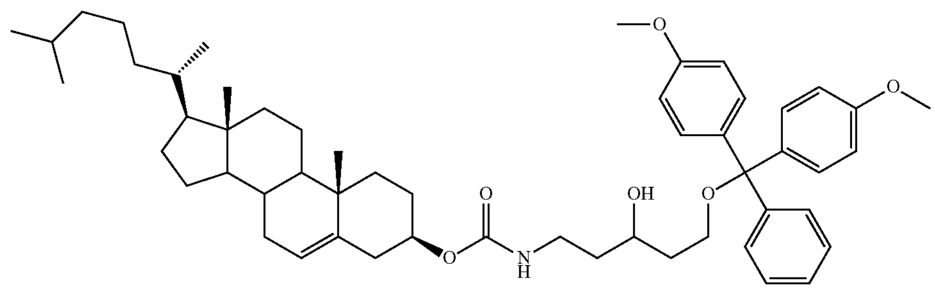 [SMILES: COc1ccc(C(OCCC(O)CCNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-C5 |
| Cholesteryl 8-(bis(4-methoxyphenyl)(phenyl)methoxy)-6-hydroxyoctylcarbamate | 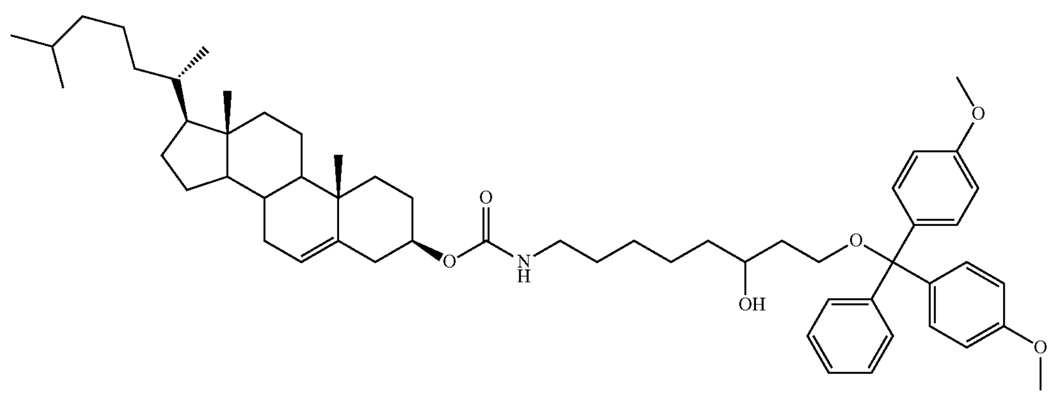 [SMILES: COc1ccc(C(OCCC(O)CCCCCNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-C8 |

TABLE 1-continued

| Compound Name | Structure | Abbreviation |
|---|---|---|
| Cholesteryl 10-(bis(4-methoxyphenyl)(phenyl)methoxy)-8-hydroxydodecylcarbamate | 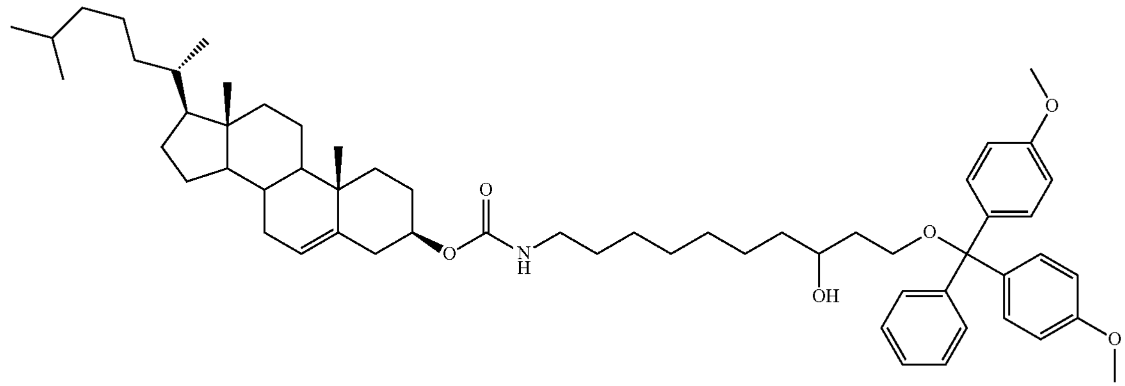 [SMILES: COc1ccc(C(OCCC(O)CCCCCCCNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-C10 |
| Cholesteryl 14-(bis(4-methoxyphenyl)(phenyl)methoxy)-12-hydroxytetradecylcarbamate | 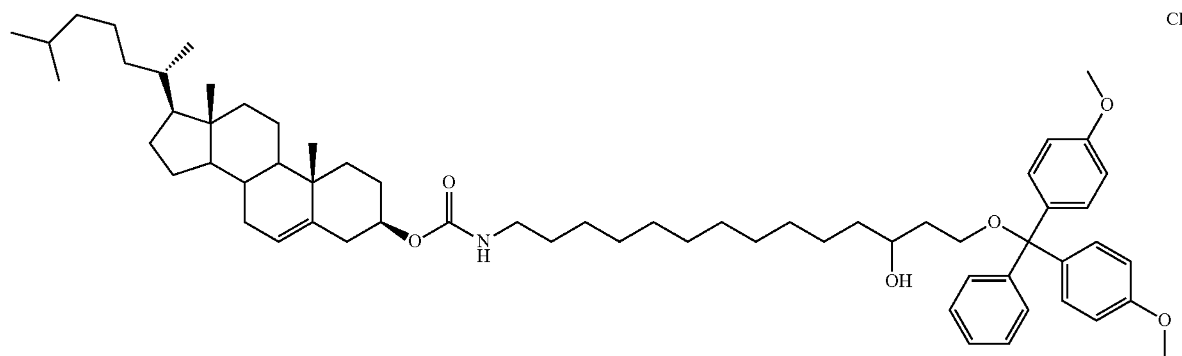 | CHOL-C14 |

TABLE 1-continued

| Compound Name | Structure | Abbreviation |
| --- | --- | --- |
| Cholesteryl 4-(3-(bis(4-methoxyphenyl)(phenyl)methoxy)-1-hydroxypropyl)phenylcarbamate | 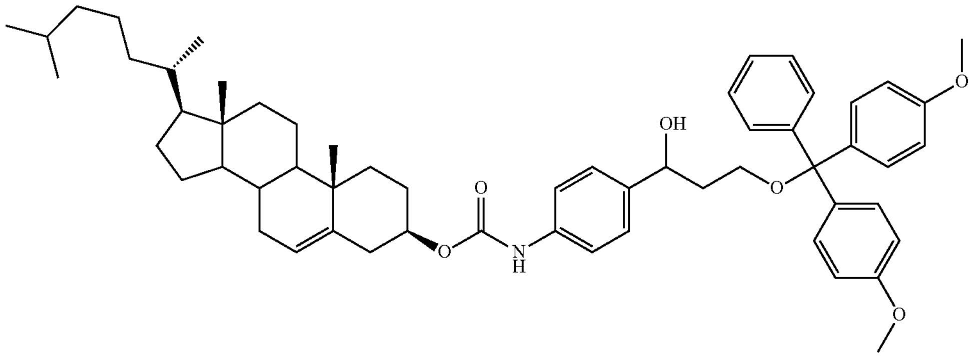 [SMILES: COc1ccc(C(OCCC(O)c2ccc(NC(=O)O[C@@H]3CC[C@]4(C)C(=CCC5C4CC[C@]4(C)C5CC[C@H]4[C@@H](C)CCCC(C)C)C3)cc2)(c2ccccc2)c2ccc(OC)cc2)cc1] | CHOL-ABA |
| Cholesteryl 4-(3-(bis(4-methoxyphenyl)(phenyl)methoxy)-1-hydroxypropyl)piperidine-1-carboxylate | 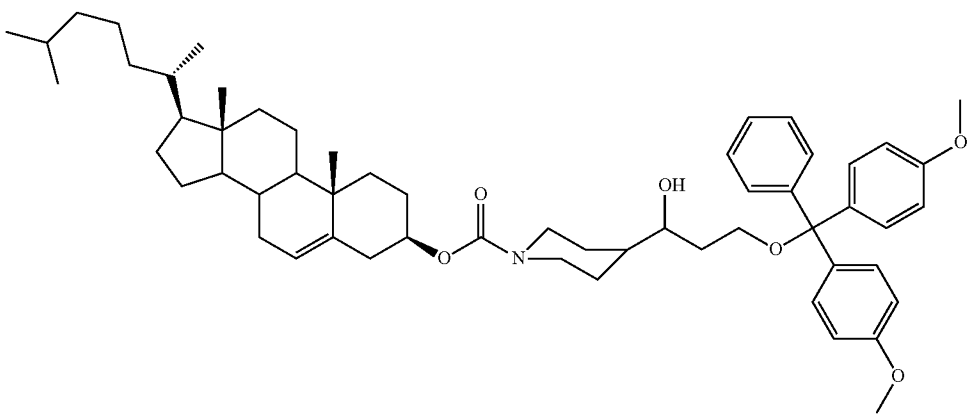 [SMILES: COc1ccc(C(OCCC(O)C2CCN(C(=O)O[C@@H]3CC[C@]4(C)C(=CCC5C4CC[C@]4(C)C5CC[C@H]4[C@@H](C)CCCC(C)C)C3)CC2)(c2ccccc2)c2ccc(OC)cc2)cc1] | CHOL-PIP |

TABLE 1-continued

| Compound Name | Structure | Abbreviation |
|---|---|---|
| Cholesteryl 2-(3-(bis(4-methoxyphenyl)(phenyl)methoxy)-1-hydroxypropyl)pyrrolidine-1-carboxylate | 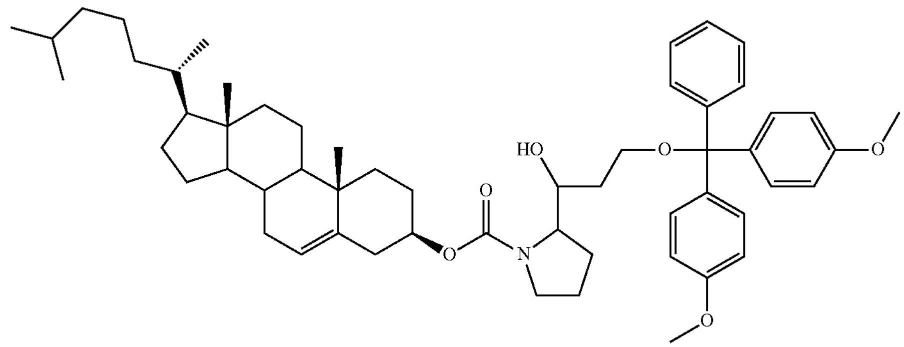 [SMILES: COc1ccc(C(OCCC(O)C2CCCN2C(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-PRO |
| N-(8-(bis(4-methoxyphenyl)(phenyl)methoxy)-6-hydroxyoctyl)acetamide | 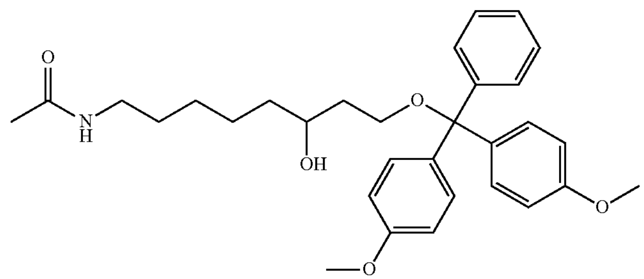 [SMILES: COc1ccc(C(OCCC(O)CCCCCNC(C)=O)(c2ccccc2)c2ccc(OC)cc2)cc1] | Ac-C8 |
| Cholesteryl 6-(8-(bis(4-methoxyphenyl)(phenyl)methoxy)-6-hydroxyoctylamino)-6-oxohexylcarbamate | | CHOL-C8 + C6 |

TABLE 1-continued

| Compound Name | Structure | Abbreviation |
|---|---|---|
| Cholesteryl 12-(8-(bis(4-methoxyphenyl)(phenyl)methoxy)-6-hydroxyoctylamino)-12-oxo-dodecylcarbamate | 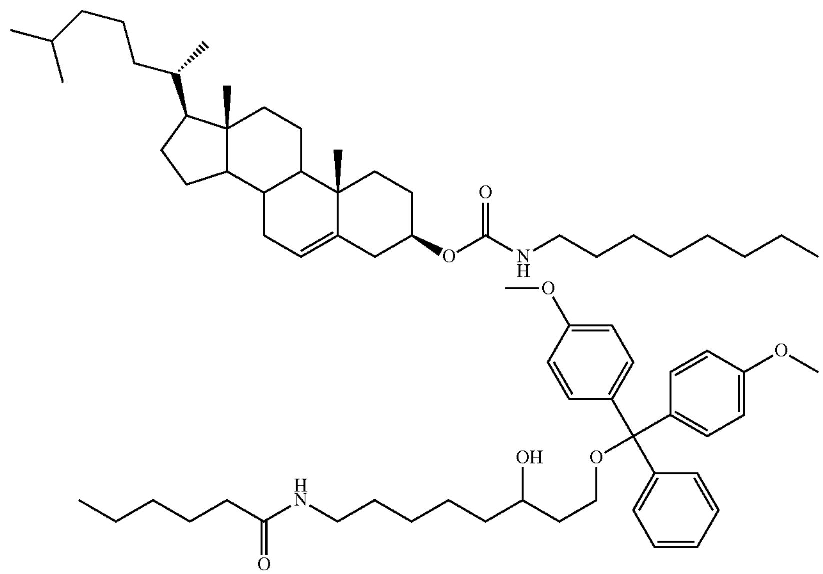 | CHOL-C8 + C12 |
| Cholesteryl 6-(2-((bis(4-methoxyphenyl)(phenyl)methoxy)-methyl)-4-hydroxypyrrolidin-1-yl)-6-oxohexylcarbamate | 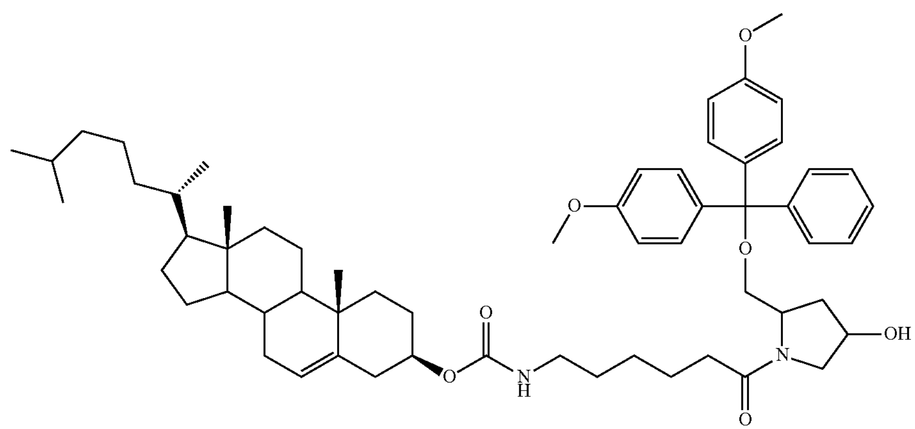 [SMILES: COc1ccc(C(OCC2CC(O)CN2C(=O)CCCCCNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-C6-Hp |

TABLE 1-continued

| Compound Name | Structure | Abbreviation |
|---|---|---|
| Cholesteryl 3-(bis(4-methoxyphenyl)(phenyl)methoxy)-2-hydroxypropyl carbamate | 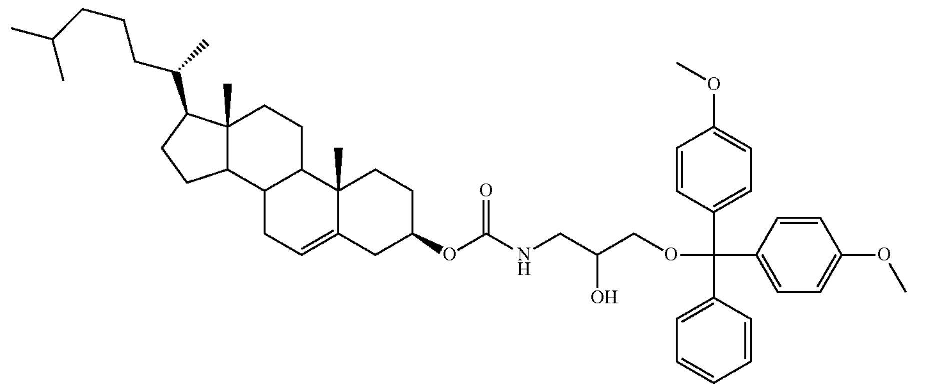 [SMILES: COc1ccc(C(OCC(O)CNC(=O)O[C@@H]2CC[C@]3(C)C(=CCC4C3CC[C@]3(C)C4CC[C@H]3[C@@H](C)CCCC(C)C)C2)(c2ccccc2)c2ccc(OC)cc2)cc1] | CHOL-C3 |
| 5α-cholestan-3β-yl 5-(bis(4-methoxyphenyl)(phenyl)methoxy)-3-hydroxypentyl carbamate | 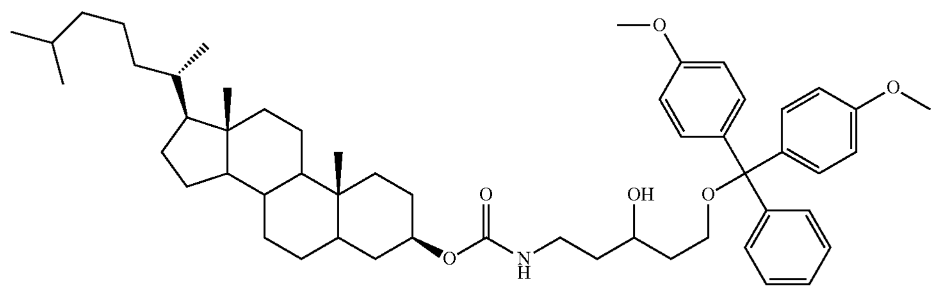 [SMILES: COc1ccc(C(OCCC(O)CCNC(=O)O[C@@H]2CC[C@]3(C)C(CCC4C3CC[C@]3(C)C4CC[C@H]3[C@@H](C)CCCC(C)C)C2)(c2ccccc2)c2ccc(OC)cc2)cc1] | CHLN-C5 |
| Stigmasteryl 5-(bis(4-methoxyphenyl)(phenyl)methoxy)-3-hydroxypentyl carbamate | 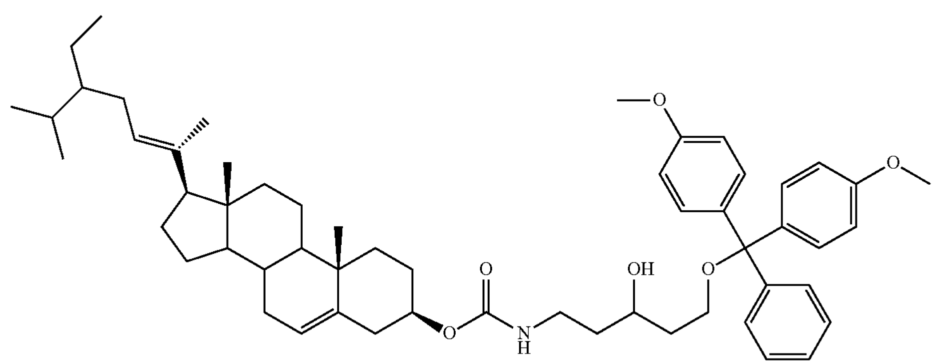 | STIG-C5 |

TABLE 1-continued

| Compound Name | Structure | Abbreviation |
|---|---|---|
| Ergosteryl 5-(bis(4-methoxyphenyl)(phenyl)methoxy)-3-hydroxypentylcarbamate | 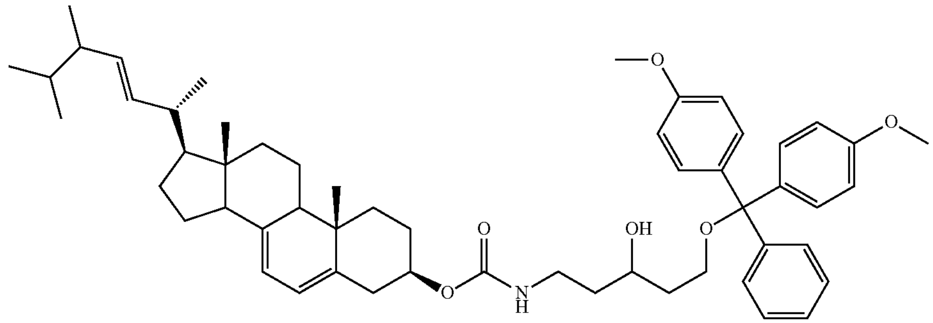 [SMILES: COc1ccc(C(OCCC(O)CCNC(=O)O[C@@H]2CC[C@]3(C)C(=CC=C4C3CC[C@]3(C)C4CC[C@H]3[C@@H](C)/C=C/C(C)C(C)C)C2)(c2ccccc2)c2ccc(OC)cc2)cc1] | ERGO-C5 |
| Trans-androsteronyl 5-(bis(4-methoxyphenyl)(phenyl)methoxy)-3-hydroxypentylcarbamate | 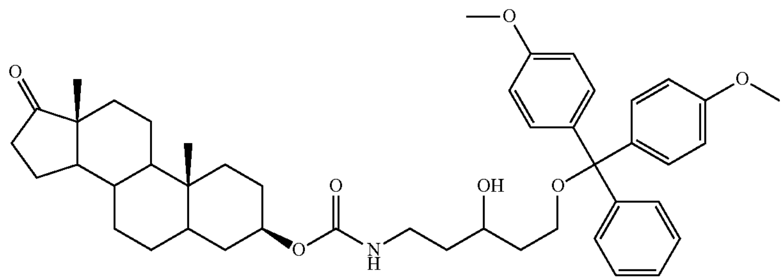 [SMILES: COc1ccc(C(OCCC(O)CCNC(=O)O[C@@H]2CC[C@]3(C)C(CCC4C3CC[C@@]3(C)C(=O)CCC43)C2)(c2ccccc2)c2ccc(OC)cc2)cc1] | ANDR-C5 |
| Pregnenolonyl 5-(bis(4-methoxyphenyl)(phenyl)methoxy)-3-hydroxypentylcarbamate | 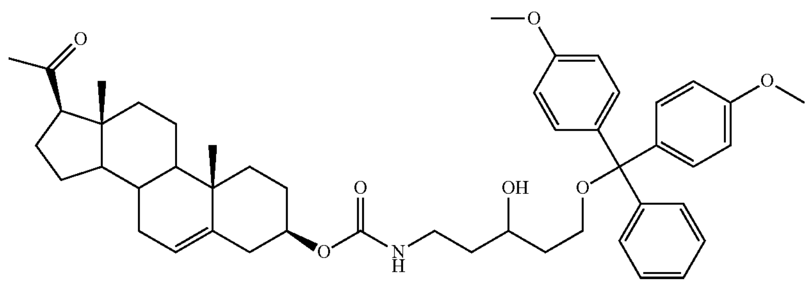 [SMILES: COc1ccc(C(OCCC(O)CCNC(=O)O[C@@H]2CC[C@]3(C)C(=CCC4C3CC[C@]3(C)C4CC[C@H]3C(C)=O)C2)(c2ccccc2)c2ccc(OC)cc2)cc1] | PREG-C5 |

TABLE 1-continued

| Compound Name | Structure | Abbreviation |
|---|---|---|
| Cholanyl 5-(bis(4-methoxyphenyl)(phenyl)methoxy)-3-hydroxypentylamide | | CHLA-C5 |
| 5α-Androstan-3β-yl 5-(bis(4-methoxyphenyl)(phenyl)methoxy)-3-hydroxypentylcarbamate | 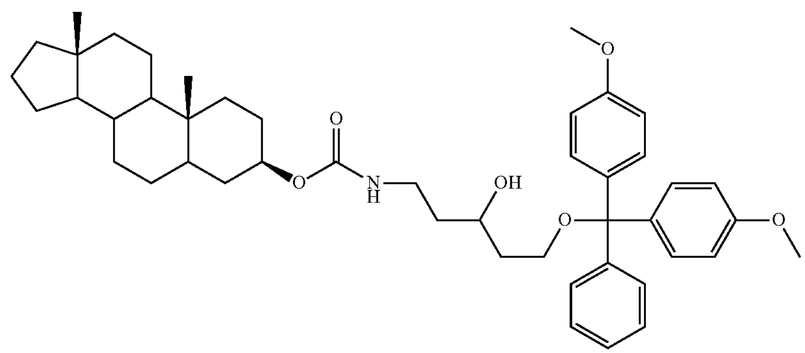 [SMILES: COc1ccc(C(OCCC(O)CCNC(=O)O[C@@H]2CC[C@]3(C)C(CCC4C5CCC[C@]5(C)CCC43)C2)(c2ccccc2)c2ccc(OC)cc2)cc1] | 3BAND-C5 |
| 5α-Androstan-17β-yl 5-(bis(4-methoxyphenyl)(phenyl)methoxy)-3-hydroxypentylcarbamate | 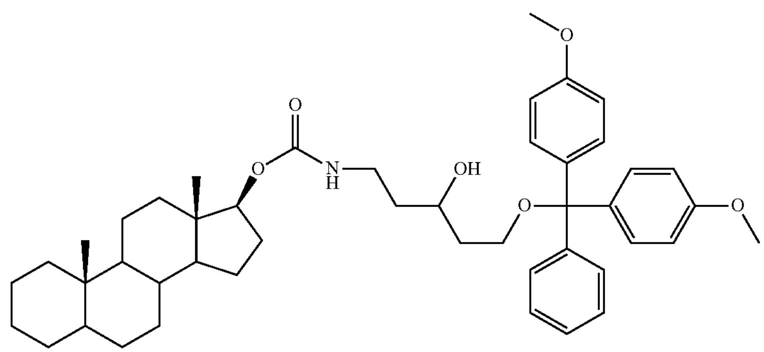 [SMILES: COc1ccc(C(OCCC(O)CCNC(=O)O[C@H]2CCC3C4CCC5CCCC[C@]5(C)C4CC[C@@]32C)(c2ccccc2)c2ccc(OC)cc2)cc1] | 17BAND-C5 |

TABLE 1-continued

| Compound Name | Structure | Abbreviation |
|---|---|---|
| 3-O-acetyl-lithocholyl 5-(bis(4-methoxyphenyl)(phenyl)methoxy)-3-hydroxypentylamide | 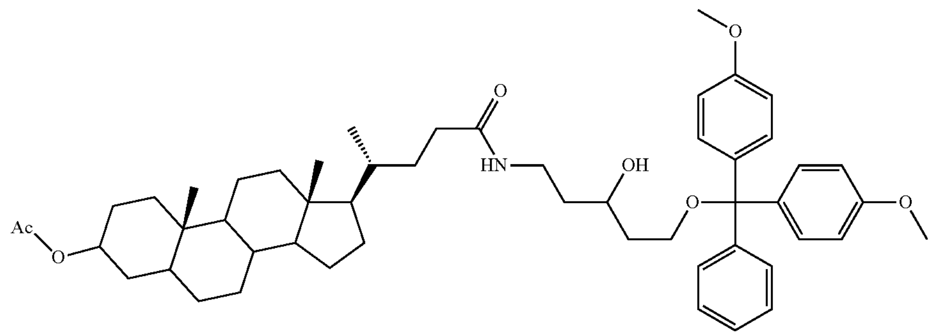 [SMILES: COc1ccc(C(OCCC(O)CCNC(=O)CC[C@@H](C)[C@H]2CCC3C4CCC5CC(OC(C)=O)CC[C@]5(C)C4CC[C@@]32C)(c2ccccc2)c2ccc(OC)cc2)cc1] | ACLITH-C5 |
| Lithocholic acid methyl amide 5-(bis(4-methoxyphenyl)(phenyl)methoxy)-3-hydroxypentyl-carbamate | | LITHNM-C5 |

TABLE II

| Compound Name | Structure | Abbreviation |
| --- | --- | --- |
| Cholesterol | 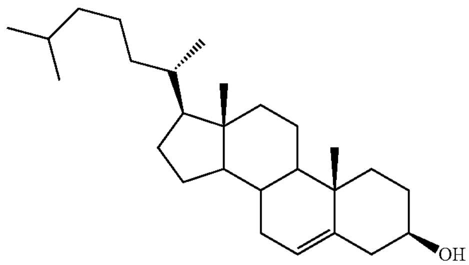 [SMILES: CC(C)CCC[C@H](C)[C@@H]1CCC2C3CC=C4C[C@H](O)CC[C@@]4(C)C3CC[C@]21C] | 5'C0 |
| Cholesteryl 2-hydroxyethylcarbamate | 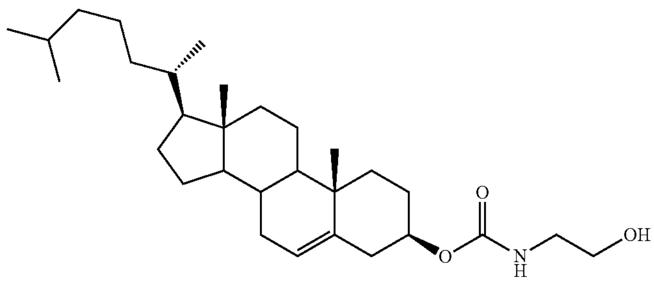 [SMILES: CC(C)CCC[C@H](C)[C@@H]1CCC2C3CC=C4C[C@H](OC(=O)NCCO)CC[C@@]4(C)C3CC[C@]21C] | 5'C2 |
| Cholesteryl 3-hydroxypropylcarbamate | 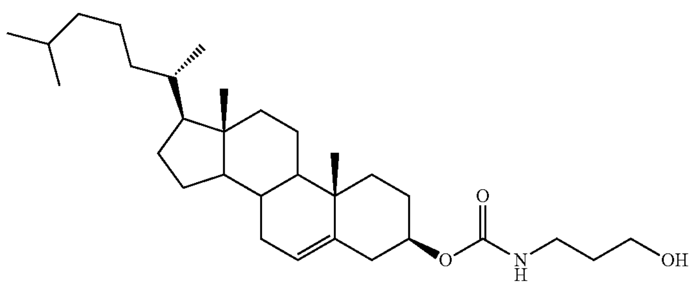 [SMILES: CC(C)CCC[C@H](C)[C@@H]1CCC2C3CC=C4C[C@H](OC(=O)NCCCO)CC[C@@]4(C)C3CC[C@]21C] | 5'C3 |
| Cholesteryl 4-hydroxybutylcarbamate | 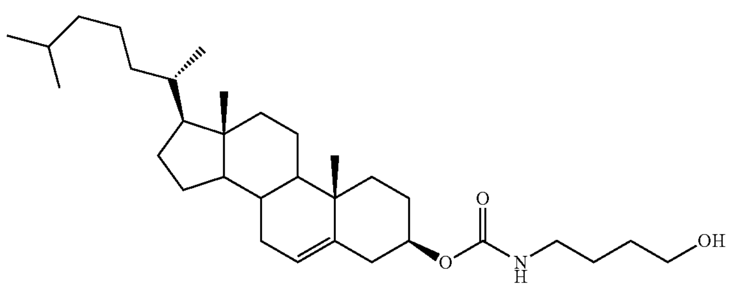 [SMILES: CC(C)CCC[C@H](C)[C@@H]1CCC2C3CC=C4C[C@H](OC(=O)NCCCCO)CC[C@@]4(C)C3CC[C@]21C] | 5'C4 |
| Cholesteryl 5-hydroxypentylcarbamate | 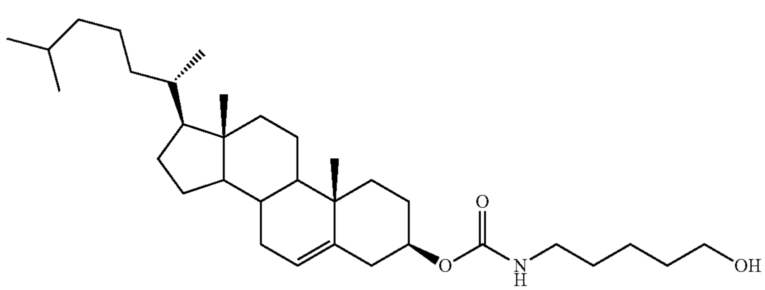 [SMILES: CC(C)CCC[C@H](C)[C@@H]1CCC2C3CC=C4C[C@H](OC(=O)NCCCCCO)CC[C@@]4(C)C3CC[C@]21C] | 5'C5 |

TABLE II-continued

| Compound Name | Structure | Abbreviation |
|---|---|---|
| Cholesteryl 6-hydroxyhexylcarbamate | 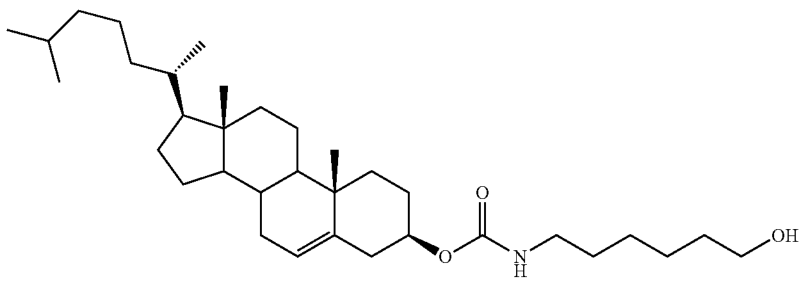 [SMILES: CC(C)CCC[C@H](C)[C@@H]1CCC2C3CC=C4C[C@H](OC(=O)NCCCCCCO)CC[C@@]4(C)C3CC[C@]21C] | 5'C6 |
| Cholesteryl 8-hydroxyoctylcarbamate | 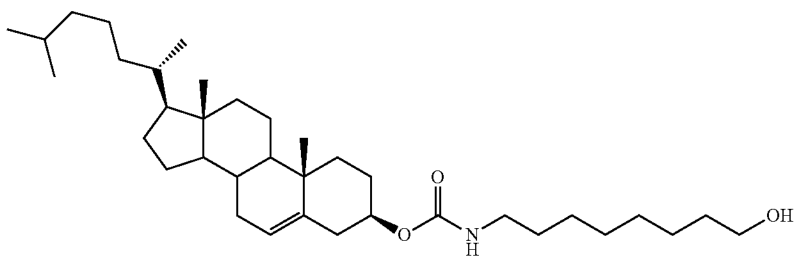 [SMILES: CC(C)CCC[C@H](C)[C@@H]1CCC2C3CC=C4C[C@H](OC(=O)NCCCCCCCCO)CC[C@@]4(C)C3CC[C@]21C] | 5'C8 |
| Cholesteryl 12-hydroxydodecylcarbamate | 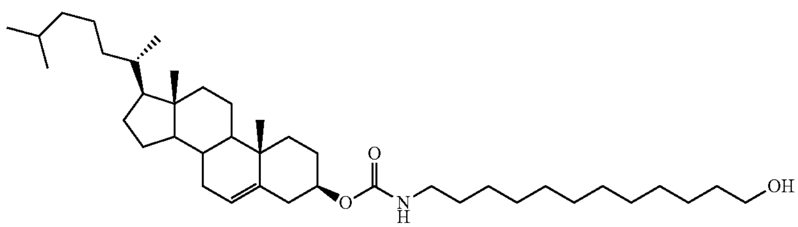 [SMILES: CC(C)CCC[C@H](C)[C@@H]1CCC2C3CC=C4C[C@H](OC(=O)NCCCCCCCCCCCCO)CC[C@@]4(C)C3CC[C@]21C] | 5'C12 |
| Cholesteryl 4-(hydroxymethyl)phenyl-carbamateale | 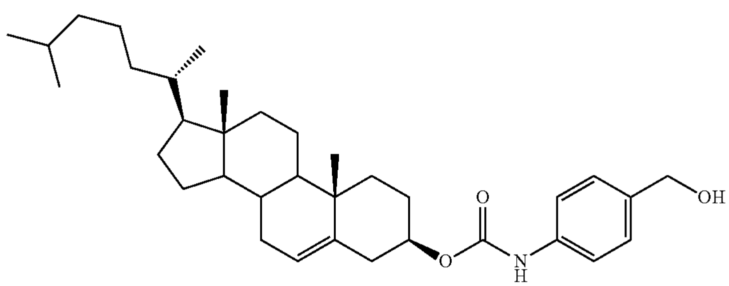 [SMILES: CC(C)CCC[C@H](C)[C@@H]1CCC2C3CC=C4C[C@H](OC(=O)Nc5ccc(CO)cc5)CC[C@@]4(C)C3CC[C@]21C] | 5'ABA |
| Cholesteryl 4-hydroxypiperidine-1-carboxylate | 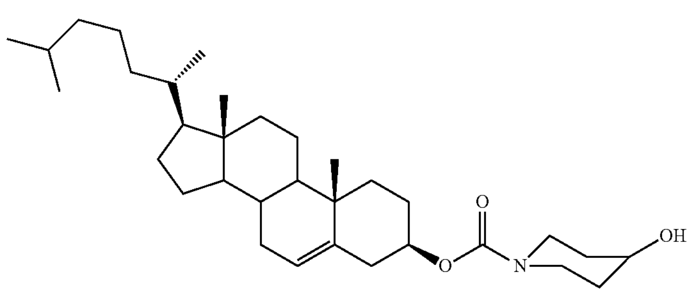 [SMILES: CC(C)CCC[C@H](C)[C@@H]1CCC2C3CC=C4C[C@H](OC(=O)N5CCC(O)CC5)CC[C@@]4(C)C3CC[C@]21C] | 5'PIP |

Table III lists alternative abbreviations used for linker structures and the number of atoms separating the phosphate moiety of the oligonucleotide from the carbamate linkage of the conjugate.

| Compound | Alternate Name | Number of Atoms between the siRNA and conjugate |
|---|---|---|
| C3 | Chol-C3 | 3 |
| PRO | Chol-PRO | 4 |
| C5 | Chol-C5 | 5 |
| PIP | Chol-PIP | 6 |
| ABA | Chol-ABA | 7 |
| C8 | Chol-C8 | 8 |
| Ac-C8 | | 8 |
| Chol-C6-Hp | HP6 | 9 |
| C10 | Chol-C10 | 10 |
| C14 | Chol-C14 | 14 |
| C14-Ac | | 14 |
| C8 + C6 | Chol-C8 + C6 | 15 |
| PEG | Dharm | 16 |
| C8 + C12 | Chol-C8 + C12 | 22 |

Note:
"Ac" represents an acetyl group substituted for the cholesterol group

Example 52

General Techniques

The following general techniques were used in Examples 53-66.

To test the ability of conjugated siRNAs to knockdown gene expression, 2.5-5K cells (96 well format) are plated in media (DMEM) supplemented with 10% fetal calf serum (FCS) and allowed to culture overnight (37° C., 5% $CO_2$). On the following day, the media overlaying the cells is replaced with serum-free media (e.g., Reduced Serum medium, MEM, HyClone) containing the G4 oligonucleotide duplex complex at concentrations ranging from 0.1-2 uM. Passive delivery is allowed to proceed for 4 hours—overnight, followed by media replacement (Media+FCS) and further incubation (generally 48 hr-72 hrs) before gene knockdown is measured.

Conditions for lipid delivery included: 10,000 cells, DMEM, 0.2 ug/well of DharmaFECT 1, 24 hr incubation, 1-100 nanomolar siRNA. For electroporation, delivery conditions included 20,000 cells, DMEM, square wave protocol, 24 hr incubation 133 nanomolar siRNA.

Target genes assessed in many of these studies were (in human cell lines) PPIB (NM_011149) and, GAPDH (NM_001001303) in mouse cell lines. Sequences used in these studies included (for duplexes) hPPIB#3 (sense: 5'ACAG-CAAAUUCCAUCGUGU) (SEQ ID NO: 1), and mGAPDH (sense; 5' CACUCAAGAUUGUCAGCAA) (SEQ ID NO: 2).

In all experiments, overall culture viability was compared with untreated or mock treated cells by Alamar blue (Biosource International) and assessed for target knockdown using branched DNA (BDNA, Genospectra). Human cell lines used in these studies included non-adherent cell lines THP-1, and Jurkat, and adherent cell lines SHSY5Y, HeLa, HeLa-S3, MCF10A, 293T, MCF7, and HuVEC. For mouse cell line studies, 3T3 NIH and ES-D3 cells (both adherent cell types) were employed.

Global Gene Profile Analysis

The following protocol is used for assessing the gene profile of cells transfected with siRNA.

1. Collecting Samples

The wells designated for microarray analysis are aspirated to remove media. Cells are then lysed using (70 ul) RLT buffer (Qiagen, Cat. #79216) with a 1:100 dilution of beta-mercaptoethanol as per the manufacturer's instructions. Identical wells are pooled and samples are stored at −80° C. if total RNA purification is not conducted on the same day.

Wells dedicated to assessing transfection efficiency are evaluated for 1) siRNA-mediated knockdown of positive and negative control target genes using bDNA (Quantigene: Panomics, Fremont, Calif.), and 2) culture viability using the alamarBlue™ assay (Biosource, Intl, Camarillo, Calif.). These two assays are compatible and can be run on a single plate. Transfections that pass both viability (90-95% viability) and knockdown thresholds (90% normalized knockdown of a positive control siRNA) are acceptable for microarray analysis.

2. Assessing Quantity and Quality of RNA for Expression Profiling

Total RNA is isolated from lysates using Qiagen's RNeasy Mini columns with on-column DNase digestion as per the manufacturer's protocol (http://www1.qiagen.com/literature/handbooks/PDF/RNAStabilizationAndPurification/FromAnimalAndPlantTissuesBacteriaYeastAndFungi/RNY_Mini/1035969_HB_BenchProtocol.pdf). Total RNA concentration is assessed by NanoDrop (NanoDrop, Wilmington, Del.) and samples are diluted to 100 ng/ul (typical yields>100 ng/ul). If necessary, samples can be stored at −80° C. Total RNA quality is assessed using a 2100 Bioanalyzer (Agilent, Santa Clara, Calif.) with the RNA 6000 Nano Lab-Chip. Acceptable samples should have an RNA Integrity Number (RIN) of at least 9 and can be stored at −80° C.

3. RNA Amplification and Labeling

Total RNA is amplified and labeled using the Low Input RNA Fluorescent Linear Amplification Kit (Agilent, Santa Clara, Calif.) according to the manufacturer's protocol (http://www.chem.agilent.com/). Cy5 CTP and Cy3 CTP are obtained from Perkin Elmer (Wellesley, Mass.). Typically, 650 ng of total RNA is used per reaction. Experimental samples are labeled with Cy5 while mock (lipid-treated) samples are labeled separately with Cy5 and Cy3. Untransfected samples are labeled with Cy3. Excess dye is removed from the labeled samples with Qiagen RNeasy Mini columns, implementing the two, one minute "dry" spins described in the Agilent protocol.

Yields of labeled samples are quantified with a NanoDrop instrument (NanoDrop). Typical yields are 300-500 ng/ul starting with 650 ng of total RNA and should be uniformly colored depending upon the fluorophore (pink for Cy3, blue for Cy5). Dye incorporation can be assessed by measuring the respective dye wavelengths (Cy3: 550 nm, Cy5: 650 nm) with the "microarray" protocol on the NanoDrop instrument.

4. Hybridization and Scanning

Hybridizations to Human 1A (V2) microarray (Agilent) are performed according to the manufacturer's instructions using 750 ng of each Cy5 and Cy3 labeled sample per array. Samples include:

i) Each siRNA-transfected sample (Cy5) is hybridized along with the mock-transfected (Cy3-labeled) sample as a reference.

ii) A control array for gene expression effects of transfection is assembled by using mock-transfected (Cy5) and untransfected (Cy3) samples.

iii) A control array for assessing signal/expression levels in the absence of siRNA treatment as well as for determining dye-biased targets is assembled with mock-transfected (Cy5) and mock-transfected (Cy3) (a self-self array).

After a 17-20 hour hybridization at 60° C., arrays are washed in 6× and 0.06×SSPE with 0.025% N-lauroylsarcosine. Subsequently, arrays are submersed in acetonitrile and washed in non-aqueous drying and stabilization buffer (Agilent). Arrays are analyzed using Agilent's model G2505B array scanner and raw .tiff images are processed according to the default protocols in Feature Extraction v 9.1.

5. Data Analysis

Data analysis is initiated in Microsoft Excel. A flat text file is constructed of feature identifier columns (Feature Number, Row, Column, Control Type, Gene Name, Systematic Name, and Description if available) and selected data columns for each sample (Log Ratio, PValue LogRatio, gProcessedSignal, rProcessedSignal, gIsWellAboveBG, rIsWellAboveBG). The processed data for saturated signals from the mock-mock array are recorded in separate columns (saturated green (gIsSaturated) and red signals (rIsSaturated), respectively) along with a column for the Log of combined red and green signals (gProcessedSignal+rProcessedSignal) computed from the mock-mock array.

Further analysis is conducted in Spotfire DecisionSite 8.2 using the Functional Genomics Module. The data is first filtered by control probes and low signal/low expression probes to eliminate sequences for which it would be difficult to accurately determine a 2-fold reduction in signal (LogRatio −0.3). This is achieved by filtering probes for which the Log (combined signal) from the mock-mock array is below 2.8, or approximately 630 pixels. The absolute range of processed signals should be assessed among all of the arrays in a batch to make sure that each hybridization was successful. Probes which exhibit saturation in either channel in the mock-mock array are also removed. Typically, by employing these procedures, the probe set available for analysis is reduced from 21,073 to approximately 13,000-15,000 probes.

Probes that do not change more than twofold in any sample (−0.3<LogRatio<0.3) are removed. The remaining probes are plotted on a heatmap after unsupervised hierarchical clustering (unweighted average, Euclidean distance, average value). Further comparison of siRNA-treated sample columns with mock-mock and mock-untransfected hybridizations, allows probes that appear to be differentially expressed in either of these control arrays or those that are inherently noisy (for instance, LogRatio versus mock of <−0.2 in three or more arrays in an experiment) to be discarded.

In all the following Examples, the overhang on the G4 siRNA is a UU overhang.

Example 53

Identifying Preferences for 5' vs 3' Terminal Modifications

Initial studies were performed to determine how linkage of a cholesterol group to either the 5' or 3' terminus of the sense strand of an siRNA altered performance. Mouse 3T3 NIH cells were grown under prescribed conditions and subsequently subjected to cholesterol conjugated siRNA (duplex, mGAPDH 20: 5'-CACUCAAGAUUGUCAGCAA-3') (SEQ ID NO:3) at three concentrations (500 nM, 1 uM, and 5 uM). In these instances, the linker used was the PEG linker having 16 atoms separating the oligonucleotide and the cholesterol conjugate.

Figure 8A:
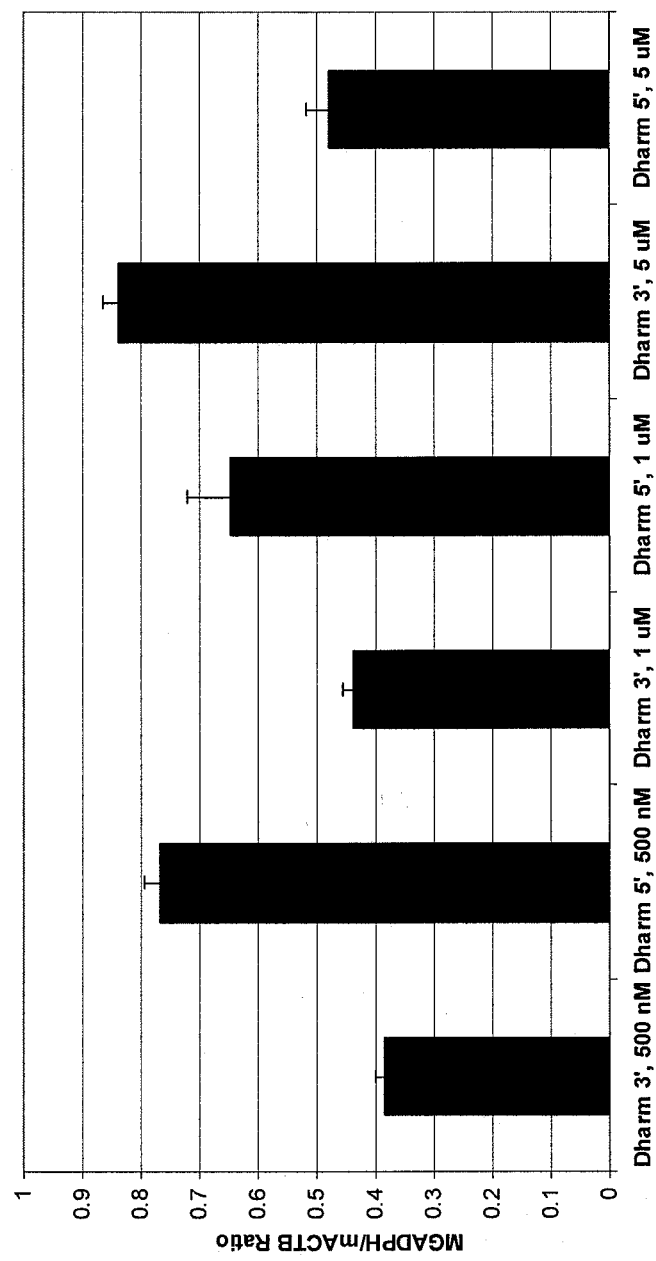
FIG. 8A is a bar graph that shows the relative functionality of duplexes having 5' and 3' sense strand conjugate attachment. Data represents the performance at 500 nanomolar, 1 micromolar, and 5 micromolar concentrations, and show the greater performance of 3' sense strand conjugates at low concentrations.

Results of these experiments are presented in FIG. 8A and demonstrate that at the lowest concentrations (500 nM, 1 uM) attachment of the cholesterol to the 3' terminus of the sense strand preserved siRNA functionality better than attachment to the 5' terminus (see boxed areas). None of the constructs induced significant levels of toxicity (data not shown).

Figure 8B:
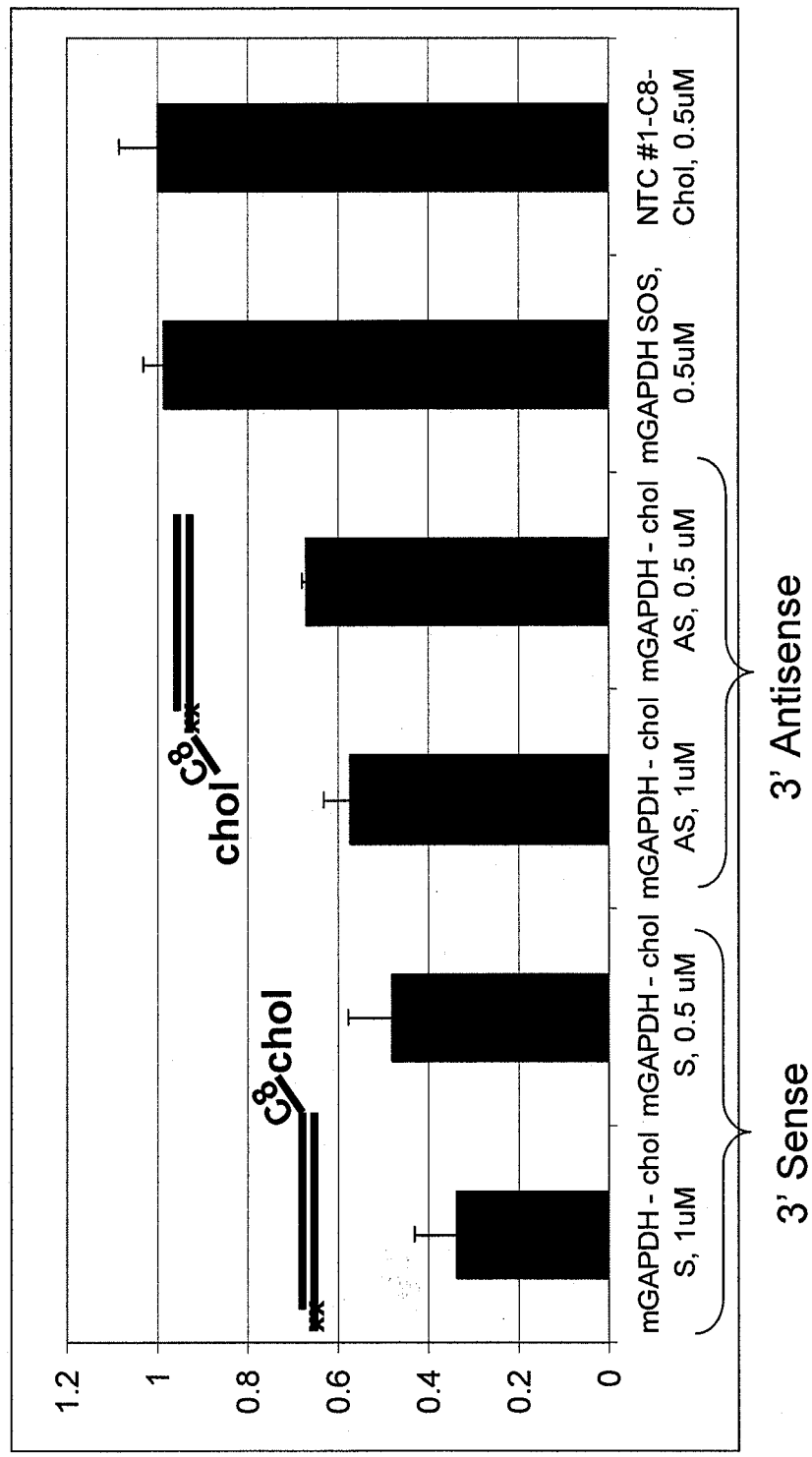
In FIG. 8B, duplexes having a 3' sense strand or 3' antisense attachment of cholesterol conjugates (at 1 micromolar and 0.5 micromolar concentrations) are compared. Results demonstrate that 3' sense strand conjugates provide greater levels of gene knockdown than 3' antisense strand conjugates. Y axis represents the fraction of expression. "x" represents positions of phosphorothioate internucleotide modifications. mGAPDH SOS represents a GAPDH targeting molecule that has no cholesterol conjugate. The SOS modification pattern includes 2'-O-methyl modification of all Cs and Us of the sense strand, 2' F modification on all Cs and Us of the antisense strand, a 5' phosphate group on the 5' terminus of the antisense strand, and 2'-O-methyl modification of positions 1 and 2 of the sense strand (counting from the 5' terminus). "NTC #10C8-Chol" represents a non-targeting control duplex that is modified with cholesterol via a C8 linker. Tables I and II show structures for various linkers.

In addition, studies were performed to compare the performance of duplexes having the conjugate on the 3' end of the sense strand vs the 3' end of the antisense strand. In these instances, the linker used was C8. Results are presented in FIG. 8B and clearly show a 3' sense preference for this construct. For these reasons, many of the subsequent studies employed linker-conjugates in the 3' sense position.

Example 54

Identifying Preferred Linker Lengths for Cholesterol-Mediated Delivery of Nucleic Acids To identify the preferred linker length for cholesterol mediated delivery of nucleic acids, siRNA duplexes targeting mouse GAPDH were synthesized with 3' sense strand cholesterol conjugate having a range of linker lengths. Linker sequences included those listed in Table I (see above). Sequences were then compared by transfecting them into cells by passive, lipid-mediated, and electroporation protocols. In addition, to measure the contribution of the cholesterol to passive transfection (as compared to the linker alone) a C14-acetyl group linker was included in the study.

Figure 9:
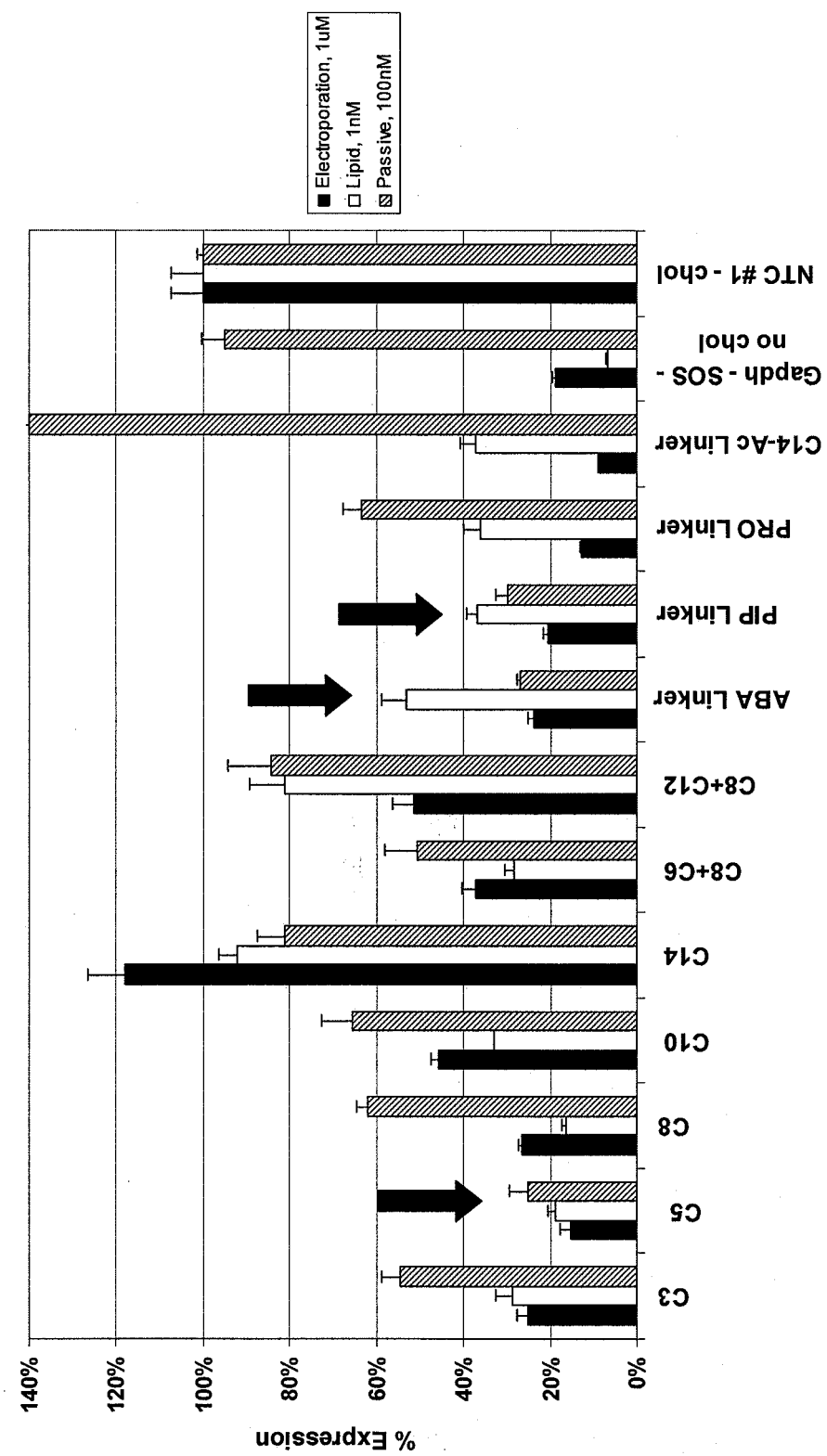
FIG. 9 shows a comparison of linkers of varying lengths. Molecules were introduced into cells using electroporation, lipid mediated delivery, or passive delivery. Linkers with 5 (C5), 6 (PIP) and 7 (ABA) atoms separating the oligonucleotide and the conjugate (see arrows), exhibit greater performance. Y axis represents the percentage of expression.
Figure 10A:
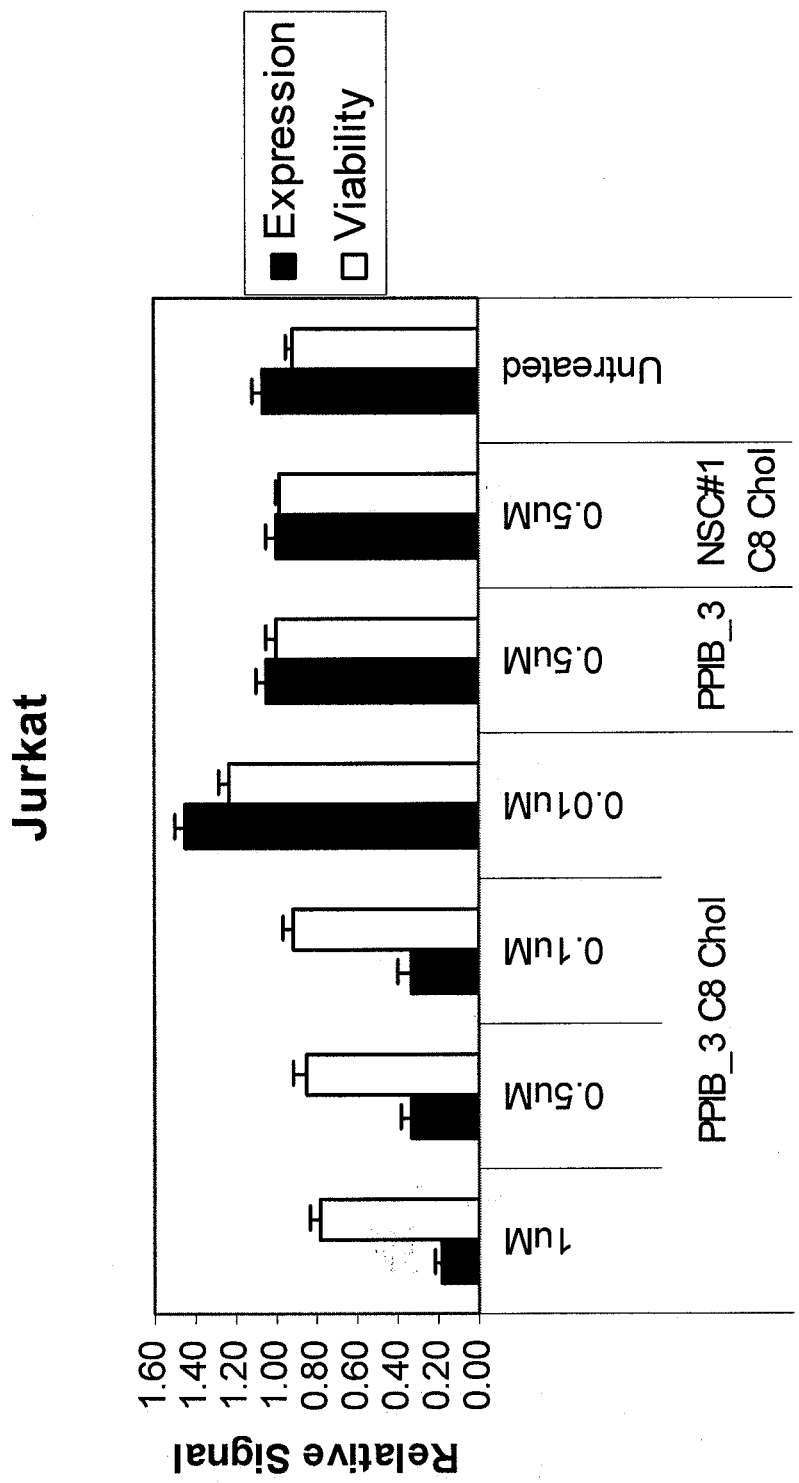
FIG. 10A-E show the performance of cholesterol-conjugated molecules in a range of mouse and human cell types including Jurkat, SHSY5Y, HUVEC, ES-D3 stem cells, 3T3 NIH cells. PPIB-3 siRNA targets the human PPIB gene. mGAPDH is an siRNA targeting mouse GAPDH. NSC#1 is the non-specific control. C8 refers to the linker length (see Tables I and II). Chol refers to cholesterol. Expression was monitored using branched DNA assays (BDNA, Genospectra). Viability was measured using Alamar Blue assay. The results demonstrate the designs of the disclosure provide strong silencing in a wide range of cell types.
Figure 10B:
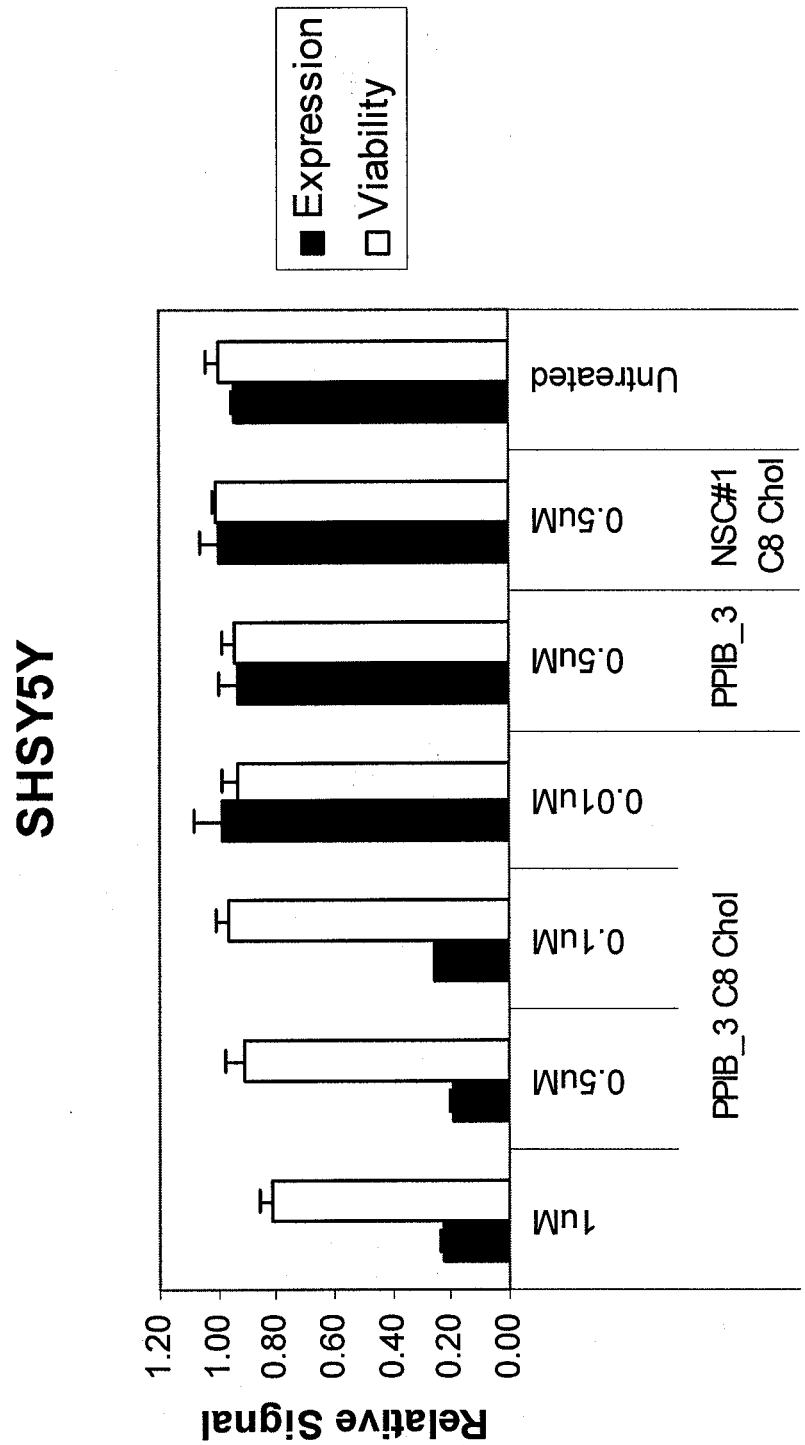
Figure 10C:
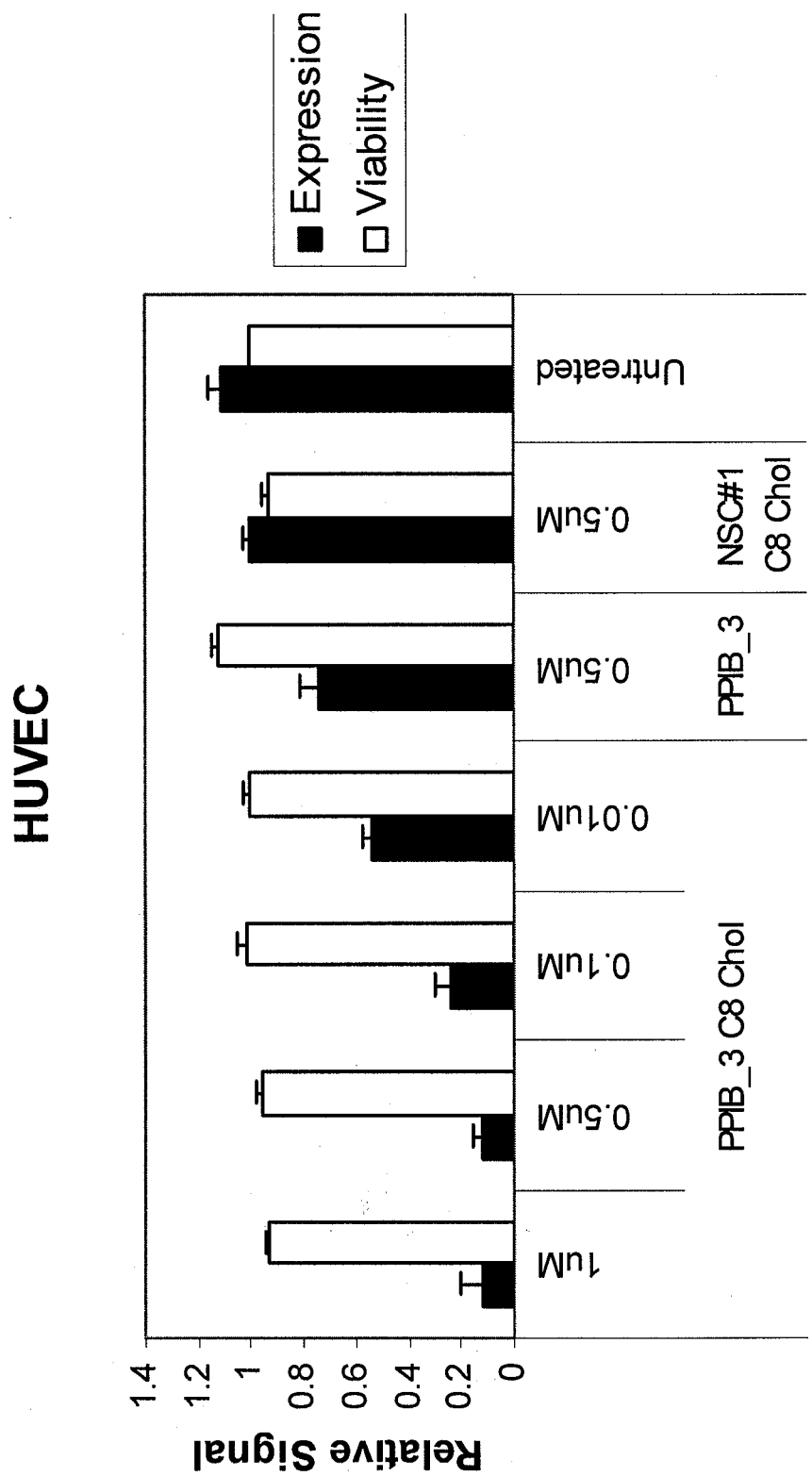
Figure 10D:
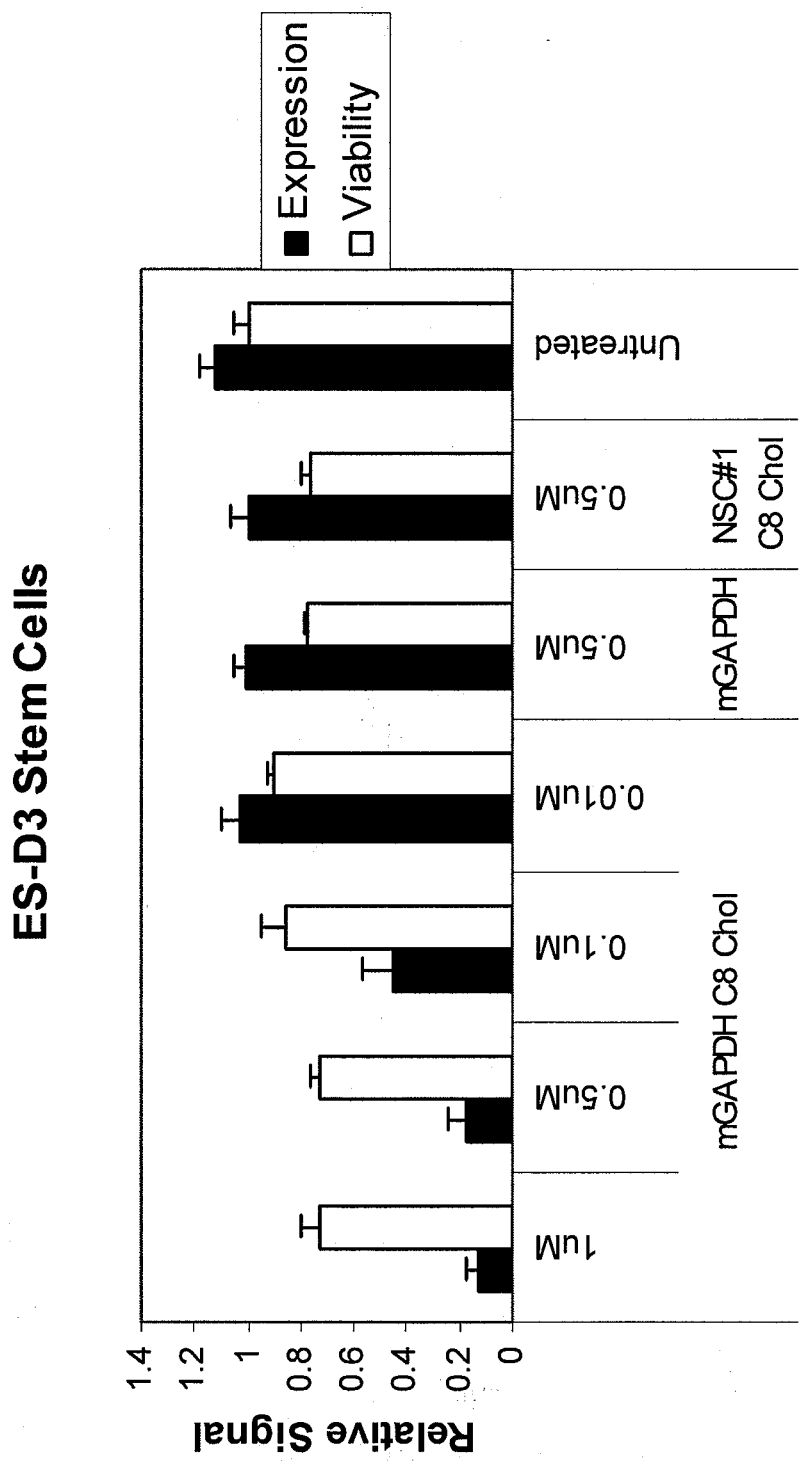
Figure 10E:
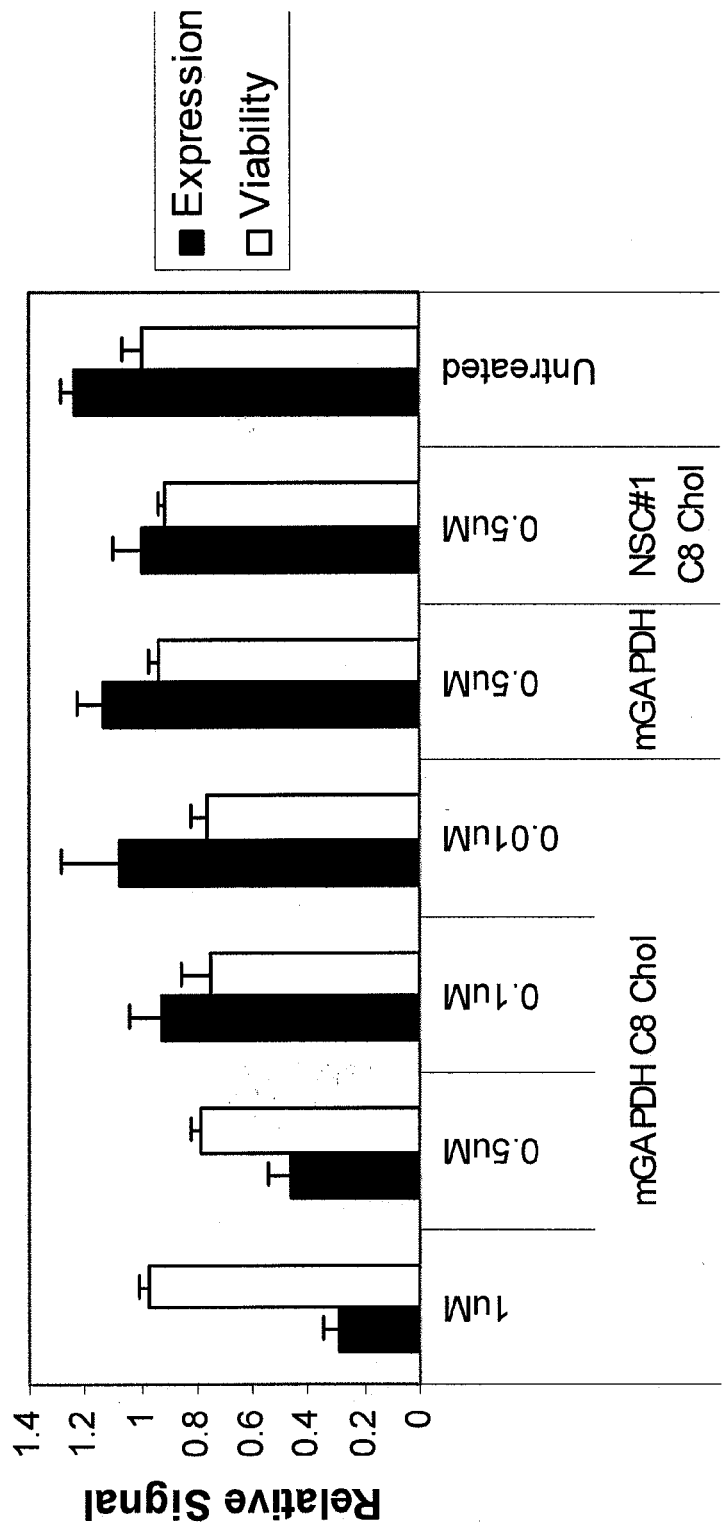

Data presented in FIG. 9 shows that a small window of linker lengths performed best in all three delivery systems. Specifically, the C5 linker, the PIP (C6) linker, and the ABA (C7) linker exhibited superior performance. C3 and C8 linkers also performed well under certain conditions. These studies identify linkers that have atom lengths of 4-8, and particularly lengths of 5-7, as the preferred lengths for nucleic acid-cholesterol applications.

To test the application of these designs in passive delivery on a range of cell types, the siRNAs targeting mouse and human genes and having a 3' cholesterol conjugate (C8 linker) were tested in a range of human (non-adherent and adherent) and mouse (adherent) cell types at concentrations ranging from 0.01-1 micromolar.

The results of these experiments are shown in FIG. 10A-E and demonstrate an applicability of smaller (C8) linker lengths to a wide range of both adherent and non-adherent, human and non-human cell lines. Results were similar regardless of the whether the cell density was 2,500 or 10,000 cells per well.

Example 55

Modified Internucleotide Linkages

To test the effect of stabilizing the overhangs in passive delivery, siRNA targeting mouse GAPDH and having a C8 linker on the 3' end of the sense strand conjugated to cholesterol, were synthesized with and without phosphorothioate internucleotide linkages on the overhang. Mouse 3T3 NIH cells (2,500 cells per well) were then exposed to the molecules in a reduced serum background at 0.5 and 1 micromolar concentrations.

Figure 11:
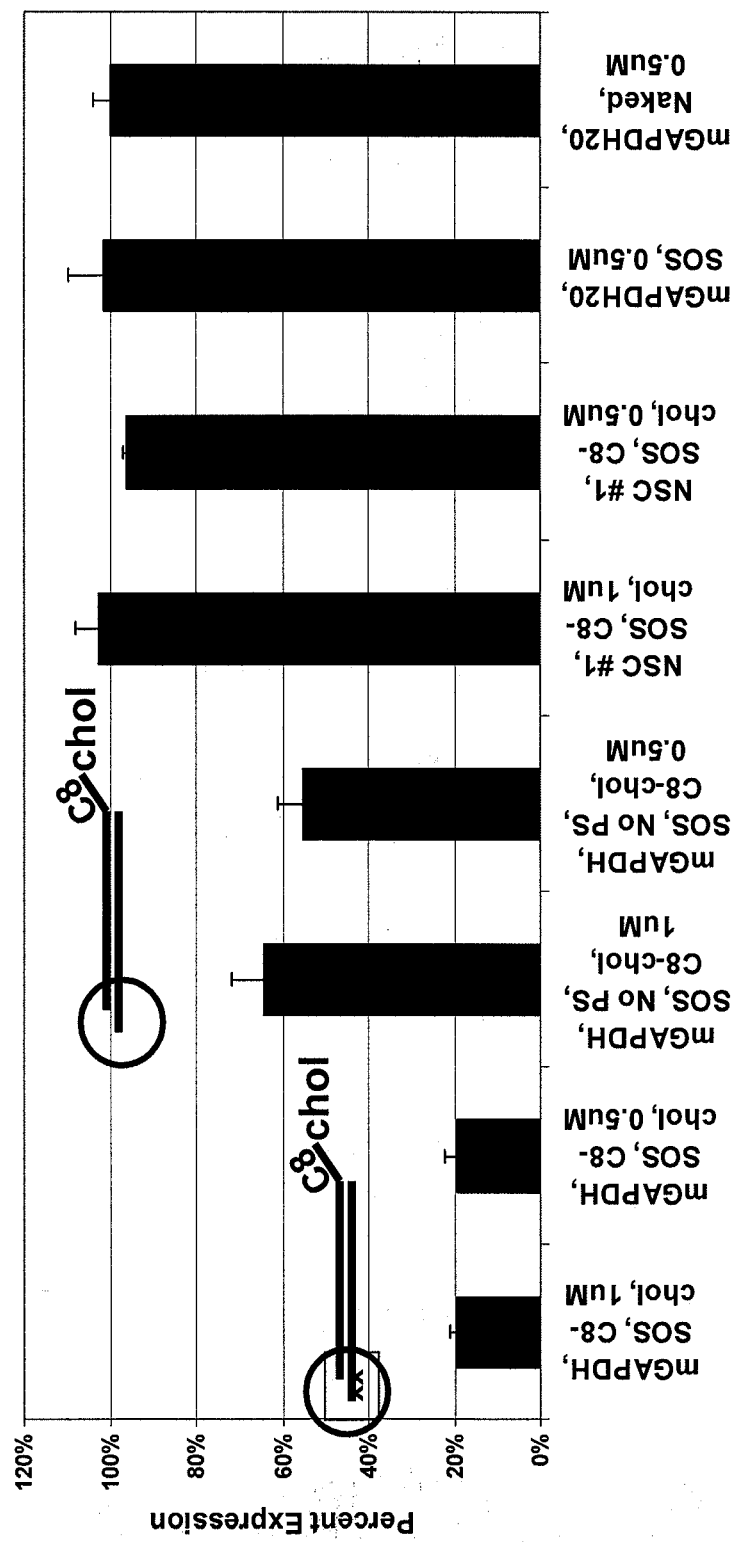
FIG. 11 depicts the differences in functionality of constructs that are unmodified vs having modified internucleotide linkages (i.e. phosphorothioate modifications) in the 3' overhang of the antisense strand. Where indicated, molecules contain an SOS modification pattern which includes 2'-O-methyl modification of all Cs and Us of the sense strand, 2' F modification on all Cs and Us of the antisense strand, a 5' phosphate group on the 5' terminus of the antisense strand, and 2'-O-methyl modification of positions 1 and 2 of the sense strand (counting from the 5' terminus). Results clearly show that incorporation of stabilized internucleotide linkages enhances overall functionality. NSC represents non-specific control sequence. "Naked" refers to unmodified duplexes.

The results of these studies are presented in FIG. 11 and show that addition of the stabilizing modifications in the 3' overhang of cholesterol conjugates having a C8 linker greatly enhanced the functionality of the molecule.

Example 56

Demonstration that the Increase in Functionality is the Result of the Conjugate and not the Linker To determine whether the observed lipid-independent delivery of duplexes having linkers and cholesterol was the consequence of the linker alone, the functionality of siRNA targeting GAPDH and having a C8-Cholesterol (3' terminus of the sense strand) were compared with identical siRNA having the C8 or C14 linkers terminated with an acetyl group (i.e. no cholesterol). Conditions for transfection were similar to those previously described (2.5 k 3T3 NIH, 72 hours, Hy-MEM-RS) and gene knockdown was measured by branched DNA using ACTB for normalization.

Figure 12:
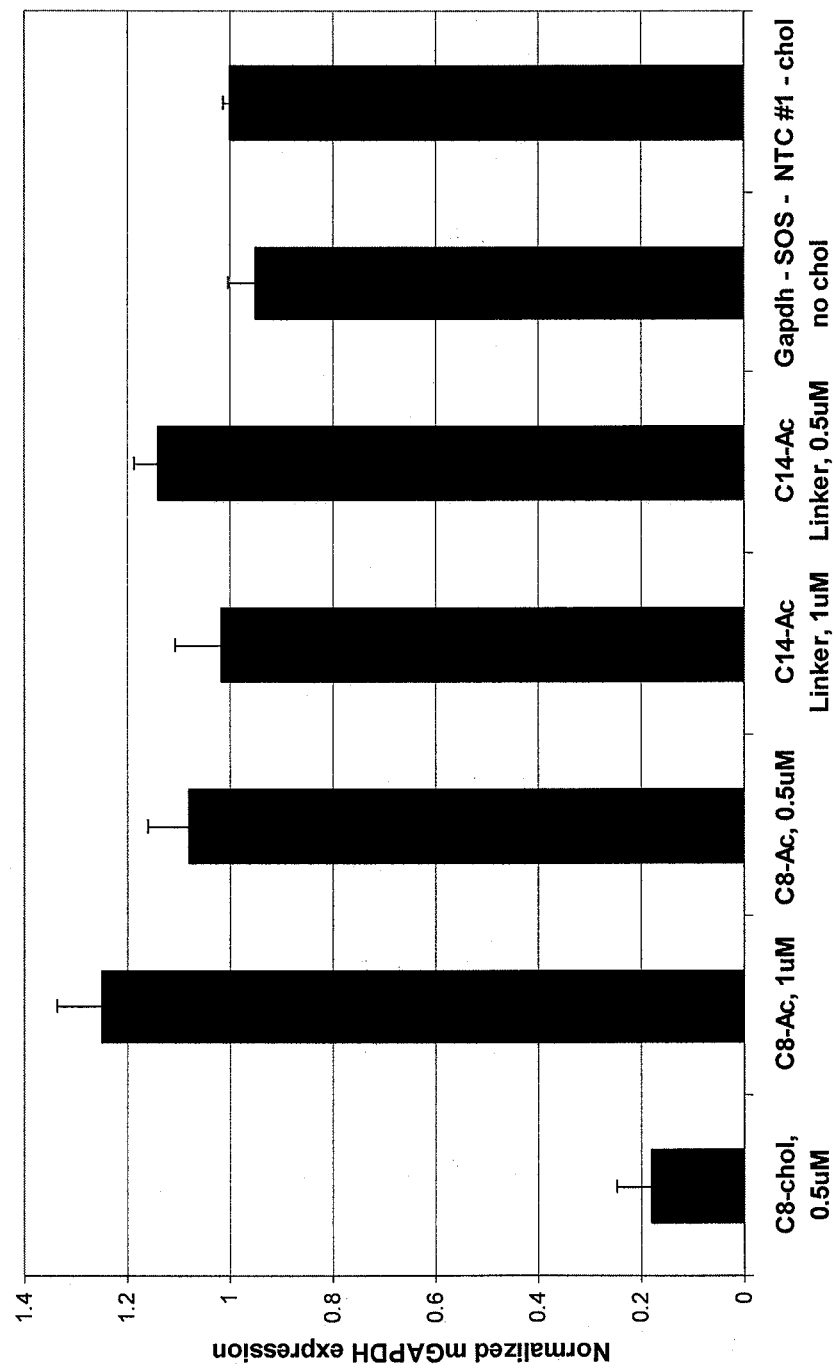
FIG. 12 compares the performance of duplex molecules having C8 or C14 linkers (capped with acetyl groups) with duplexes that have a C8 linker conjugated to cholesterol. "NTC"=a non-targeting control sequence. "Ac" represents acetyl cap on a linker. "SOS" is a modification pattern which includes 2'-O-methyl modification of all Cs and Us of the sense strand, 2' F modification on all Cs and Us of the antisense strand, a 5' phosphate group on the 5' terminus of the antisense strand, and 2'-O-methyl modification of positions 1 and 2 of the sense strand (counting from the 5' terminus). "Chol" represents cholesterol. Results clearly demonstrate that cholesterol conjugation is highly effective and that a simple acetyl cap is not effective for delivery and gene silencing.

Results of these studies are shown in FIG. 12 and show that while cholesterol linked GAPDH siRNA provide strong knockdown (~80%) at 0.5 micromolar, duplexes having the linker alone (e.g. C8-Ac, C14-Ac) provide no knockdown at either 0.5-1.0 micromolar concentrations. These results clearly show that it is the combination of the linker molecule and the conjugate (cholesterol) that are responsible for the observed non-lipid mediated delivery.

Example 57

Figure 13A:
FIG. 13A depicts a wide array of chemical modifications that have been applied to cholesterol conjugated duplexes having the C8 linker.

Testing Multiple Chemical Modification Patterns with Duplex Designs Identifies Unique Combinations that Enhance Functionality To identify unique combinations of chemical modifications that can be added to siRNA duplexes to enhance functionality, duplexes targeting PPIB and GAPDH and having a C8-cholesterol on the 3' end of the sense strand were synthesized with the list of sense and/or antisense modification patterns listed in FIG. 13A. Molecules were then introduced into the appropriate cell type (e.g. HeLa or NIH 3T3 cells) at 0.5 micromolar concentrations, in the absence of lipid and assessed for gene knockdown at the 72 h time point.

Figure 13B:
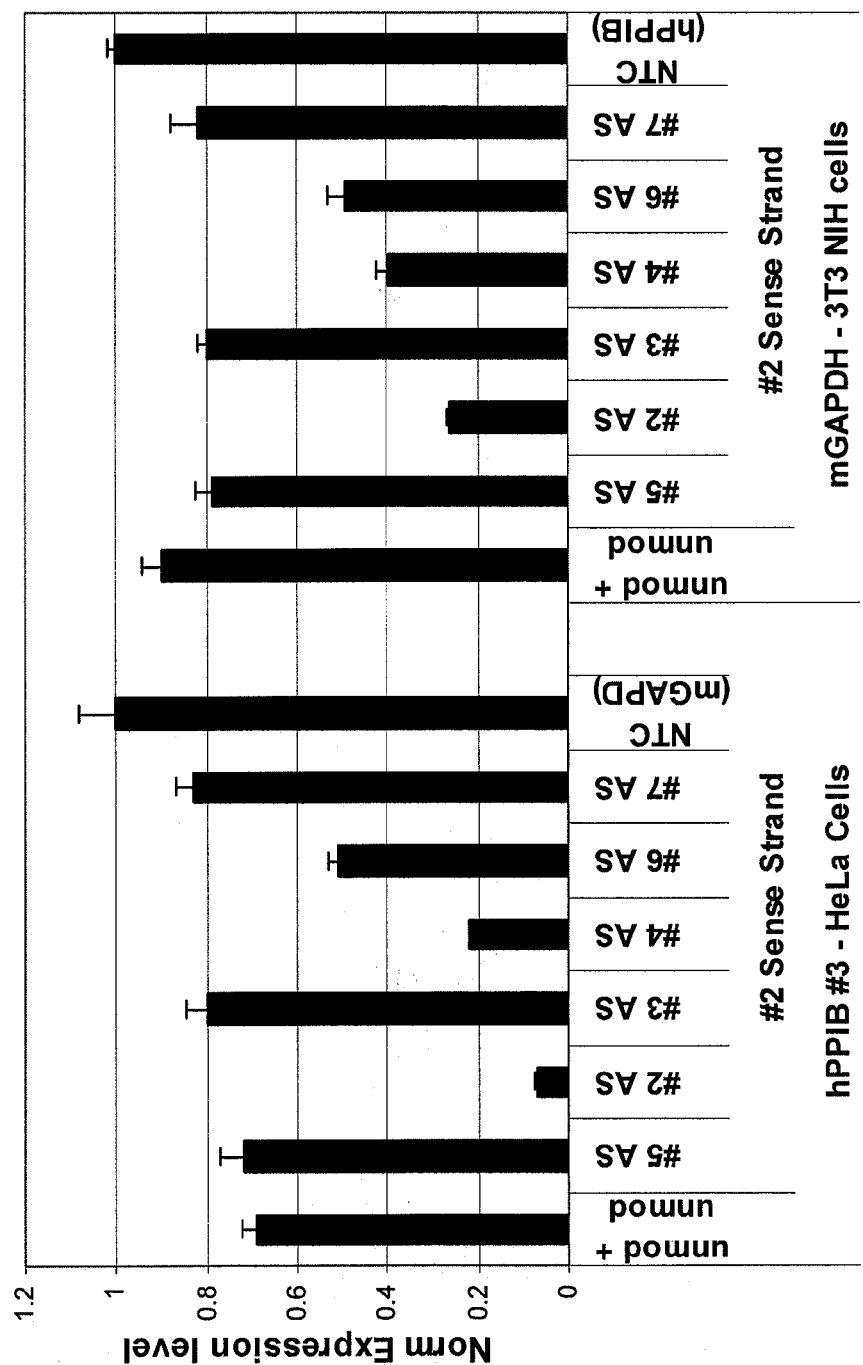
FIG. 13B shows the functionality of PPIB and GAPDH targeting duplexes in human (HeLa) and mouse (3T3 NIH) cells having the modifications listed in FIG. 13A.

The results of these studies are presented in FIG. 13B and demonstrate that the most heavily modified (i.e. stabilized) siRNAs are the most potent for this form of delivery. In particular, molecules containing 2'-O-methyl on all Cs and Us of the sense strand, plus 2'-O-methyl modification of the first two nucleotides of the sense strand, plus 2' F modification of all Cs and Us of the antisense strand, plus phosphorothioate modification of the internucleotide linkages of the 3' overhang of the antisense strand provided the best performance (75-95% knockdown). As shown previously in Example 55, addition of a phosphorothioate internucleotide modification in the 3' overhang of the AS significantly enhanced activity, thus a stabilized overhang is deemed to be preferred for activity. In none of the experiments was toxicity found to be an issue.

Example 58

Kinetics of G4 Mediated Knockdown

Experiments were performed to better understand the kinetics of gene knockdown mediated by passive delivery of G4 siRNA. In the first study, HeLa cells (2.5K cells per well in a 96 well plate) were exposed (for times indicated) to G4 siRNA (specifically, G4 (–mm) siRNA) targeting P53 (0.1-1.0 uM) in serum-free media (sense strand 5'GCUUC-GAGAUGUUCCGAGA3') (SEQ ID NO: 4). Subsequently, the level of P53 gene knockdown was measured at 24, 48, and 72 hr to identify the time point at which optimal gene knockdown is observed.

Figure 14A:
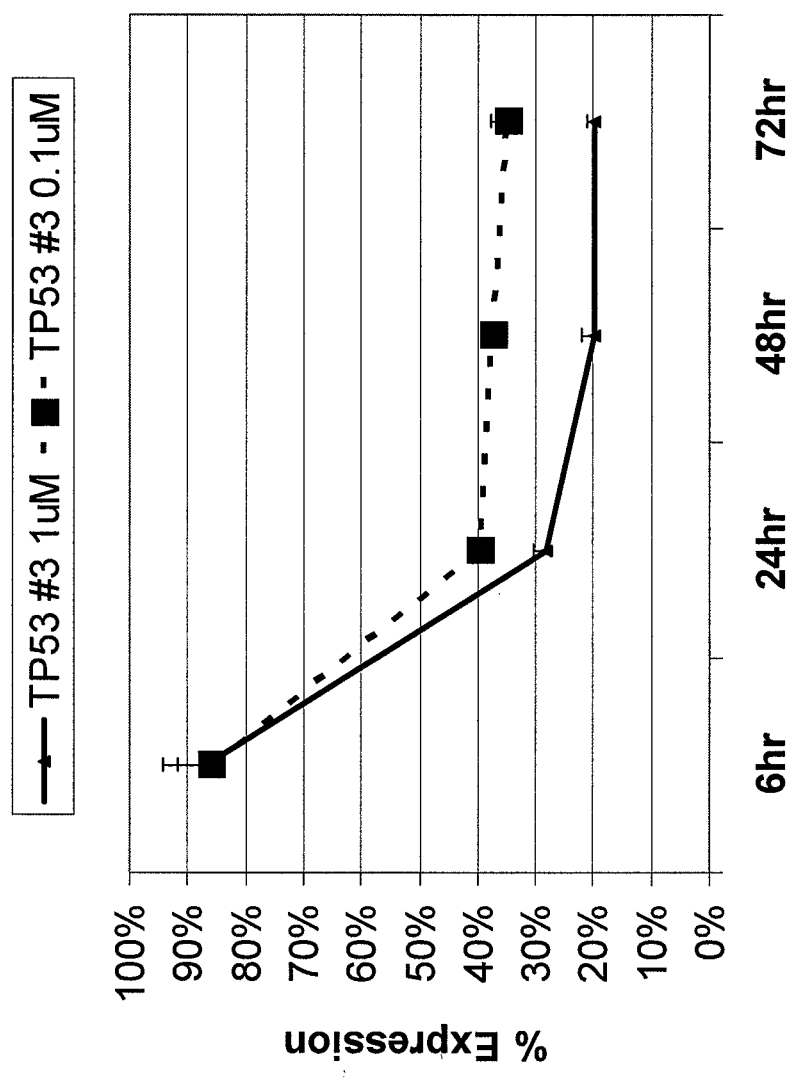
FIG. 14A demonstrates the kinetics of gene knockdown during passive delivery. A TP53-targeting G4 siRNA was transfected into HeLa cells at 0.1 and 1.0 uM concentrations. The graph shows that gene knockdown peaks at 72 hours.

Results of these experiments are presented in FIG. 14A and demonstrate that the kinetics of gene knockdown were similar for both conditions. Roughly 60% gene silencing was observed at the 24 hr time point with the level of knockdown reaching a peak (~70-80% KD) at 72 hours. These findings demonstrate that a single dosing of cells with G4 siRNA can rapidly knockdown gene expression.

Figure 14B:
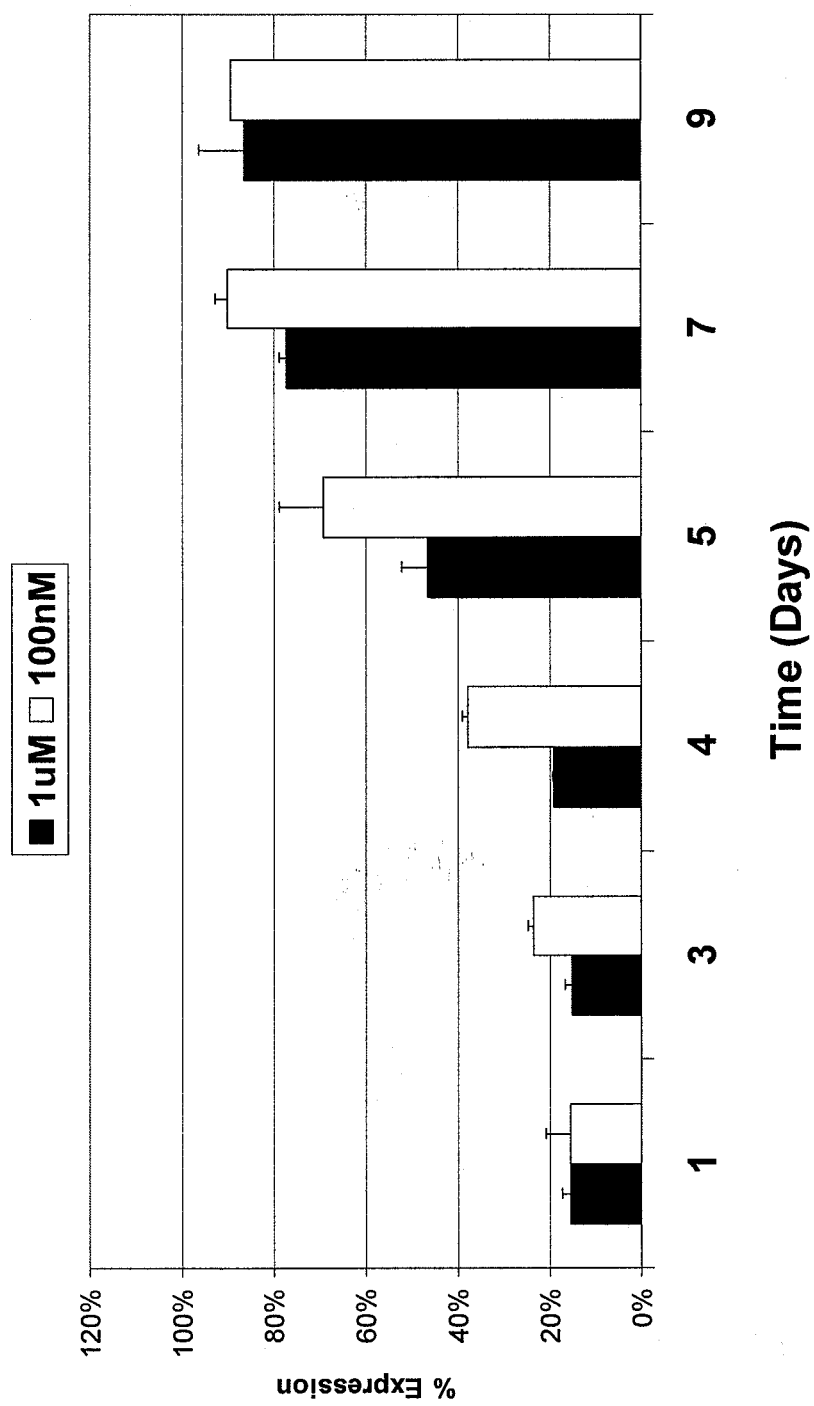
FIG. 14B demonstrates the longevity of gene knockdown induced by G4 siRNA. PPIB-targeting G4 siRNA was introduced into HeLa cells by passive delivery. The graph demonstrates that at the 1 uM concentration, >75% silencing is sustained for at least 4 days. For both FIG. 14A and FIG. 14B, Y axis represent fraction of the target gene expressed. X axis represents the number of hours after delivery.

Parallel experiments designed to test the longevity of knockdown using G4 siRNA were performed. G4 siRNA targeting PPIB (specifically, a G4 (–mm) siRNA) was introduced into cells at 0.1 and 1.0 uM concentrations in reduced sera media (sense strand 5'-ACAGCAAAUUCCAUCGUGU 3') (SEQ ID NO:5). After twenty-four hours, media was switched to complete media (10% FCS) and the level of PPIB knockdown was assessed on days 1, 3, 4, 5, 7, and 9. Results of these studies show that a single dosing of G4 siRNA at the 1.0 uM concentration provide 80% or better knockdown for a minimum of 4 days (FIG. 14B) thus demonstrating that G4 siRNA delivered in this fashion can induce potent silencing for extended periods.

Example 59

An Investigation of the Innate Immune Responses and Off-Target Effects Induced by G4

Introduction of siRNAs into cells by lipid-mediated transfection has been shown to induce both non-specific (innate immunity) and specific (off-targeting mediated) responses. As these effects can be detrimental to the interpretation of experimental data, global gene profiling and Searchlight cytokine arrays were utilized to compare and contrast lipid-mediated delivery of siRNA with passive delivery of G4 siRNA.

Innate Immune Response

G4 siRNA targeting PPIB (specifically, G4 (–mm)) were passively introduced into cells at 0.1 and 1.0 uM concentrations. After 72 hrs cells were harvested and mRNA was purified for global gene profile analysis (see protocol above). In parallel with these experiments, the same sequences were synthesized without the Chol-05 and transfected into cells (0.1 uM) using Lipofectamine 2000 (a lipid). Twenty-four hours after transfection, messenger RNA samples were similarly prepared and assessed by genome profiling.

Figure 15A:
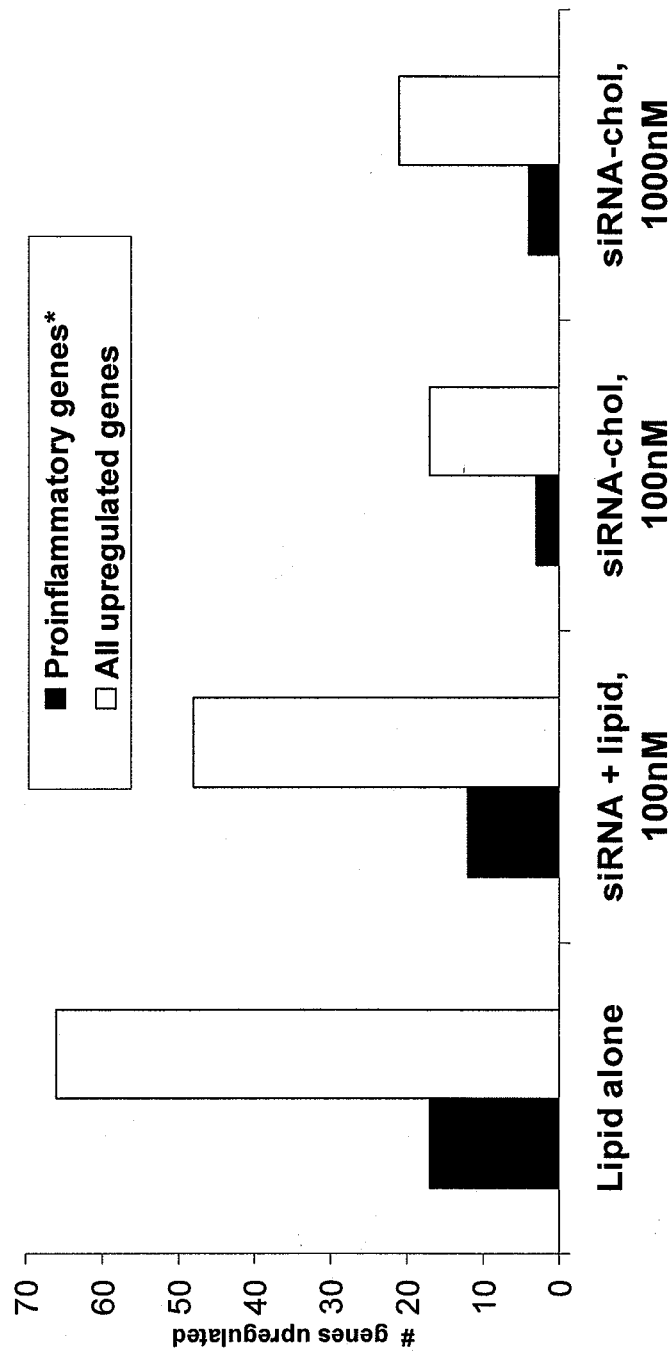
FIG. 15A provides a graph that quantitates the number of genes that are induced under each of the conditions including passively-delivered G4 siRNA at 100 and 1000 nM (siRNA-chol), lipofectamine 2000 mediated delivery (100 nM), and lipid treatment alone. Y axis represents the number of genes that are up-regulated. White bars represent the total number of upregulated genes. Black bars represent numbers of genes that are proinflammatory.

Lipid treatment alone and lipid+siRNA induced upregulation of ~50-70 genes by two-fold or more (see FIG. 15A). Many of these genes were associated with the pro-inflammatory response (e.g., CFHR5, IF127, IL6, DDX58, IL8, IL1F9, ENST, CXCL1, G1P2, IFNGR1, IFIT2, IFIT1, CCL8, CXCL1, SERP1, CXCL3, HMOX1) suggesting exposure of cells to lipid and lipid+siRNA mixtures induces cellular stress.

Passive delivery of siRNA using G4 siRNA at either concentration induced only a fraction of this response observed with lipid-mediated delivery. The total number of genes upregulated by G4 siRNA-treated cultures was less than a third of that observed in lipid mediated delivery (FIG. 15A). Moreover, only 3-4 pro-inflammatory genes were found in this collection, suggesting this method of delivery traumatized cells to a far lesser degree.

Further quantitation of the innate immune response resulting from lipid mediated delivery of siRNA and passive delivery of G4 siRNA included analysis of IL6 and IL8 responses using SearchLight™ array technologies (Pierce Biotechnology). Specifically, 2.5 K HeLa cells were treated with 1) one of four G4 siRNAs (-mm), 2) a 21 bp siRNA (100 nM, lipid delivery), or 3) lipid alone, in reduced serum media (see Table III below for sequences). In addition, a 29 bp siRNA that was known to induce a cytokine response was included in the study as a positive control. After 72 hours, the level of IL6 and IL8 was assessed in the media according to manufacturer's instructions (see http://www.endogen.com/).

TABLE III

Sequences used in Example 59

| Molecule | Sense Strand Sequence 5'→3' | SEQ ID NO: |
|---|---|---|
| G4#1 | GAUGGUGGGAAUUCGGGAA | 6 |
| G4#2 | UGUUGGACUUCACGGGCAA | 7 |
| G4#3 | GGAUAUGAGAGACUGGAUU | 8 |
| G4#4 | CCAUACGGCUCUAACAGAU | 9 |
| 29 mer | UGGAAUGAGCUGAAAGGGACUUCCAAGGA | 10 |
| 21 mer | GAUGGUGGGAAUUCGGGAA | 11 |

Figure 15B:
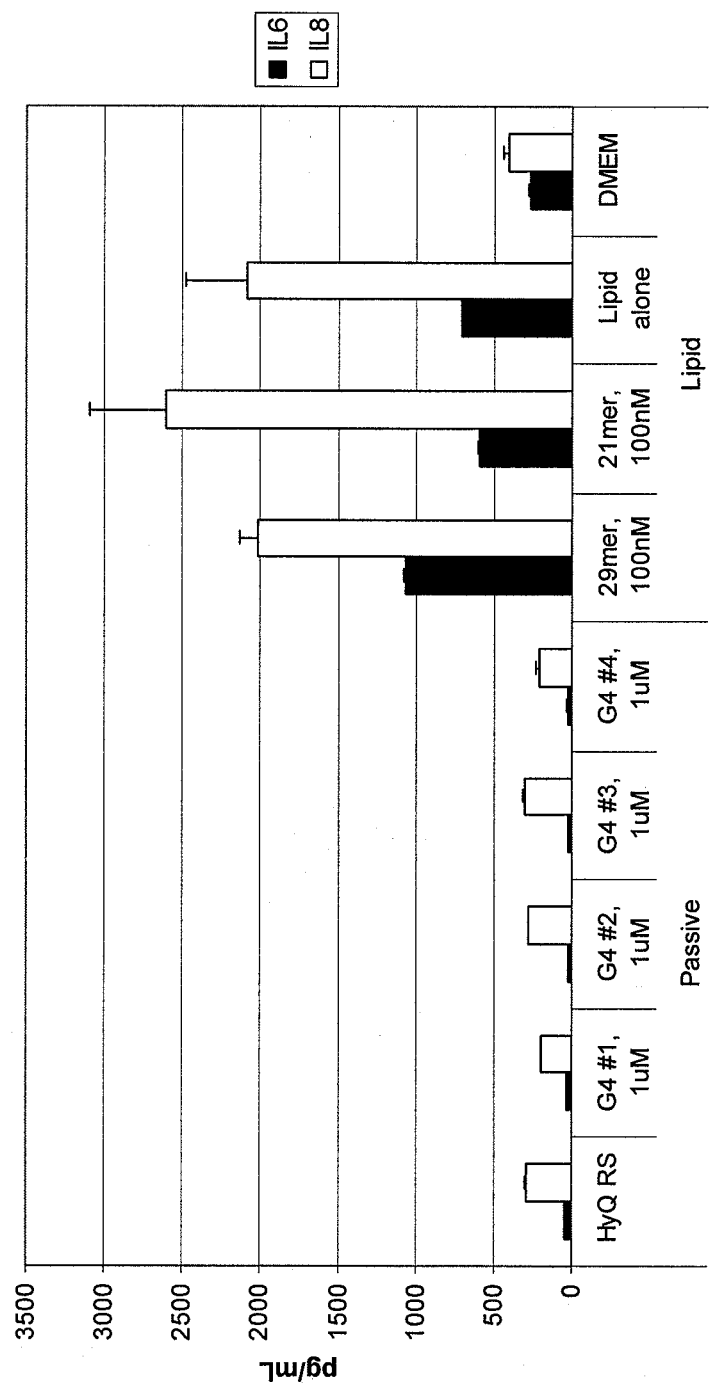
FIG. 15B provides a graph that quantitates the levels of IL6 and IL8 induction during G4-(passive) and lipid-mediated delivery of siRNAs. "HyQRS" represents reduced serum media. "G4#1-4" represent four distinct G4-siRNAs. "29mer" represents a 29 basepair duplex that induces strong IL6 and IL8 responses. "21 mer" represents a 21 bp duplex delivered by lipid transfection. The results show that while lipid-mediated delivery of siRNA induces strong IL6 and IL8 cytokine responses, passive delivery of G4 siRNA does little to induce the innate immune response. Y axis represents the picograms of IL6 or IL8 found in the media following transduction.

The results of these experiments are shown in FIG. 15B and demonstrate that while lipid and lipid+siRNA treatment induce strong IL6 and IL8 response (600-2,500 picograms per ml), responses to all four G4 siRNAs were equivalent to media controls (<50 picograms per ml). Taken together with previous experiments, these studies demonstrate that passive delivery of G4 siRNA results in efficient gene knockdown with little or no induction of the innate immune response.

Off-Target Profile

To compare the off-target signatures associated with passive delivery of G4 siRNA and lipid-mediated delivery of siRNA, a PPIB-targeting duplex was introduced into HeLa cells by 1) passive delivery of G4 siRNA (using a G4 (-mm) complex), or 2) Lipofectamine 2000-mediated delivery (using the same duplex oligonucleotide as in the G4 siRNA, but without the Chol-05). Subsequently, cells were harvested and processed for global gene profiling as described above. Reference samples for each experiment included 1) for G4-siRNA: cells similarly treated with reduced serum media (no siRNA), 2) for lipid treated samples: lipid treated samples (no siRNA).

Figure 15C:
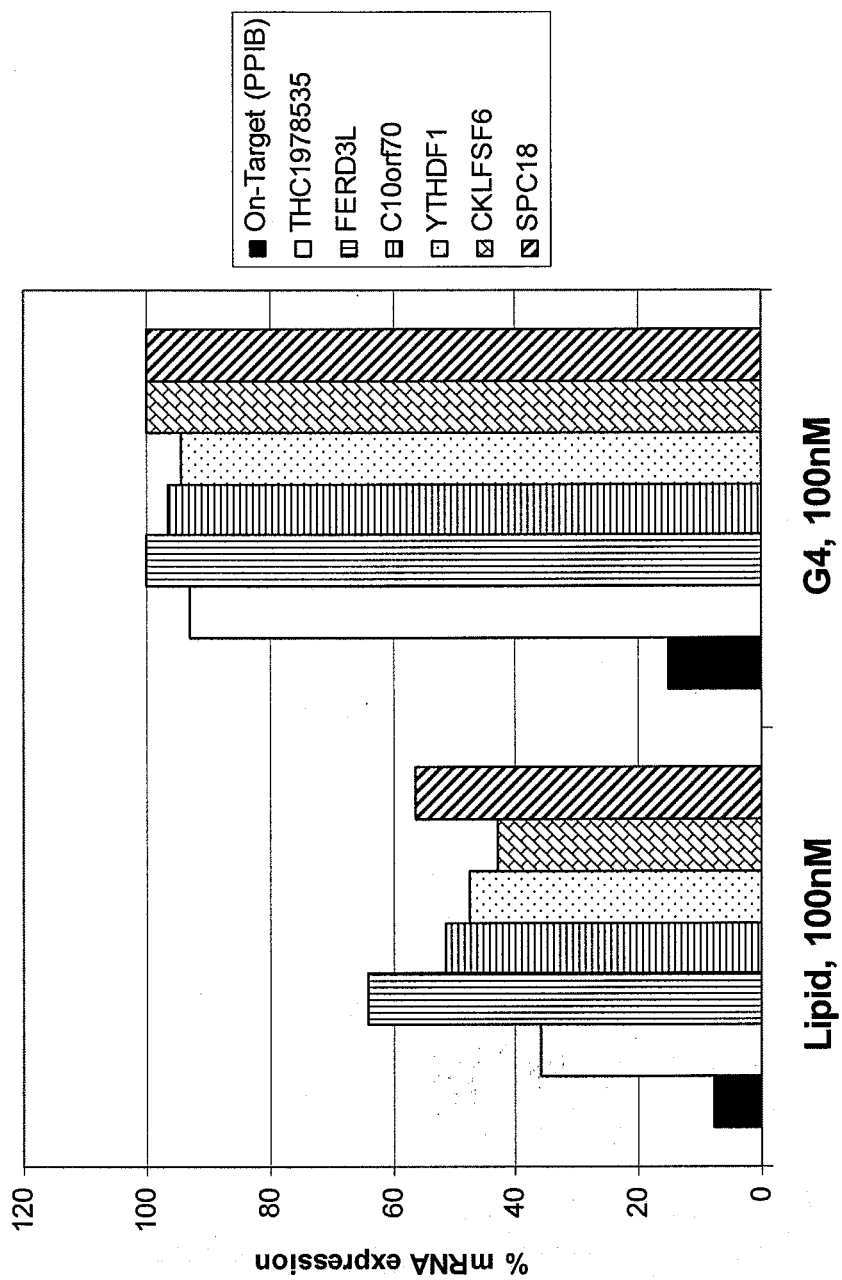
FIG. 15C provides a graph showing the level of target and off-target knockdown under lipid-mediated delivery of siRNA and passive delivery of G4 siRNA. The level of expression of the target gene (PPIB) and six off-target genes were monitored following lipid-mediated delivery of siRNA and passive delivery of G4 siRNA targetting PPIB. Y axis represents the percent of expression of each gene as compared to normal. Passive delivery of G4 siRNA delivery induces little or no off-target effects.

The results of off-target analysis are presented in FIG. 15C. While both methods of delivery provided greater than 80% gene knockdown of the target PPIB, a difference was found in the off-target signature. For lipid-mediated delivery, six different genes including THC1978535, FERD3L, C10orf70, YTHDF1, CKLFSF8, and SPC18, were identified as being down-regulated by approximately two-fold or more. In contrast, G4 siRNA had only minimal effects on the expression of any of the six off-targeted genes, indicating that G4 siRNA can be used to limit off-target signatures during RNAi-mediated gene knockdown.

Example 60

Stability of G4 siRNA in Serum-Free Media

To test the stability of G4 siRNA in reduced serum media, stock solutions of a PPIB-targeting G4 siRNA (G4 (-mm)) having sense strand: 5'-ACAGCAAAUUCCAUCGUGU (SEQ ID NO:12) or Non-Targeting Control (sense strand: 5'-UAAGGCUAUGAAGAGAUAC) (SEQ ID NO:13) siRNA in reduced serum media (HyClone) were prepared and stored at +4° C. (G4 siRNA concentrations of 1.0, 0.5, and 0.1 uM). On Days -1, 6, 13, 20, and 27 following the preparation of the +4° C. G4 stock solutions, HeLa cells were plated in DMEM+10% FCS. The next day, the overlying media was removed and replaced with the +4° C. stock solutions. G4 siRNA stored at -20° C. in Universal Buffer were used as controls. Cells were then cultured for 3 days and assessed for gene knockdown.

Figure 16:
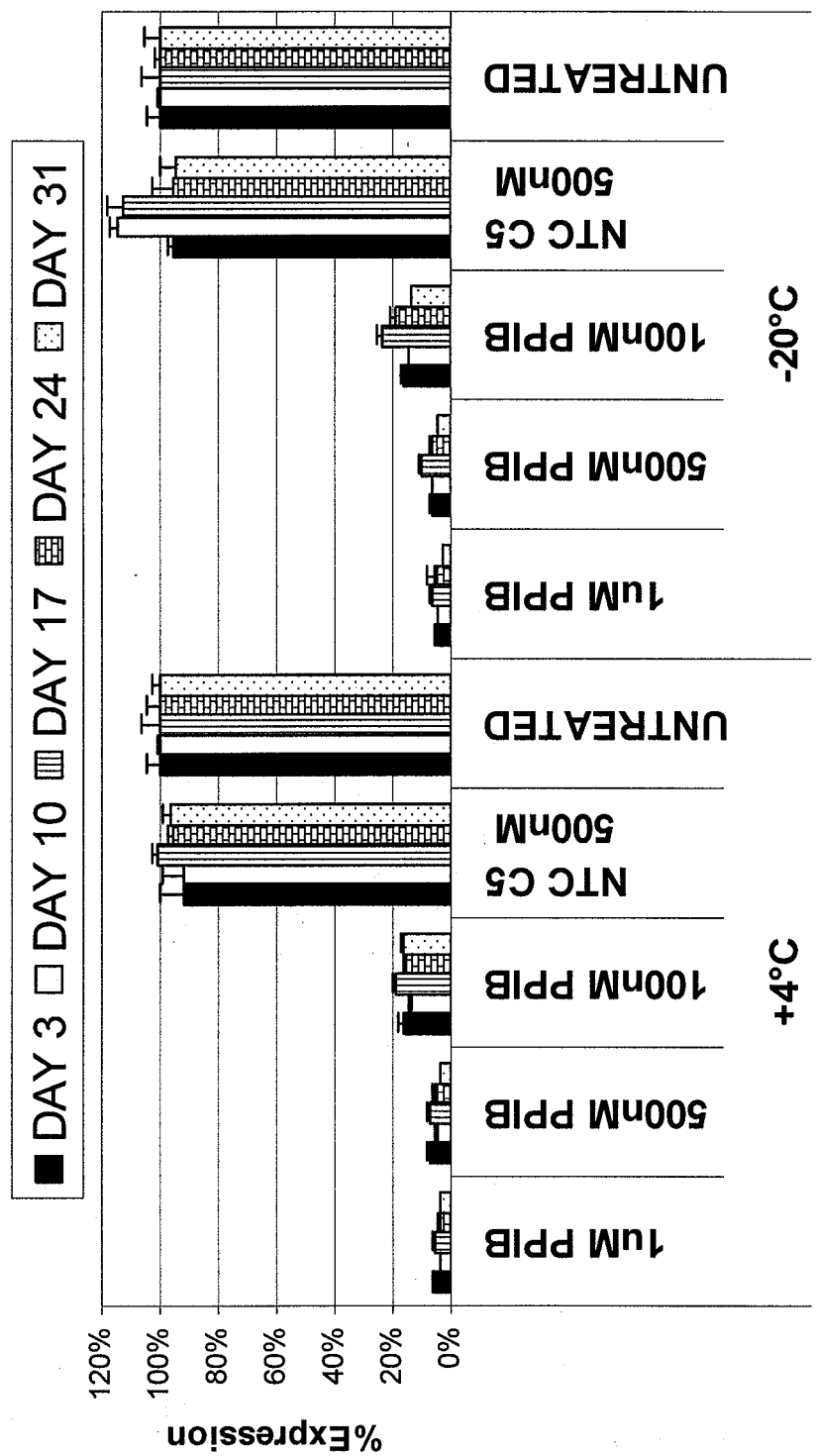
FIG. 16 provides a graph that shows the stability of G4-siRNA in reduced serum media. Stock solutions of PPIB-targeting G4 siRNA in reduced serum media were prepared and stored at +4° C. The activity of the molecules was tested at different times over the course of 31 days by measuring PPIB gene knockdown (branched DNA assay). For comparison, G4 PPIB siRNA stored at −20° C. in Universal Buffer was thawed and added to reduced serum media and run side-by-side with 4° C. samples. Y axis represents the fraction of PPIB expression (i.e. 0.2=20% expression). Results demonstrate that G4 siRNA can be stored in reduced serum media for extended periods of time without loss of activity. "NTC" refers to a non-targeting control.

Results of these studies are provided in FIG. 16 and show that storage of G4 siRNA in reduced serum media for 30 days had no effect on the ability of the molecule to knowdown gene expression. At 1 uM concentrations, PPIB gene knockdown was maintained at >90% over the course of the experiment. At 0.1 uM concentrations, the level of gene knockdown was slightly less (~80% KD), but this level is preserved across the length of the experiment. Non-targeting controls at 0.5 uM had no effect on overall gene expression. Together these experiments demonstrate that G4 siRNA can be stored in reduced serum media at +4° C. for extended periods of time without significant loss of gene silencing activity.

Example 61

Figure 17A:
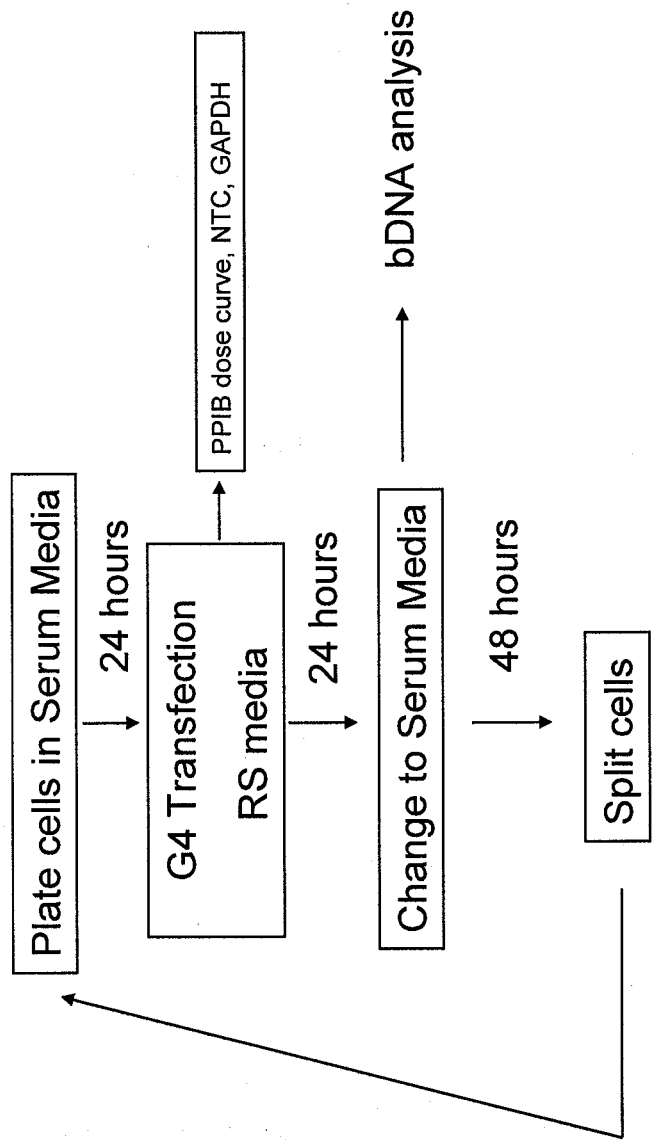
FIG. 17A illustrates schematically the protocol used to provide continuous gene knockdown using G4 siRNA.

Continuous Dosing of Cells with G4 siRNA Leads to Long Term Knockdown of Gene Expression Continuous dosing experiments were performed to assess whether G4 siRNAs could be used to provide long-term knockdown of a target gene. To test this, the following protocol was applied (see FIG. 17A):
 Day 1: HeLa cells are plated in DMEM media+10% FCS
 Day 2: Media is exchanged for reduced serum media containing PPIB-targeting, GAPDH-targeting, or Non-Targeting Control G4 siRNAs (specifically, G4 (-mm) siRNAs), concentrations ranging from 0.1-1 uM
 Day 3: Media is changed back to DMEM+ serum
 Day 5: Cells are split and replated
 Day 6: Cells were again treated with the G4 siRNA in serum free media This cyclic protocol of repeatedly exposing cells to G4 siRNA was repeated over the course of 30 days. On days 2, 6, 14, 18, 22, 26, and 30, treated cell samples were taken and assessed for target gene knockdown using a branched DNA assay.

Figure 17B:
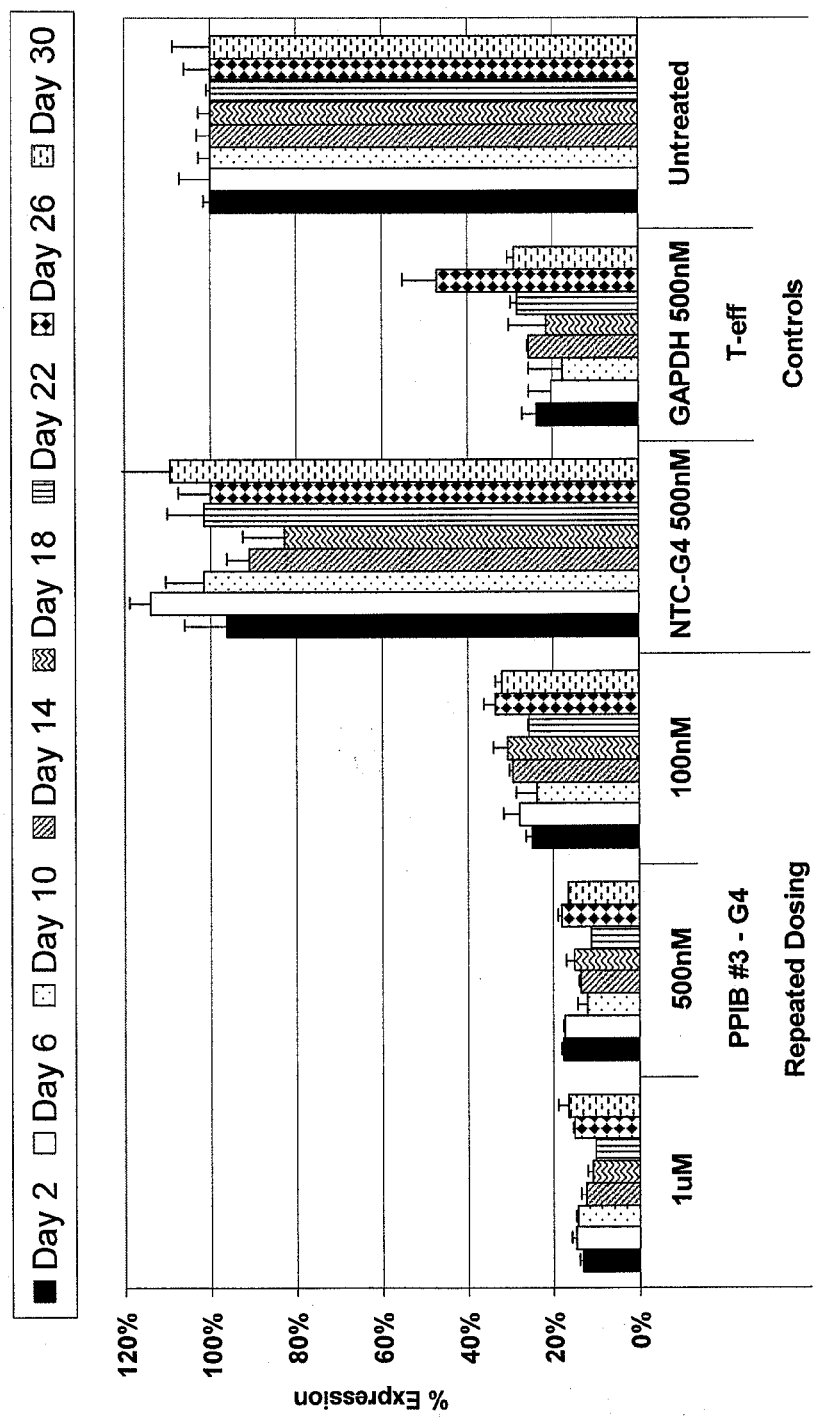
FIG. 17B represents PPIB and GAPDH gene knockdown results during a continuous dosing experiment. Results clearly demonstrate that potent gene knockdown can be achieved for a minimum of 30 days using the described protocol.

The results of these experiments are presented in FIG. 17B and demonstrate that using the protocol described above, continuous gene knockdown can be achieved with G4 siRNA. At 0.5 and 1 uM concentrations, greater than 80% gene knockdown is preserved for the entire period of the experiment. At 0.1 uM concentrations, the level of gene knockdown is slightly less (~75% KD), but this level is again preserved across the length of the experiment. Results obtained with non-targeting controls mirrored those of untreated cells while GAPDH-targeting G4 siRNA controls (0.5 uM) also provided strong knockdown (~80%) with the exception of one anomalous data point (Day 26) which showed ~50% silencing. Overall, these experiments demonstrate that like plasmid or viral mediated RNAi, continuous dosing with G4 siRNAs can provide long term gene knockdown.

Example 62

Identification of Additional Conjugates that are Compatible with the C5 Linker

Figure 18A:
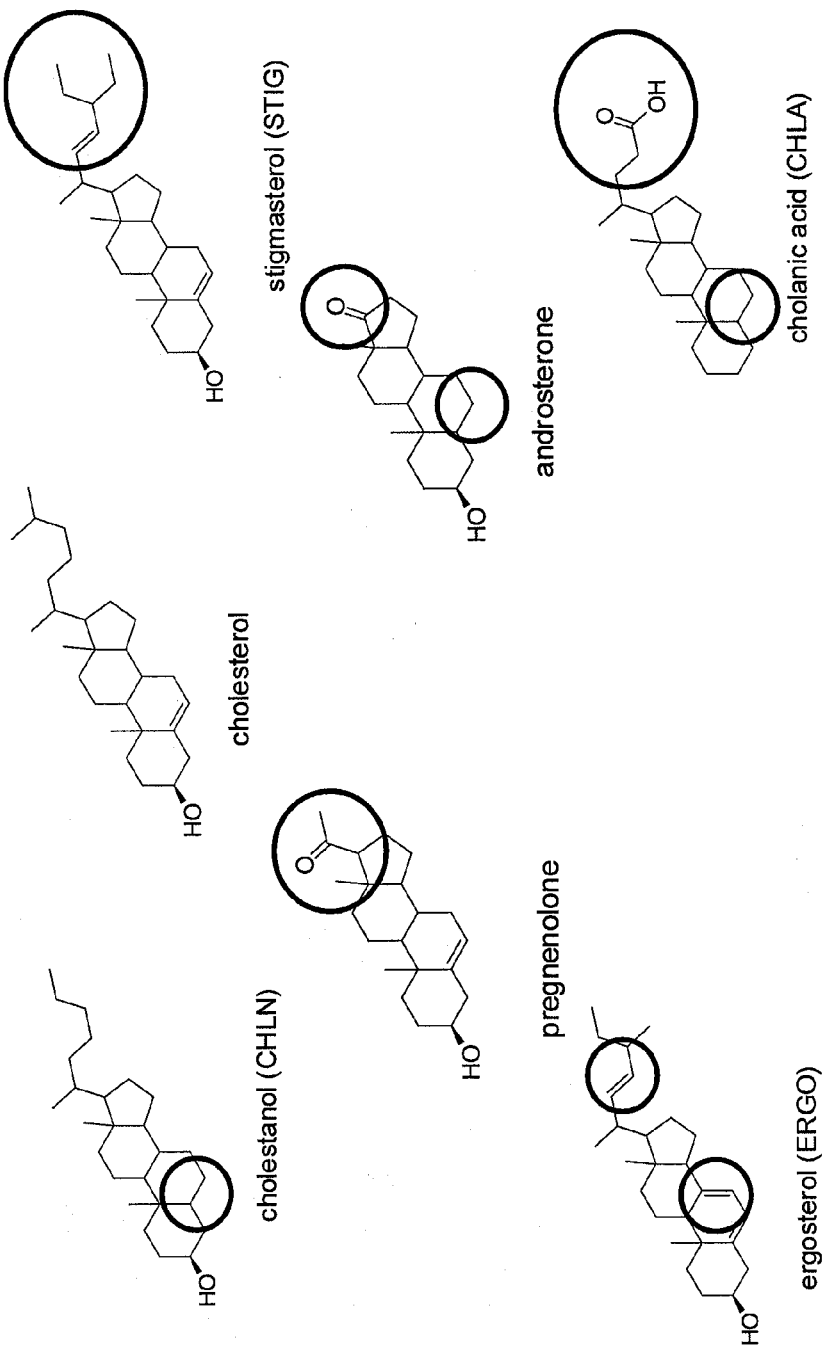
FIG. 18A provides the structures of cholestanol, cholesterol, stigmasterol, pregnenolone, adosterone, ergosterol, and cholanic acid. Circled regions indicate key differences in chemical structure with cholesterol.

To test the compatibility of siRNA containing a 3' sense strand C5 linker with alternative conjugate moieties, functional duplexes targeting PPIB or GAPDH were synthesized with cholestanol, stigmasterol, pregnenolone, andosterone, ergosterol, or cholanic acid as the conjugate moiety (see FIG. 18A). Synthesis for each molecule is described in previous sections. The resulting complexes have the same modification pattern as a G4 complex (specifically, a G4 (–mm) complex) except that the cholesterol of G4 is replaced with cholestanol, stigmasterol, pregnenolone, andosterone, ergosterol, or cholanic acid.

Following synthesis, the ability of each construct to knockdown the intended gene target by passive delivery was tested by (1) culturing HeLa cells (2.5K cells per well, 96 well plate) overnight in complete media (DMEM+10% FCS), and (2) replacing media with reduced serum media containing the test molecule at concentrations ranging from 0.1-2.0 uM. After 24 hours, media was replaced with DMEM+10% FCS. At 72 hours post-treatment, gene knockdown was assessed using untreated cells or cells treated with a non-targeting duplex for data mormalization.

Figure 18B:
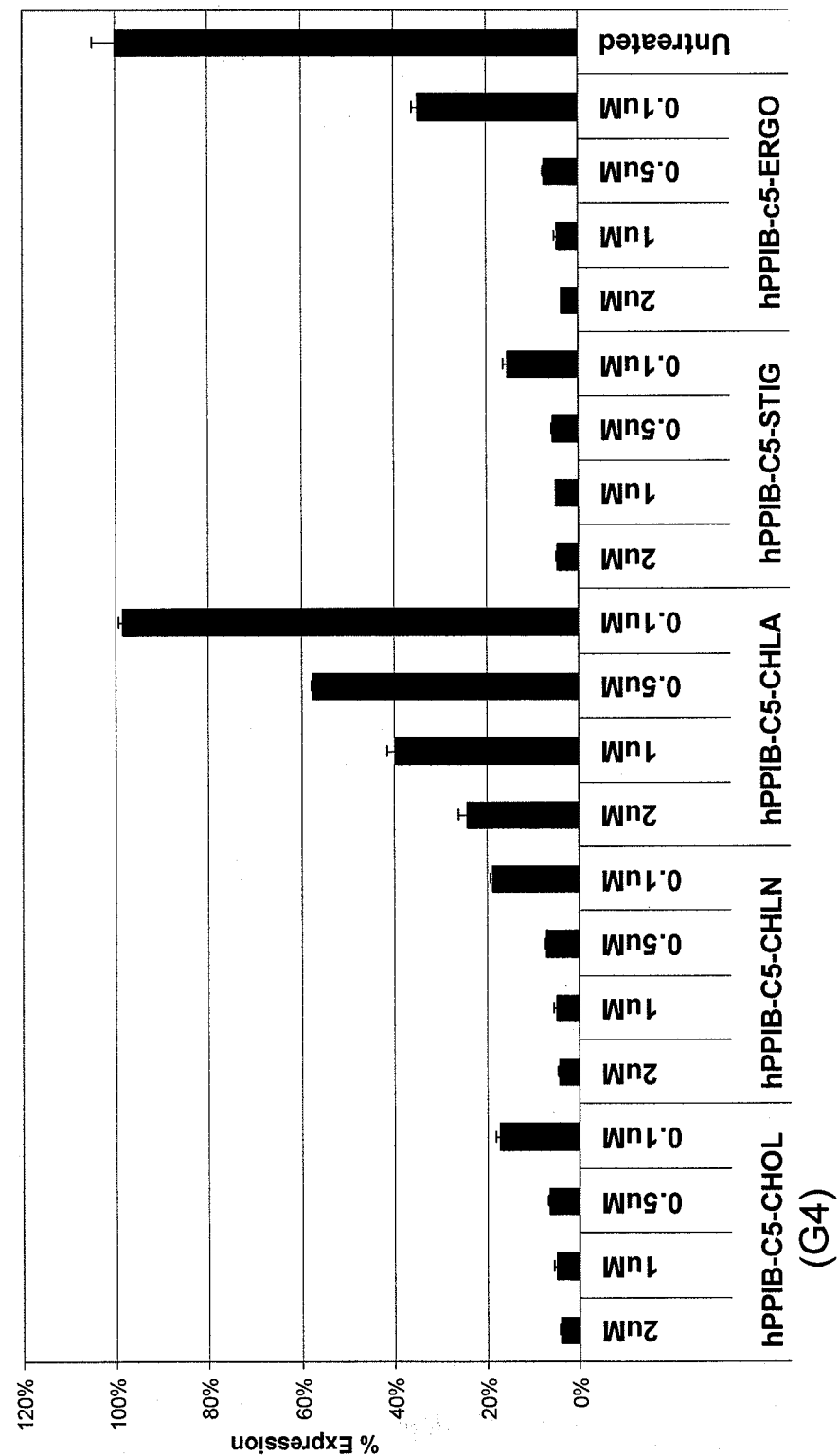
FIG. 18B provides a graph that compares the gene knockdown ability of G4 siRNA with cholestanol, stigmasterol, ergosterol, or cholanic acid conjugated molecules in HeLa cells.
Figure 18C:
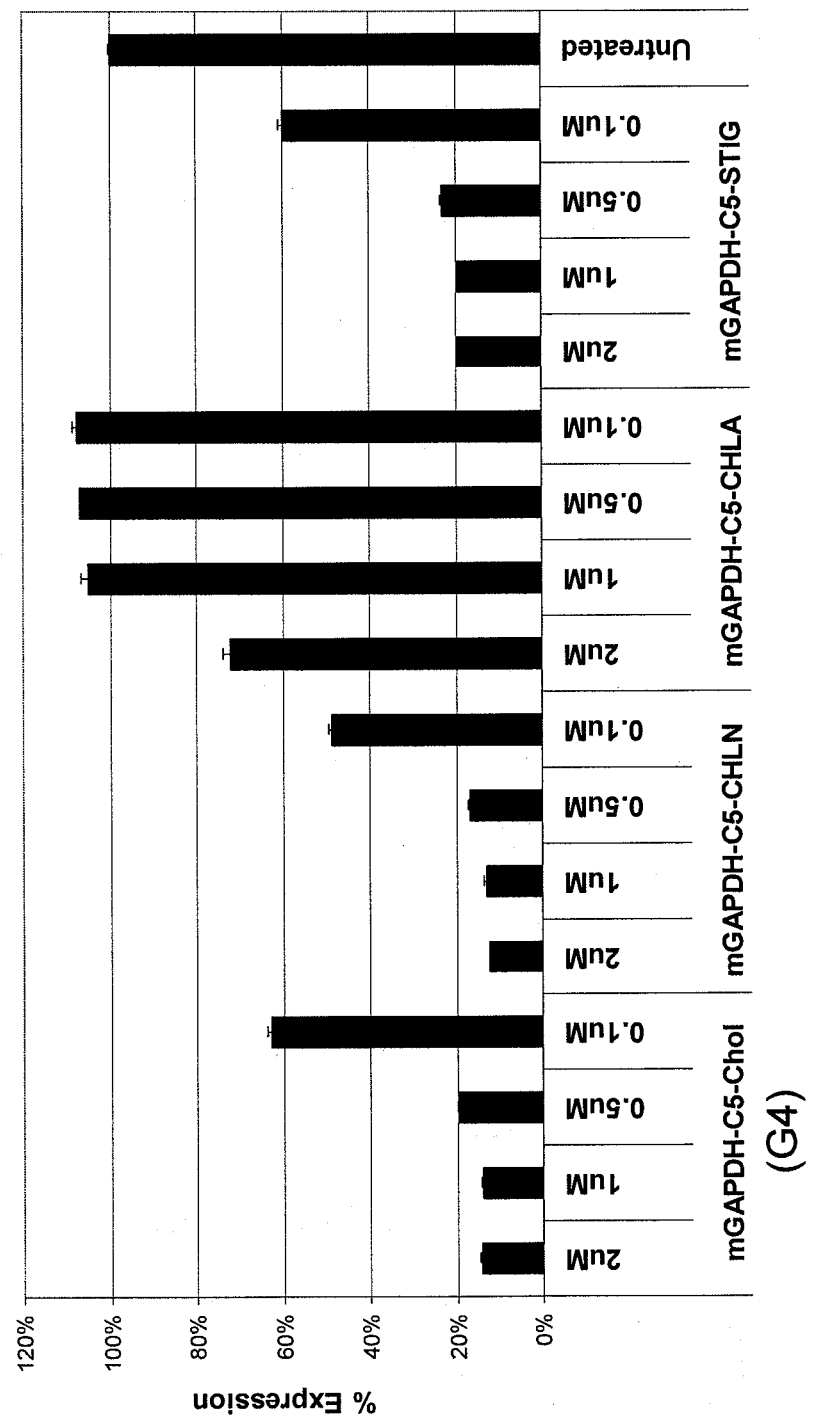
FIG. 18C provides a graph that compares the gene knockdown ability of G4 siRNA with cholesterol, cholestanol, stigmasterol, and cholanic acid conjugated molecules in mouse 3T3 NIH cells.
Figure 18D:
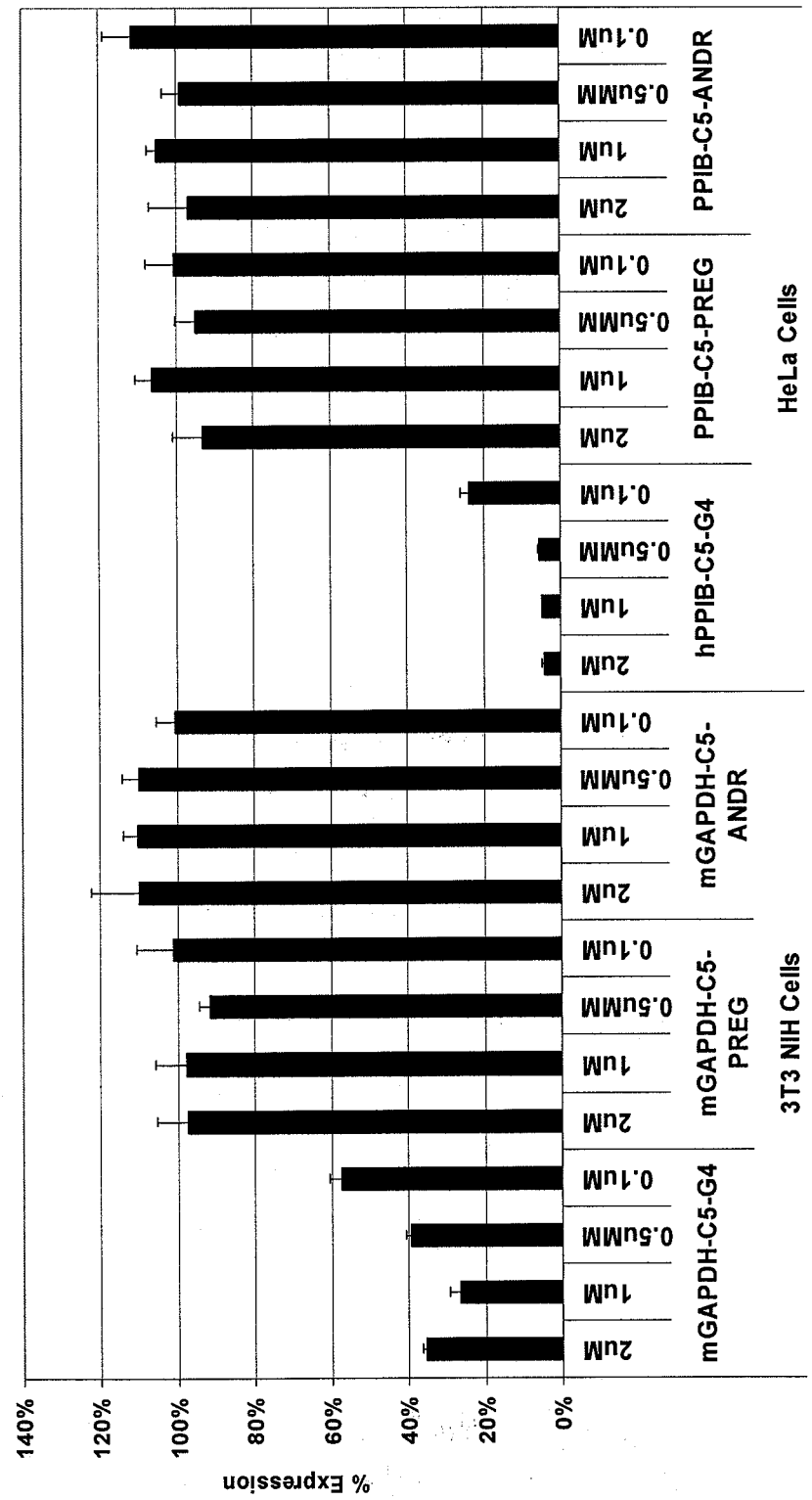
FIG. 18D provides a graph that compares the gene knockdown ability of hPPIB and mGAPDH G4 siRNA with cholesterol (e.g., mGAPDH-C5-G4), pregnenolone (e.g., mGAPDH-C5-PREG) and adosterone (e.g., mGAPDH-C5-ANDR) modified siRNA in mouse (3T3 NIH cells and human HeLa cells).

The results for these studies are presented in FIGS. 18B-D and are summarized as follows:

Cholestanol and Stigmasterol:
PPIB siRNA conjugated to cholestanol (CHLN) and stigmasterol (STIG) performed similarly to cholesterol-conjugated molecules (CHOL), providing greater than 80% knockdown at concentrations as low as 0.1 uM. GAPDH-targeting molecules containing the same conjugation pattern were found to be effective in non-human (mouse 3T3 NIH) cells, suggesting that passive delivery of siRNAs having cholestanol and stigmasterol conjugate-linker configuration were broadly applicable.

Ergosterol:
PPIB siRNA conjugated to ergosterol (ERGO) via the C5 linker performed well at concentrations between 0.5 uM and 2.0 uM (>80% gene knockdown). At the 0.1 uM concentration, passive delivery of the siRNA was still observed, yet the conjugate was not as functional as cholesterol, cholestanol, or stigmasterol conjugates at equivalent concentrations.

Cholanic Acid:
PPIB siRNA conjugated to cholanic acid (CHLA) provided roughly 80% and 60% gene knockdown at the 2 and 1 uM concentrations, respectively. At lower concentrations, passive delivery dropped off precipitously. Similar results were obtained in mouse 3T3 NIH cell lines.

Pregnenolone and Andosterone:
Linking pregnenolone or andosterone to the 3' terminus of the sense strand using a C5 linker failed to silence target gene expression at any of the concentrations tested. These results were observed regardless of the cell line employed (e.g. HeLa or 3T3 NIH).

Together, these studies have identified a number of moieties that can be effectively conjugated to the 3' terminus of an siRNA sense strand (using the C5 linker) to provide passive delivery and potent gene knockdown. Furthermore, the results demonstrate that not all sterol molecules are compatible with this form of passive delivery.

Example 63

The Impact of Serum and Cholesterol Binding Proteins on Passive Delivery of G4 siRNA Two studies were performed to better understand the impact of various tissue culture conditions on passive delivery of cholesterol conjugated siRNA. In the first experiment, the level of gene knockdown was measured when various concentrations of serum were present during passive delivery. To achieve this, 2.5K 3T3 NIH, HeLa, or SHSY-5Y cells were first cultured overnight in DMEM supplemented with 10% FCS. On the following day, the overlying media was removed and replaced with reduced serum media containing (1) G4 siRNA targeting GAPDH or PPIB (sense strand PPIB 69 5' UCACGACAGUCAAGACAGC 3'(SEQ ID NO:14) and PPIB 39 sense strand 5' CAGCAAAUUCCAUCGUGUA3' (SEQ ID NO: 15) at concentrations ranging from 0.1-1 uM, plus (2) fetal calf serum (FCS) at concentrations ranging between 0-10% (v/v). Cells were maintained under these conditions for an additional 48 hours and gene knockdown was then assessed using a branched DNA assay. The G4 siRNAs were all G4 (–mm).

Figure 19A:
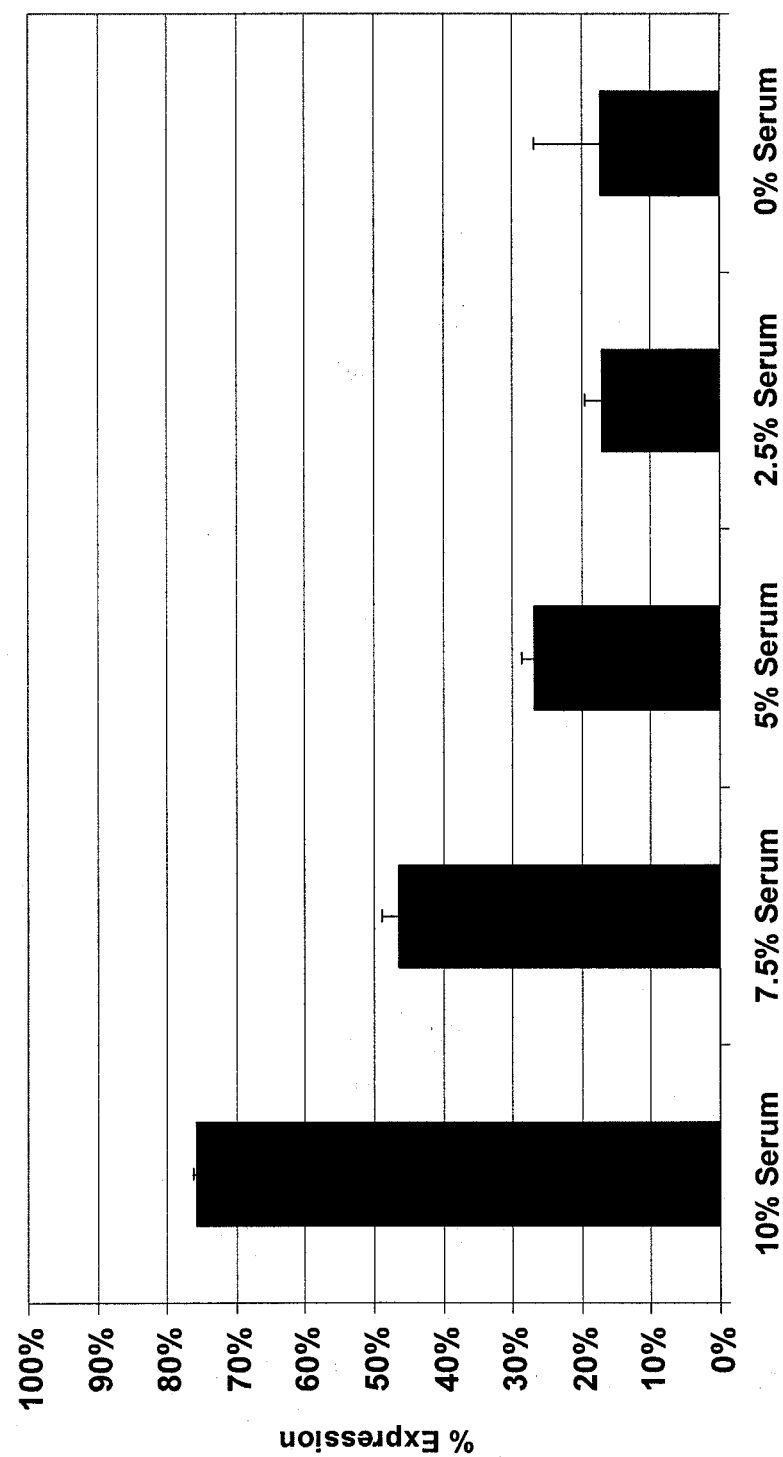
FIG. 19A provides a graph showing the effects of the presence of fetal calf serum (FCS) on passive delivery of G4 siRNA. NIH 3T3 cells were exposed to 1 uM G4 GAPDH-targeting siRNA in the presence of increasing levels of serum (0-10% FCS, v/v). Quantitation of gene silencing took place at t=72 hr. Y axis represents normalized levels of GAPDH expression. Results show that increasing levels of serum have detrimental effects on passive delivery.
Figure 19B:
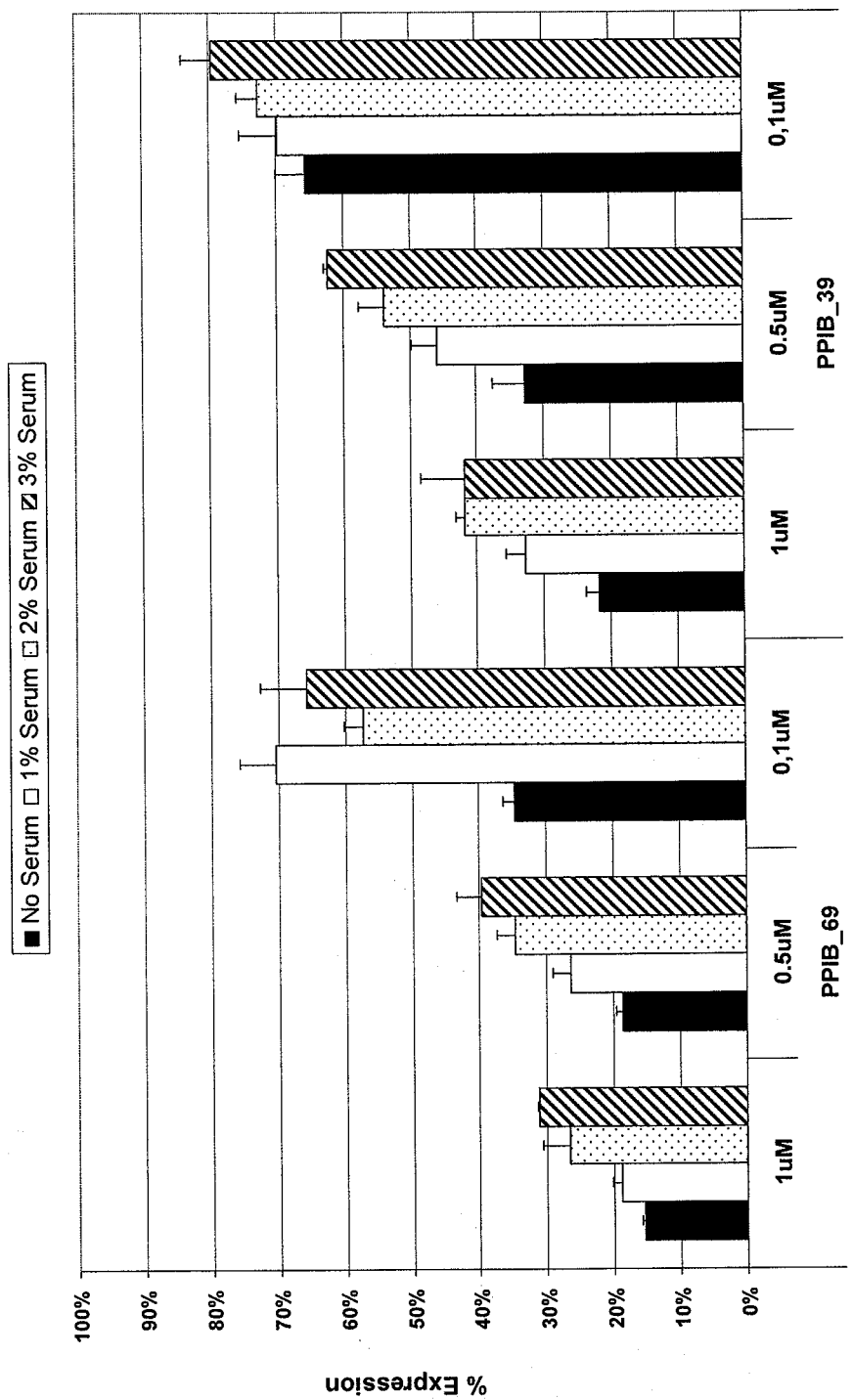
FIG. 19B provides a graph that shows the effects of serum concentrations on passive delivery of G4 siRNA delivery in HeLa cells. Serum concentrations range from 0-3% and concentrations of G4 siRNA targeting the PPIB gene vary between 0.1 and 1.0 uM. Results show that serum levels play a critical role in the ability of G4 siRNA to silence PPIB expression.
Figure 19C:
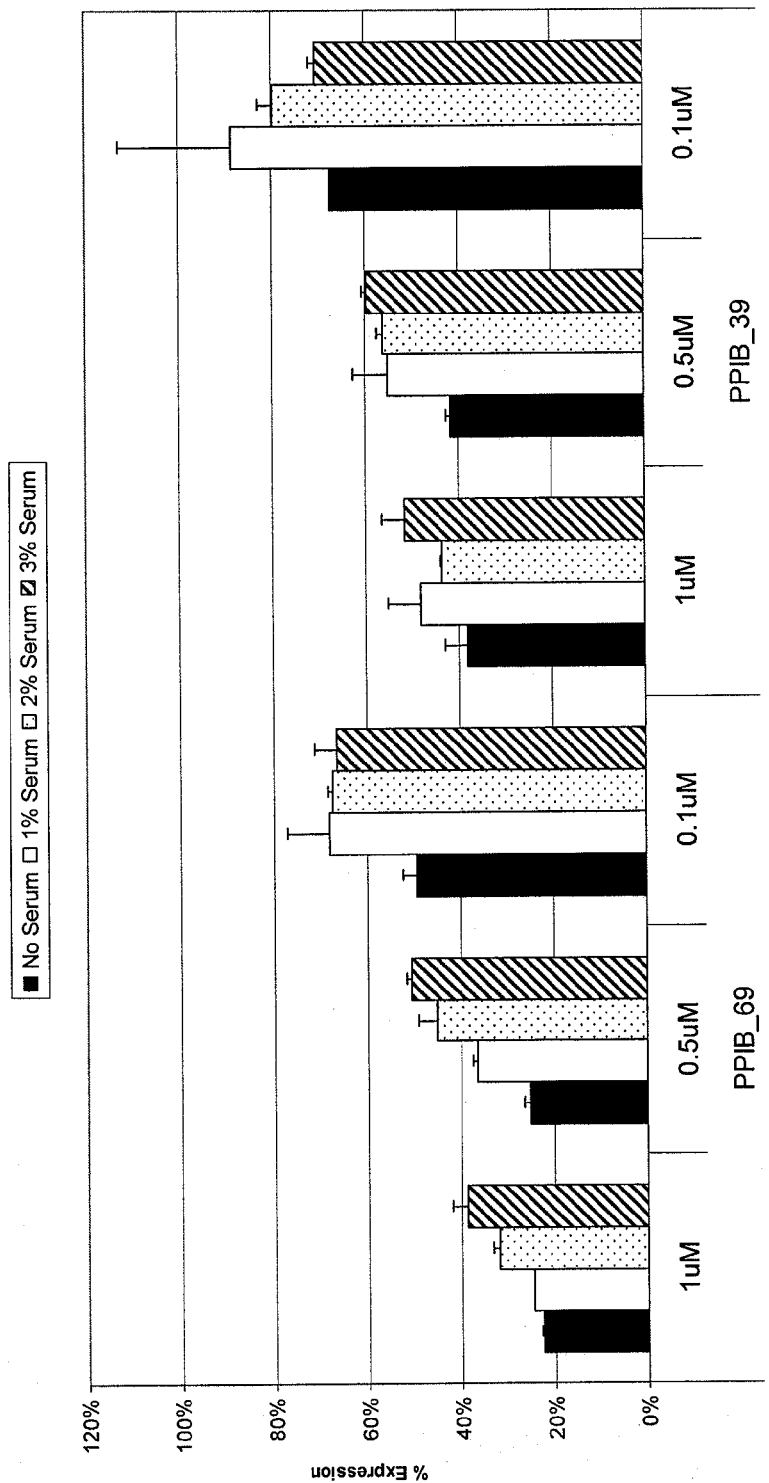
FIG. 19C provides a graph showing the effects of serum concentrations on passive delivery of G4 siRNA in SHSY-5Y cells. Serum concentrations range from 0-3% and concentrations of G4 siRNA (PPIB 69 and PPIB 39) vary between 0.1 and 1.0 uM. Results show that serum levels play a critical role in the ability of G4 siRNA to silence PPIB expression.

Results of these studies demonstrate that passive delivery of G4 siRNA is strongly dependent upon the concentration of the serum in the media during passive delivery (FIG. 19A-C). Concentrations as low as 2.5% FCS affected the overall level of gene knockdown slightly while higher concentrations compromised delivery and gene knockdown significantly.

Figure 19D:
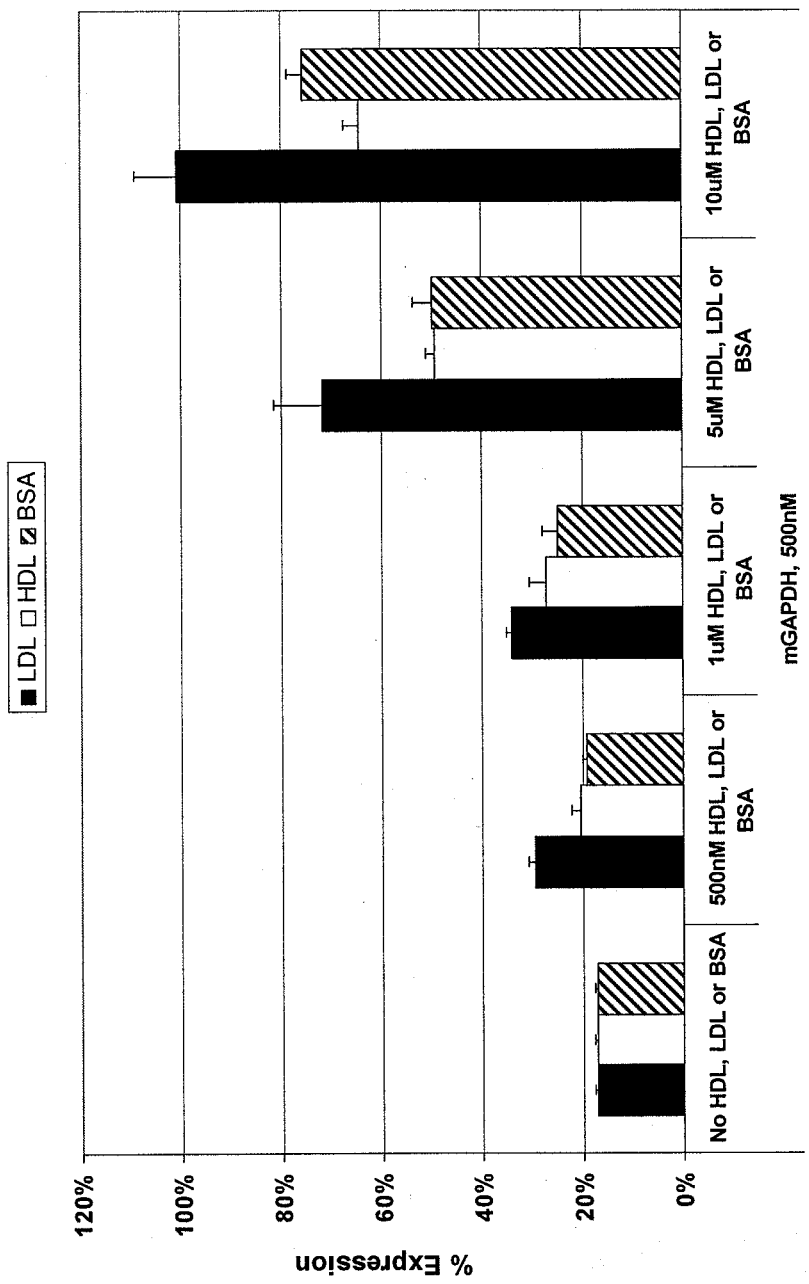
FIG. 19D provides a graph that shows the effects of the presence of three different cholesterol binding protein/protein complexes (albumin, LDLs, and HDLs). 3T3 NIH cells were exposed to 0.5 uM G4 GAPDH-target siRNA in the presence of increasing levels of each protein (0-10 uM). Y axis represents fraction of GAPDH expression. Results show increasing concentrations of each cholesterol binding protein negatively affects passive delivery of G4 siRNA.

Fetal calf serum contains multiple proteins and protein complexes that associate with cholesterol. To test whether three cholesterol binding proteins (LDLs, HDLs, and albumin) could be responsible for the inhibition of G4-siRNA mediated gene knockdown by FCS, the studies described above were repeated with the modification that FCS was replaced with either LDL, HDL, or BSA. The results of these experiments show that supplementing the media with any of the three cholesterol binding proteins can greatly inhibit passive delivery of G4 siRNAs (FIG. 19D).

Example 64

In Vivo Efficacy of G4

To test the effectiveness of G4 siRNA to provide gene silencing in vivo, siRNAs having the following designs were synthesized:
1. Non-targeting control G4 (–mm), (5' UAAGGC-UAUGAAGAGAUAC, sense strand) (SEQ ID NO: 16)
2. PPAR-gamma-targeting G4 (–mm), (5'GACAUGAA-UUCCUUAAUGA, sense strand) (SEQ ID NO: 17)
3. ApoB-targeting G4 (–mm) (5' GUCAUCA-CACUGAAUACCA, sense strand) (SEQ ID NO: 18)
4. ApoB targeting siRNA containing a cholesterol conjugated via a HP6 linker (identical to 3, except with a HP6 linker rather than a C5 linker).

Figure 20A:
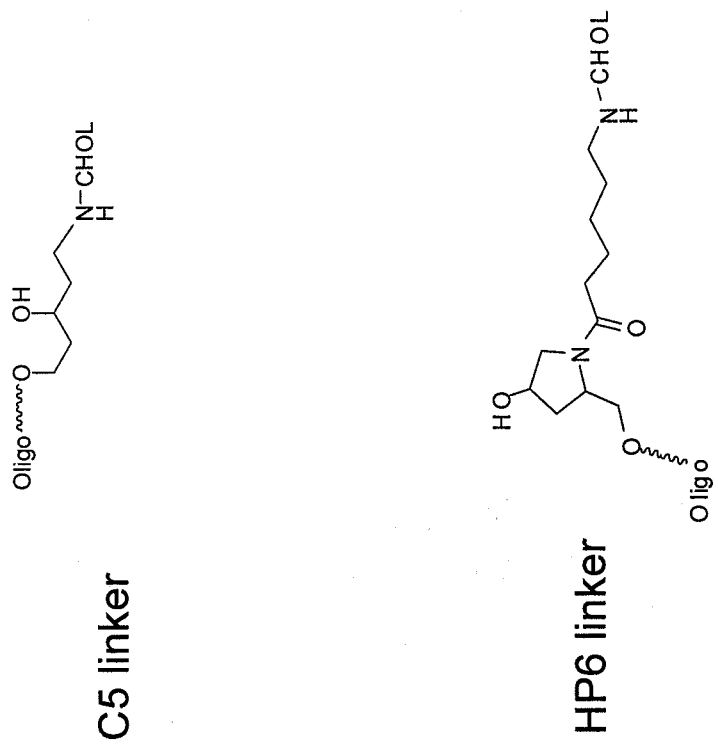
FIG. 20A provides the chemical structure of C5 and HP6 linkers.

FIG. 20A depicts the structures of the C5 and HP6 linkers. Each of these molecules was introduced into male ICR mice weighing approximately 25-30 grams (5 animals per group) and gene knockdown was compared with animals receiving a saline control. Doses consisted of 50 mg/kg low pressure tail vein injections, once daily for three consecutive days. Animals were harvested 72 hours after the last injection and tissues examined included the liver, spleen, lung, heart, and kidney. Tissues were extracted, dissected into four sections, flash frozen in liquid nitrogen, and stored at –80° C. Total RNA was later purified using the TRIzol® Plus RNA Purification System (Invitrogen, Catalog Number—12183-555) and mRNA knockdown was analyzed by branched DNA (Panomics).

Figure 20B:
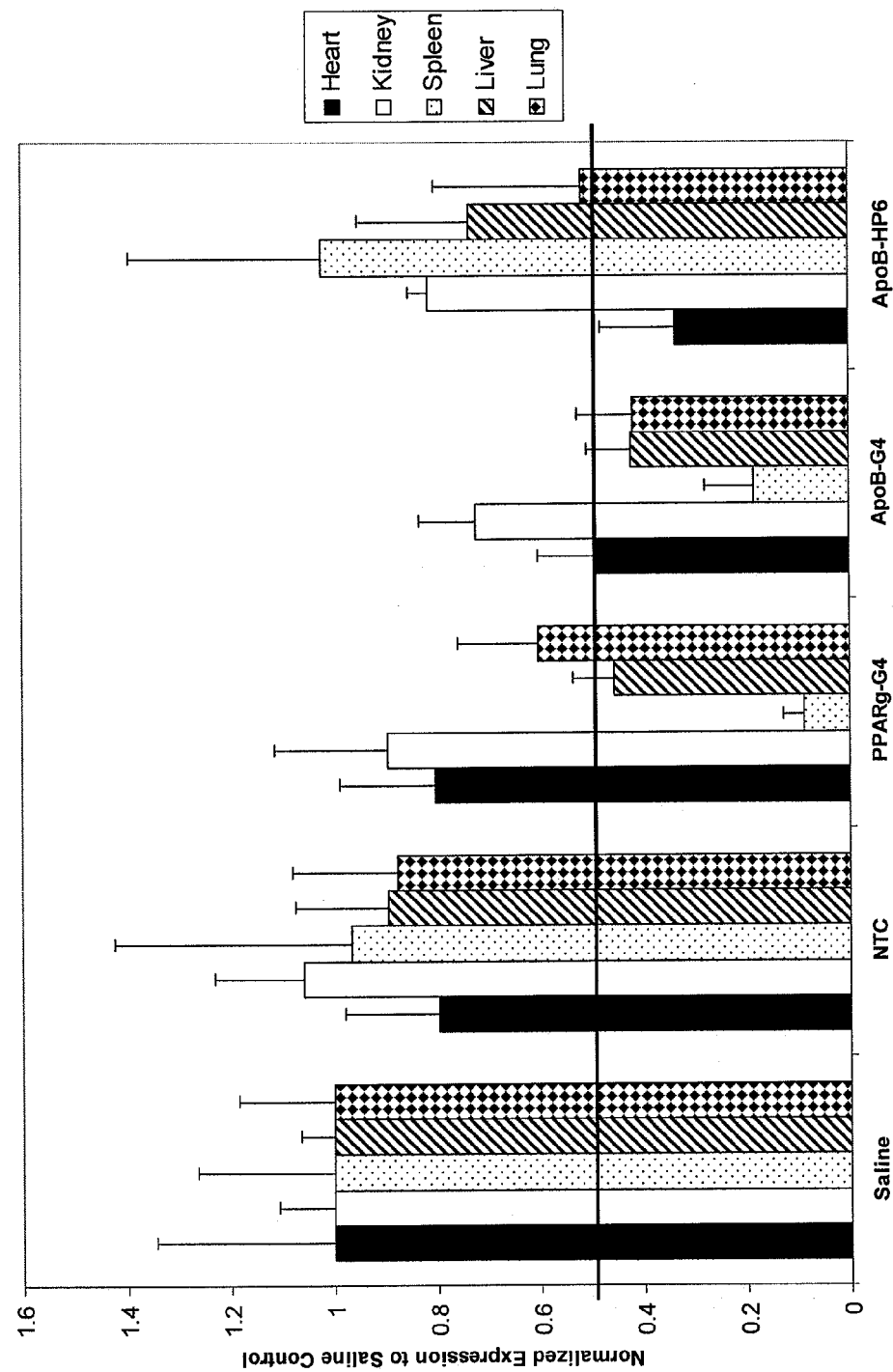
FIG. 20B shows the ability of G4 siRNA targeting PPAR-gamma and ApoB to target genes in the kidney, spleen, liver, heart, and lungs. G4 siRNA thus enables gene silencing in multiple tissues.

In at least one of the two genes studied (ApoB or PPAR-gamma) G4 siRNA delivered in vivo provided roughly 50% gene knockdown in the spleen, liver, heart and lung (FIG. 20B). Thus, this analysis demonstrates that using an unoptimized delivery regime, G4 siRNAs are capable of inducing potent gene knockdown in multiple tissues. FIG. 20B also provides a side-by-side comparison of the tissue-specific differences that result from changing the linker. While G4 and HP6 mediated knockdown of ApoB are similar in the kidney, heart, and lung, adoption of the C5 linker in G4 improves knockdown in the spleen and liver. Thus, G4 siRNA is particularly valuable when gene knockdown is desired in the spleen and liver tissues.

Example 65

Identifying Secondary Structures that Enhance Functionality of G4 siRNAs

G4 siRNAs were synthesized with mismatches at various positions to determine whether the incorporation of secondary structures could enhance overall functionality. To achieve this, a poorly functional GAPDH-targeting siRNA was synthesized with all possible sense-antisense strand mismatches at positions 6-10 of the sense strand. Subsequently, the ability of each of these molecules to induce GAPDH knockdown via passive delivery was assessed via branched DNA assay (passive delivery conditions: 2.5K HeLa cells plated, siRNA concentration=0.1 uM or 1 uM, reduced serum media, knockdown assessed at 72 hr).

Figure 21A:
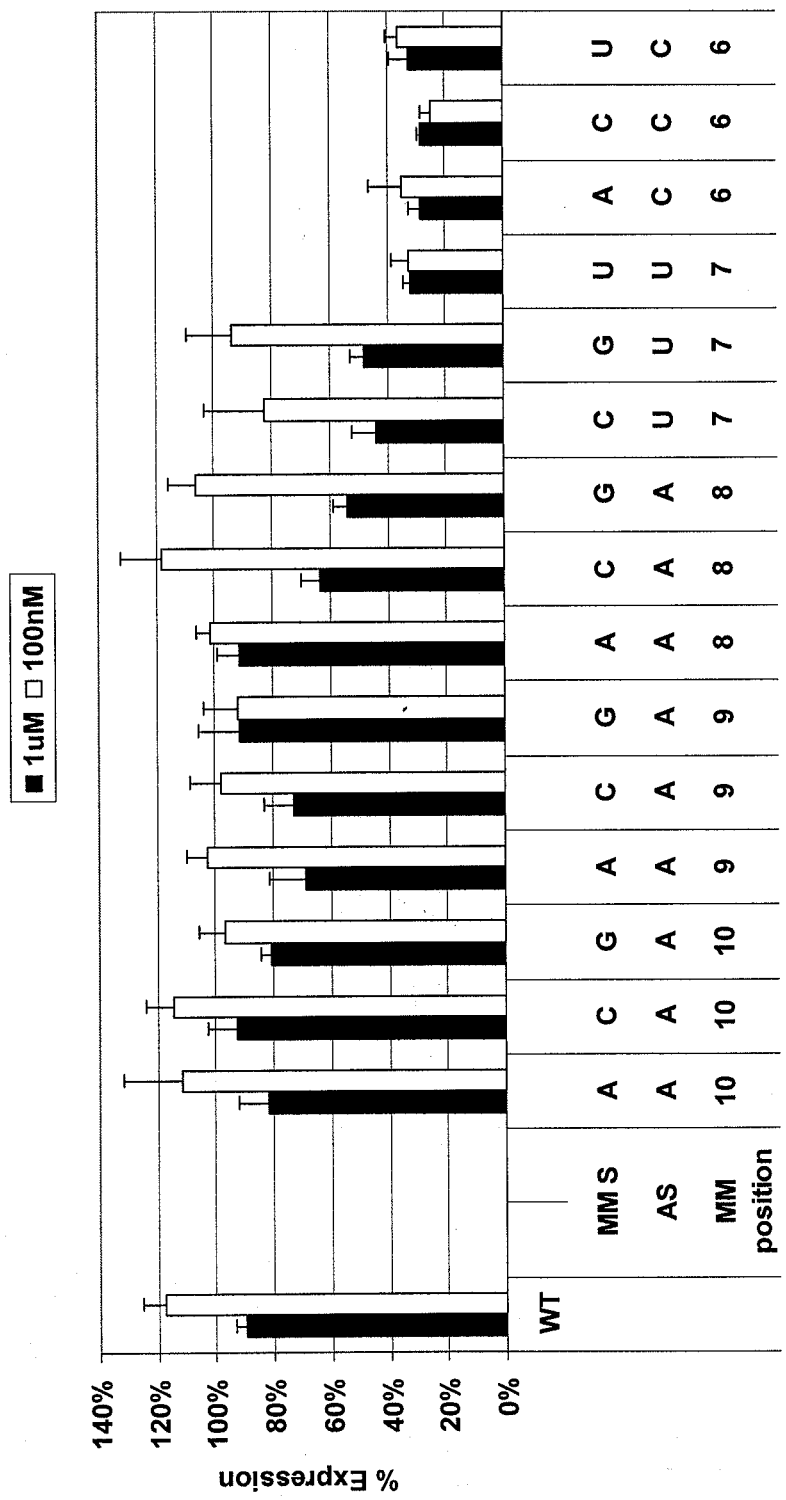
FIG. 21A provides a graph depicting the effects of single mismatches between the sense and antisense strand at sense positions 6-10 (numbered from the 5' end of the sense strand) of G4 siRNA. Sequence changes occur in the sense strand, thus preserving perfect complementarity between the antisense strand and the target mRNA. Results show that incorporation of a mismatch at sense strand positions 6 or 7 greatly enhances gene knockdown. Studies performed at both 0.1 and 1.0 uM.

The results of these experiments are shown in FIG. 21A and demonstrate that incorporation of a mismatch at positions 6 and/or 7 of the sense strand greatly enhance the functionality of the G4 siRNA. This enhancement appears to be unrelated to the type of mismatch (e.g., C-A=C—C) suggesting that this trait is sequence independent. For a 19 nucleotide G4 sense strand and a 19 nucleotide G4 antisense strand, positions 6 and 7 on the sense strand (numbered from the 5' end) are opposite positions 14 and 13 respectively on the antisense strand (numbered from the 5' end).

Figure 21B:
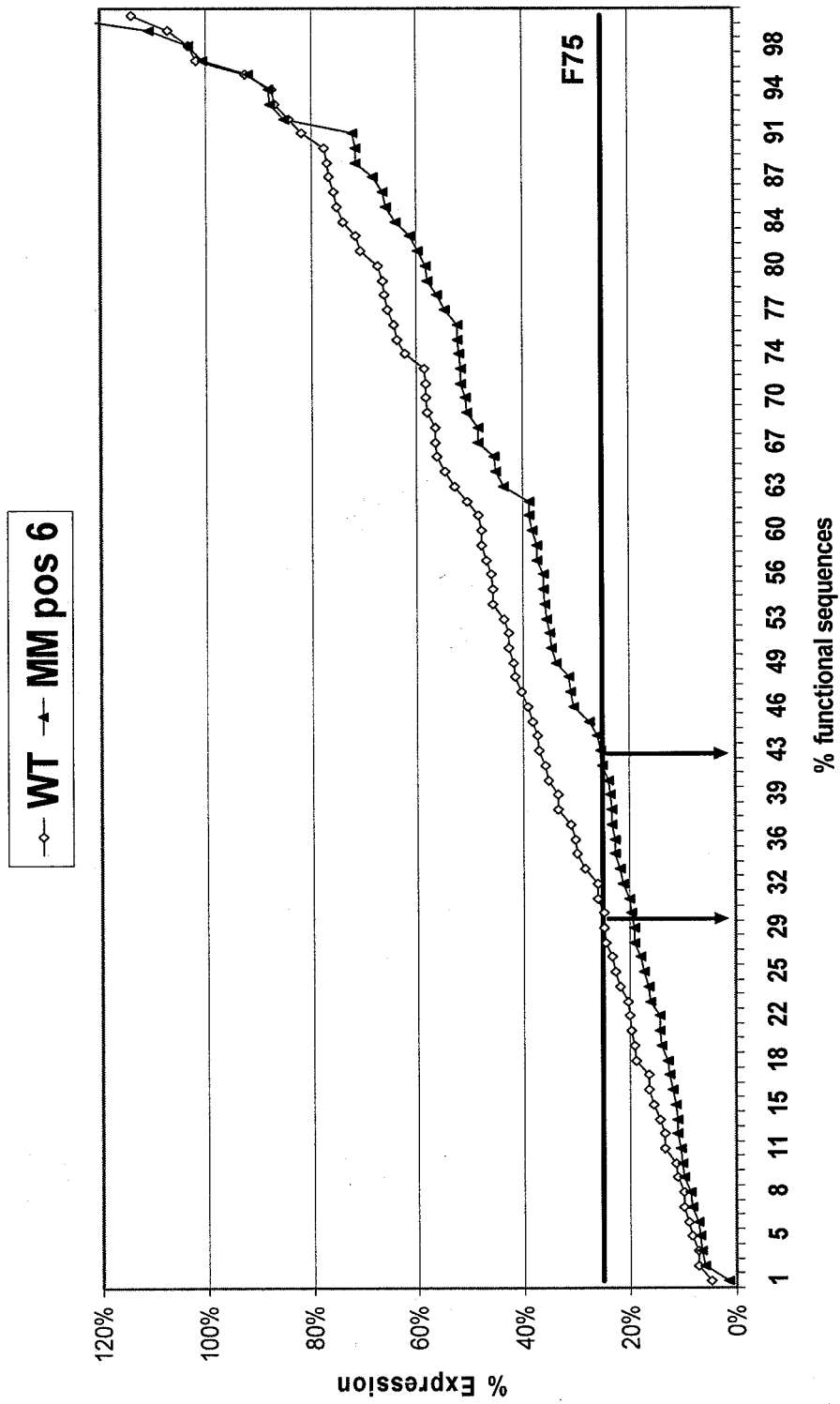
FIG. 21B provides a graph that represents a broad study of the effects of position 6 mismatch on G4 siRNA functionality. Eighty-seven siRNAs synthesized as G4 (−mm) or G4 (+mm) duplexes were transfected into cells at 1 uM concentrations. For these experiments, the mismatch incorporated at position 6 always consisted of replacing the native nucleotide in the sense strand with the nucleotide that was found in pairing position in the antisense strand (e.g. A-A, G-G, C-C, or U-U mismatches). Branched DNA assays were used to assess gene knockdown. The results demonstrate that incorporation of a mismatch at sense position 6 (which is opposite antisense strand position 14, numbered from the 5' end, for a 19 nucleotide sense strand) enhances functionality of a significant fraction of G4 siRNAs.

To further study the effects of position 6 mismatches, 87 different G4 siRNAs targeting hPPIB were synthesized with (i.e., G4 (+mm)) and without (i.e., G4 (-mm)) the sense strand position 6 (i.e. antisense strand position 14) mismatch. As shown in FIG. 21B, incorporation of the mismatch enhances overall gene silencing within the population, increasing the number of duplexes that silence gene expression by 75% from 30% to 43%.

Example 66

Effectiveness of G4 siRNAs to Silence Gene Expression

To test the effectiveness of G4 siRNAs containing the mismatch to knockdown a range of target mRNAs, G4 (+mm) siRNAs targeting human genes (LMNA, CDC2, TP53, AKT1, RB1, HR1, MET, PLK) as well as rat and mouse genes (PPIB and GAPDH) were synthesized (see Table IV below for list of sequences and accession numbers) and passively introduced into HeLa-S3 cells (1 uM) as individual siRNAs or as pools using the previously described protocol.

TABLE IV

Sense strand sequences for three separate siRNAs used in Example 66.

| Target Symbol | Gene Name | Accession No. | Sense Sequence 5'→3' | SEQ ID NO: |
|---|---|---|---|---|
| LMNA | Lamin A/C | NM_005572 | GCAACAAGUCCAAUGAGGA | 19 |
| | | | UCACCGAGUCUGAAGAGGU | 20 |
| | | | GUGAGGAGUUUAAGGAGCU | 21 |
| CDC2 | cell division cycle 2 | NM_001786 | CCAUGGAUCUGAAGAAAUA | 22 |
| | | | UCCUAGUACUGCAAUUCGG | 23 |
| | | | GAGUUGUGUAUAAGGGUAG | 24 |
| TP53 | tumor protein p53 | NM_000546 | UGCUCAGGGUCAAUUUCUU | 25 |
| | | | CUCUUGUAUAUGAUGAUCU | 26 |
| | | | CCCUCACUGUUGAAUUUUC | 27 |
| AKT1 | v-akt murine thymoma viral oncogene homolog 1 | NM_005163 | GUGCCAUGAUCUGUAUUUA | 28 |
| | | | GUAUUUUGAUGAGGAGUUC | 29 |
| | | | GGUUUAAAUUUGUUAUUGU | 30 |
| RB1 | retinoblastoma 1 | NM_000321 | GCUUUGAUAUUGAAGGAUC | 31 |
| | | | UCGUCAGGCUUGAGUUUGA | 32 |
| | | | CUUGUAACAUCUAAUGGAC | 33 |
| HRI | heme-regulated initiation factor 2-alpha kinase | NM_014413 | CCAAAAUUCUGGAAAUGUU | 34 |
| | | | GUAGUUAACUGGAAUGUAA | 35 |
| | | | GUAUGAUUUUGCUGAAUUU | 36 |
| MET | met proto-oncogene | NM_000245 | CCUGCAAUCUACAAGGUUU | 37 |
| | | | CUGUUGUCAUCAGAAGAUA | 38 |
| | | | GCAUGAAGCAGGAAGGAAC | 39 |
| PLK | polo-like kinase 1 | NM_005030 | CCAAGGUUUUCGAUUGCUC | 40 |
| | | | GAAUUGUACAGAAUAUUUC | 41 |
| | | | UCGUAGGAUUCCACGGCUU | 42 |
| rPPIB | cyclophilin B | NM_022536 | CCUUUGGACUCUUUGGAAA | 43 |
| | | | GCAAGUUCCAUCGUGUCAU | 44 |
| | | | UCAUUGUAGACUGUGGCAA | 45 |
| rGAPDH | glyceraldehyde-3-phosphate dehydrogenase | NM_017008 | UCUACAUGUUCCAGUAUGA | 46 |
| | | | CCAAUGUAUCCGUUGUGGA | 47 |
| | | | CUGCCAAGUAUGAUGACAU | 48 |
| mGAPDH | glyceraldehyde-3-phosphate dehydrogenase | NM_008084 | CCUGGUAUGACAAUGAAUA | 49 |
| | | | UCGUGGAGUCUACUGGUGU | 50 |
| | | | GUGUGAACCACGAGAAAUA | 51 |

TABLE IV-continued

Sense strand sequences for three separate siRNAs used in Example 66.

| Target Symbol | Gene Name | Accession No. | Sense Sequence 5'→3' | SEQ ID NO: |
|---|---|---|---|---|
| mPPIB | cyclophilin B | NM_011149 | CCGUCGUCUUCCUUUUGCU | 52 |
|  |  |  | GAAAGAGCAUCUAUGGUGA | 53 |
|  |  |  | GGUAUACUUUGAUUUACAA | 54 |

Figure 22:
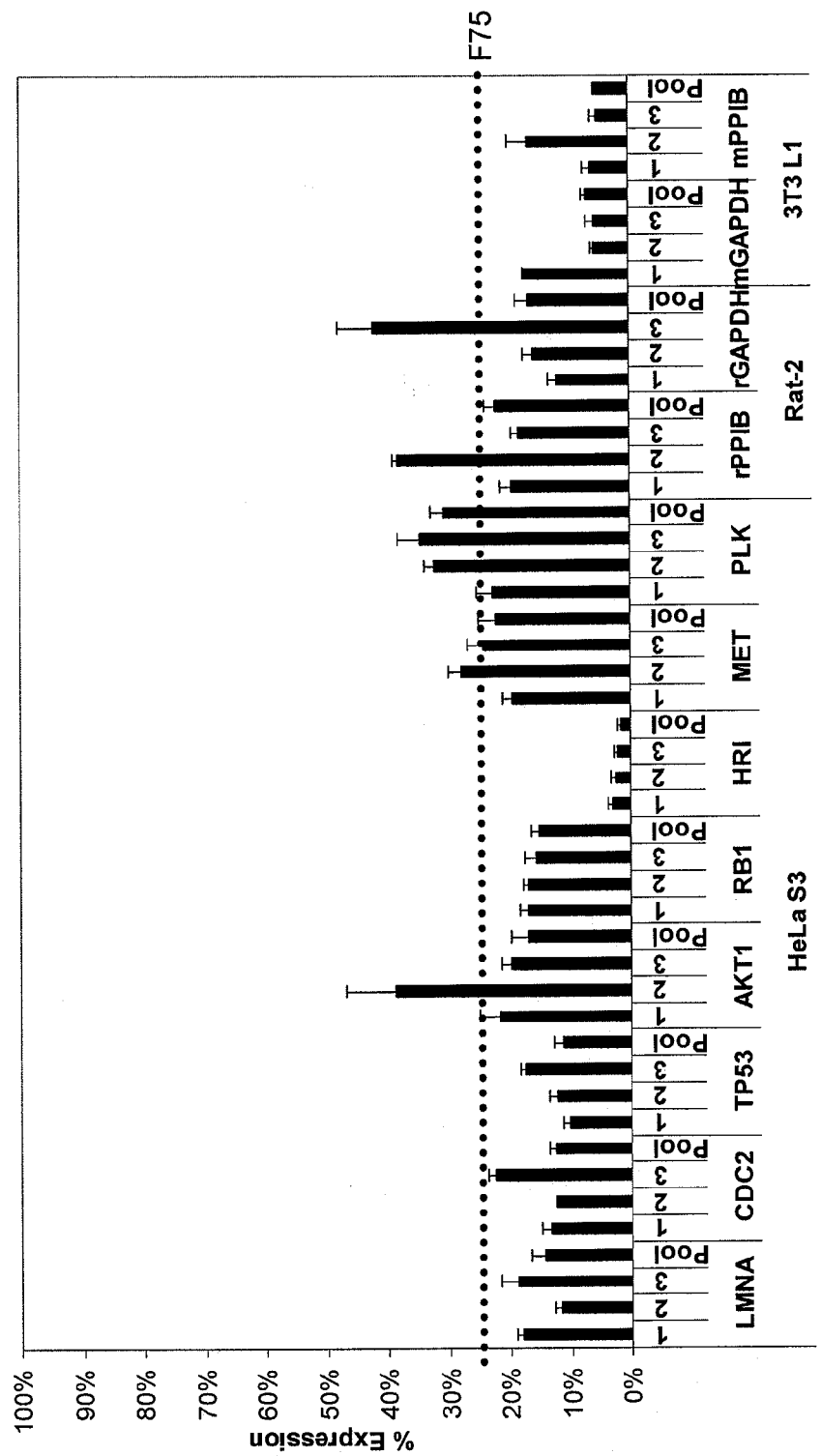
FIG. 22 depicts knockdown of a range of human and mouse genes by G4 siRNA. Specifically.

Results shown in FIG. 22 show that of the 36 individual duplexes tested, 30 provided 75% gene silencing or greater. Furthermore when these sequences were pooled, eleven out of twelve pools silenced gene expression by 75% or more. Similar results can be obtained irrespective of the presence of antibiotics (e.g. ampicillin). These findings demonstrate the G4 siRNA can be applied to a wide range of genes from multiple species, and is compatible with a pooling strategy.

We claim:

1. A method for inhibiting expression of a target gene in a cell, the method comprising delivering to said cell a duplex oligonucleotide complex comprising:

a. a sense strand that is nineteen nucleotides in length, wherein nucleotides 1 and 2 and all C and all U nucleotides on said sense strand are 2'O-methyl modified and the sense strand has a 3' end;

b. an antisense strand that is twenty-one nucleotides in length, wherein i. all C nucleotides and all U nucleotides on said antisense strand are 2'F modified;

ii. the antisense strand has a 5' end and a 3' end and one mismatched nucleotide with the sense strand at position 14 within the antisense strand and the opposite nucleotide 6 on the sense strand, wherein all other nucleotides within the sense strand are complementary to nucleotides on the antisense strand; and iii. the sense strand and the antisense strand form a duplex having a two nucleotide overhang at the 3'end of the antisense strand;

c. a cholesterol molecule attached to the 3' end of the sense strand via a C5 linker molecule, wherein the cholesterol-linker-sense strand has the structure:

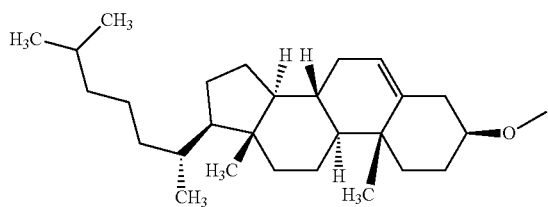

-continued

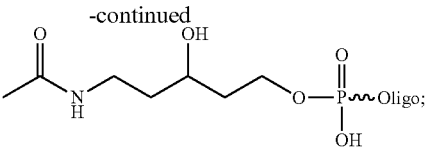

and d. a phosphate group at the 5' end of the antisense strand, wherein following said delivering the expression of a target protein is decreased.

2. The method of claim 1, wherein the delivering is passive.

3. The method of claim 1, wherein the two nucleotide overhang comprises a phosphorothioate linkage.

4. The method of claim 1, wherein the two nucleotide overhang comprises a UU sequence.

5. A method for inhibiting expression of a target gene in a cell, the method comprising delivering to said cell a duplex oligonucleotide complex comprising:

a. a sense strand that is nineteen nucleotides in length, wherein nucleotides 1 and 2 and all C and all U nucleotides on said sense strand are 2'O-methyl modified and the sense strand has a 3' end;

b. an antisense strand that is twenty-one nucleotides in length, wherein i. all C nucleotides and all U nucleotides on said antisense strand are 2'F modified;

ii. the antisense strand has a 5' end and a 3' end and one mismatched nucleotide with the sense strand at position 13 within the antisense strand and the opposite nucleotide 7 on the sense strand, wherein all other nucleotides within the sense strand are complementary to nucleotides on the antisense strand; and iii. the sense strand and the antisense strand form a duplex having a two nucleotide overhang at the 3' end of the antisense strand;

c. a cholesterol molecule attached to the 3' end of the sense strand via a C5 linker molecule, wherein the cholesterol-linker-sense strand has the structure:

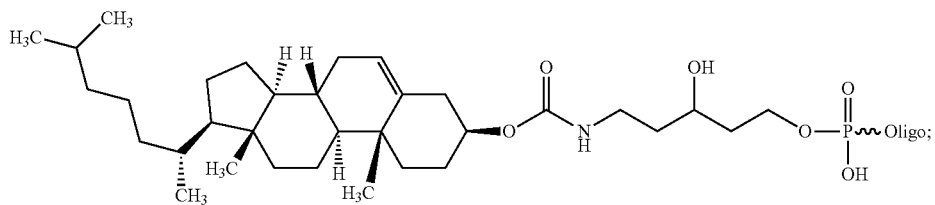

and
  d. a phosphate group at the 5' end of the antisense strand, wherein following said delivering the expression of a target protein is decreased.

6. The method of claim 5, wherein the delivering is passive.

7. The method of claim 5, wherein the two nucleotide overhang comprises a phosphorothioate linkage.

8. The method of claim 5, wherein the two nucleotide overhang comprises a UU sequence.

9. The method according to claim 1, wherein the opposite nucleotide 6 on the sense strand is the same nucleotide that occurs at position 14 of the antisense strand.

10. The method according to claim 5, wherein the opposite nucleotide 7 on the sense strand is the same nucleotide that occurs at position 13 of the antisense strand.

11. The method according to claim 1, wherein all nucleotides in the sense strand and in the antisense strand other than nucleotides 1 and 2 of the sense strand and all C nucleotides and all U nucleotides of the sense and antisense strands comprise a 2'-OH.

12. The method according to claim 5, wherein all nucleotides in the sense strand and in the antisense strand other than nucleotides 1 and 2 of the sense strand and all C nucleotides and all U nucleotides of the sense and antisense strands comprise a 2'-OH.

13. The method according to claim 1, wherein between about 40% and about 90% of the nucleotides of the sense strand and between about 40% and about 90% of the nucleotides of the antisense strand are chemically modified.

14. The method according to claim 5, wherein between about 40% and about 90% of the nucleotides of the sense strand and between about 40% and about 90% of the nucleotides of the antisense strand are chemically modified.

15. The method of claim 1, wherein said delivering to said cell is by reverse transfection.

16. The method of claim 5, wherein said delivering to said cell is by reverse transfection.

17. The method of claim 1, wherein said delivering to said cell is in vivo.

18. The method of claim 5, wherein said delivering to said cell is in vivo.

* * * * *

SEQUENCE LISTING

```
<160> NUMBER OF SEQ ID NOS: 54

<210> SEQ ID NO 1
<211> LENGTH: 19
<212> TYPE: RNA
<213> ORGANISM: Artificial sequence
<220> FEATURE:
<223> OTHER INFORMATION: oligo

<400> SEQUENCE: 1
acagcaaauu ccaucgugu                                              19

<210> SEQ ID NO 2
<211> LENGTH: 19
<212> TYPE: RNA
<213> ORGANISM: Artificial sequence
<220> FEATURE:
<223> OTHER INFORMATION: oligo

<400> SEQUENCE: 2
cacucaagau ugucagcaa                                              19

<210> SEQ ID NO 3
<211> LENGTH: 19
<212> TYPE: RNA
<213> ORGANISM: Artificial sequence
<220> FEATURE:
<223> OTHER INFORMATION: oligo

<400> SEQUENCE: 3
cacucaagau ugucagcaa                                              19

<210> SEQ ID NO 4
<211> LENGTH: 19
<212> TYPE: RNA
<213> ORGANISM: Artificial sequence
<220> FEATURE:
<223> OTHER INFORMATION: oligo

<400> SEQUENCE: 4
gcuucgagau guuccgaga                                              19

<210> SEQ ID NO 5
<211> LENGTH: 19
<212> TYPE: RNA
<213> ORGANISM: Artificial sequence
<220> FEATURE:
<223> OTHER INFORMATION: oligo

<400> SEQUENCE: 5
```
acagcaaauu ccaucgugu                                                19

<210> SEQ ID NO 6
<211> LENGTH: 19
<212> TYPE: RNA
<213> ORGANISM: Artificial sequence
<220> FEATURE:
<223> OTHER INFORMATION: oligo

<400> SEQUENCE: 6
gaugguggga auucgggaa                                                19

<210> SEQ ID NO 7
<211> LENGTH: 19
<212> TYPE: RNA
<213> ORGANISM: Artificial sequence
<220> FEATURE:
<223> OTHER INFORMATION: oligo

<400> SEQUENCE: 7
uguuggacuu cacgggcaa                                                19

<210> SEQ ID NO 8
<211> LENGTH: 19
<212> TYPE: RNA
<213> ORGANISM: Artificial sequence
<220> FEATURE:
<223> OTHER INFORMATION: oligo

<400> SEQUENCE: 8
ggauaugaga gacuggauu                                                19

<210> SEQ ID NO 9
<211> LENGTH: 19
<212> TYPE: RNA
<213> ORGANISM: Artificial sequence
<220> FEATURE:
<223> OTHER INFORMATION: oligo

<400> SEQUENCE: 9 ccaucggcu cuaacagau                                                 19

<210> SEQ ID NO 10
<211> LENGTH: 29
<212> TYPE: RNA
<213> ORGANISM: Artificial sequence
<220> FEATURE:
<223> OTHER INFORMATION: oligo

<400> SEQUENCE: 10
uggaaugagc ugaaagggac uuccaagga                                     29

<210> SEQ ID NO 11
<211> LENGTH: 19
<212> TYPE: RNA
<213> ORGANISM: Artificial sequence
<220> FEATURE:
<223> OTHER INFORMATION: oligo

<400> SEQUENCE: 11
gaugguggga auucgggaa                                                19

<210> SEQ ID NO 12
<211> LENGTH: 19
<212> TYPE: RNA
<213> ORGANISM: Artificial sequence

```
<220> FEATURE:
<223> OTHER INFORMATION: oligo

<400> SEQUENCE: 12
acagcaaauu ccaucgugu                                               19

<210> SEQ ID NO 13
<211> LENGTH: 19
<212> TYPE: RNA
<213> ORGANISM: Artificial sequence
<220> FEATURE:
<223> OTHER INFORMATION: oligo

<400> SEQUENCE: 13
uaaggcuaug aagagauac                                               19

<210> SEQ ID NO 14
<211> LENGTH: 19
<212> TYPE: RNA
<213> ORGANISM: Artificial sequence
<220> FEATURE:
<223> OTHER INFORMATION: oligo

<400> SEQUENCE: 14
ucacgacagu caagacagc                                               19

<210> SEQ ID NO 15
<211> LENGTH: 19
<212> TYPE: RNA
<213> ORGANISM: Artificial sequence
<220> FEATURE:
<223> OTHER INFORMATION: oligo

<400> SEQUENCE: 15
cagcaaauuc caucgugua                                               19

<210> SEQ ID NO 16
<211> LENGTH: 19
<212> TYPE: RNA
<213> ORGANISM: Artificial sequence
<220> FEATURE:
<223> OTHER INFORMATION: oligo

<400> SEQUENCE: 16
uaaggcuaug aagagauac                                               19

<210> SEQ ID NO 17
<211> LENGTH: 19
<212> TYPE: RNA
<213> ORGANISM: Artificial sequence
<220> FEATURE:
<223> OTHER INFORMATION: oligo

<400> SEQUENCE: 17
gacaugaauu ccuuaauga                                               19

<210> SEQ ID NO 18
<211> LENGTH: 19
<212> TYPE: RNA
<213> ORGANISM: Artificial sequence
<220> FEATURE:
<223> OTHER INFORMATION: oligo

<400> SEQUENCE: 18
gucaucacac ugaauacca                                               19
```

```
<210> SEQ ID NO 19
<211> LENGTH: 19
<212> TYPE: RNA
<213> ORGANISM: Artificial sequence
<220> FEATURE:
<223> OTHER INFORMATION: oligo

<400> SEQUENCE: 19
gcaacaaguc caaugagga                                                    19

<210> SEQ ID NO 20
<211> LENGTH: 19
<212> TYPE: RNA
<213> ORGANISM: Artificial sequence
<220> FEATURE:
<223> OTHER INFORMATION: oligo

<400> SEQUENCE: 20
ucaccgaguc ugaagaggu                                                    19

<210> SEQ ID NO 21
<211> LENGTH: 19
<212> TYPE: RNA
<213> ORGANISM: Artificial sequence
<220> FEATURE:
<223> OTHER INFORMATION: oligo

<400> SEQUENCE: 21
gugaggaguu uaaggagcu                                                    19

<210> SEQ ID NO 22
<211> LENGTH: 19
<212> TYPE: RNA
<213> ORGANISM: Artificial sequence
<220> FEATURE:
<223> OTHER INFORMATION: oligo

<400> SEQUENCE: 22
ccauggaucu gaagaaaua                                                    19

<210> SEQ ID NO 23
<211> LENGTH: 19
<212> TYPE: RNA
<213> ORGANISM: Artificial sequence
<220> FEATURE:
<223> OTHER INFORMATION: oligo

<400> SEQUENCE: 23
uccuaguacu gcaauucgg                                                    19

<210> SEQ ID NO 24
<211> LENGTH: 19
<212> TYPE: RNA
<213> ORGANISM: Artificial sequence
<220> FEATURE:
<223> OTHER INFORMATION: oligo

<400> SEQUENCE: 24
gaguugugua uaaggguag                                                    19

<210> SEQ ID NO 25
<211> LENGTH: 19
<212> TYPE: RNA
<213> ORGANISM: Artificial sequence
<220> FEATURE:
<223> OTHER INFORMATION: oligo

<400> SEQUENCE: 25
```
ugcucagggu caauuucuu                                          19

<210> SEQ ID NO 26
<211> LENGTH: 19
<212> TYPE: RNA
<213> ORGANISM: Artificial sequence
<220> FEATURE:
<223> OTHER INFORMATION: oligo

<400> SEQUENCE: 26
cucuuguaua ugaugaucu                                          19

<210> SEQ ID NO 27
<211> LENGTH: 19
<212> TYPE: RNA
<213> ORGANISM: Artificial sequence
<220> FEATURE:
<223> OTHER INFORMATION: oligo

<400> SEQUENCE: 27
cccucacugu ugaauuuc                                           19

<210> SEQ ID NO 28
<211> LENGTH: 19
<212> TYPE: RNA
<213> ORGANISM: Artificial sequence
<220> FEATURE:
<223> OTHER INFORMATION: oligo

<400> SEQUENCE: 28
gugccaugau cuguauuua                                          19

<210> SEQ ID NO 29
<211> LENGTH: 19
<212> TYPE: RNA
<213> ORGANISM: Artificial sequence
<220> FEATURE:
<223> OTHER INFORMATION: oligo

<400> SEQUENCE: 29 guauuugau gaggaguuc                                           19

<210> SEQ ID NO 30
<211> LENGTH: 19
<212> TYPE: RNA
<213> ORGANISM: Artificial sequence
<220> FEATURE:
<223> OTHER INFORMATION: oligo

<400> SEQUENCE: 30
gguuuaaauu uguuauugu                                          19

<210> SEQ ID NO 31
<211> LENGTH: 19
<212> TYPE: RNA
<213> ORGANISM: Artificial sequence
<220> FEATURE:
<223> OTHER INFORMATION: oligo

<400> SEQUENCE: 31
gcuuugauau ugaaggauc                                          19

<210> SEQ ID NO 32
<211> LENGTH: 19
<212> TYPE: RNA
<213> ORGANISM: Artificial sequence

```
<220> FEATURE:
<223> OTHER INFORMATION: oligo

<400> SEQUENCE: 32
ucgucaggcu ugaguuuga                                              19

<210> SEQ ID NO 33
<211> LENGTH: 19
<212> TYPE: RNA
<213> ORGANISM: Artificial sequence
<220> FEATURE:
<223> OTHER INFORMATION: oligo

<400> SEQUENCE: 33
cuuguaacau cuaauggac                                              19

<210> SEQ ID NO 34
<211> LENGTH: 19
<212> TYPE: RNA
<213> ORGANISM: Artificial sequence
<220> FEATURE:
<223> OTHER INFORMATION: oligo

<400> SEQUENCE: 34
ccaaaauucu ggaaauguu                                              19

<210> SEQ ID NO 35
<211> LENGTH: 19
<212> TYPE: RNA
<213> ORGANISM: Artificial sequence
<220> FEATURE:
<223> OTHER INFORMATION: oligo

<400> SEQUENCE: 35
guaguuaacu ggaauguaa                                              19

<210> SEQ ID NO 36
<211> LENGTH: 19
<212> TYPE: RNA
<213> ORGANISM: Artificial sequence
<220> FEATURE:
<223> OTHER INFORMATION: oligo

<400> SEQUENCE: 36
guaugauuuu gcugaauuu                                              19

<210> SEQ ID NO 37
<211> LENGTH: 19
<212> TYPE: RNA
<213> ORGANISM: Artificial sequence
<220> FEATURE:
<223> OTHER INFORMATION: oligo

<400> SEQUENCE: 37
ccugcaaucu acaagguuu                                              19

<210> SEQ ID NO 38
<211> LENGTH: 19
<212> TYPE: RNA
<213> ORGANISM: Artificial sequence
<220> FEATURE:
<223> OTHER INFORMATION: oligo

<400> SEQUENCE: 38
cuguugucau cagaagaua                                              19
```

```
<210> SEQ ID NO 39
<211> LENGTH: 19
<212> TYPE: RNA
<213> ORGANISM: Artificial sequence
<220> FEATURE:
<223> OTHER INFORMATION: oligo

<400> SEQUENCE: 39
gcaugaagca ggaaggaac                                              19

<210> SEQ ID NO 40
<211> LENGTH: 19
<212> TYPE: RNA
<213> ORGANISM: Artificial sequence
<220> FEATURE:
<223> OTHER INFORMATION: oligo

<400> SEQUENCE: 40
ccaagguuuu cgauugcuc                                              19

<210> SEQ ID NO 41
<211> LENGTH: 19
<212> TYPE: RNA
<213> ORGANISM: Artificial sequence
<220> FEATURE:
<223> OTHER INFORMATION: oligo

<400> SEQUENCE: 41
gaauuguaca gaauauuuc                                              19

<210> SEQ ID NO 42
<211> LENGTH: 19
<212> TYPE: RNA
<213> ORGANISM: Artificial sequence
<220> FEATURE:
<223> OTHER INFORMATION: oligo

<400> SEQUENCE: 42
ucguaggauu ccacggcuu                                              19

<210> SEQ ID NO 43
<211> LENGTH: 19
<212> TYPE: RNA
<213> ORGANISM: Artificial sequence
<220> FEATURE:
<223> OTHER INFORMATION: oligo

<400> SEQUENCE: 43
ccuuuggacu cuuuggaaa                                              19

<210> SEQ ID NO 44
<211> LENGTH: 19
<212> TYPE: RNA
<213> ORGANISM: Artificial sequence
<220> FEATURE:
<223> OTHER INFORMATION: oligo

<400> SEQUENCE: 44
gcaaguucca ucgugucau                                              19

<210> SEQ ID NO 45
<211> LENGTH: 19
<212> TYPE: RNA
<213> ORGANISM: Artificial sequence
<220> FEATURE:
<223> OTHER INFORMATION: oligo

<400> SEQUENCE: 45
```
ucauuguaga cuguggcaa                                                19

<210> SEQ ID NO 46
<211> LENGTH: 19
<212> TYPE: RNA
<213> ORGANISM: Artificial sequence
<220> FEATURE:
<223> OTHER INFORMATION: oligo

<400> SEQUENCE: 46
ucuacauguu ccaguauga                                                19

<210> SEQ ID NO 47
<211> LENGTH: 19
<212> TYPE: RNA
<213> ORGANISM: Artificial sequence
<220> FEATURE:
<223> OTHER INFORMATION: oligo

<400> SEQUENCE: 47
ccaauguauc cguugugga                                                19

<210> SEQ ID NO 48
<211> LENGTH: 19
<212> TYPE: RNA
<213> ORGANISM: Artificial sequence
<220> FEATURE:
<223> OTHER INFORMATION: oligo

<400> SEQUENCE: 48
cugccaagua ugaugacau                                                19

<210> SEQ ID NO 49
<211> LENGTH: 19
<212> TYPE: RNA
<213> ORGANISM: Artificial sequence
<220> FEATURE:
<223> OTHER INFORMATION: oligo

<400> SEQUENCE: 49
ccugguauga caaugaaua                                                19

<210> SEQ ID NO 50
<211> LENGTH: 19
<212> TYPE: RNA
<213> ORGANISM: Artificial sequence
<220> FEATURE:
<223> OTHER INFORMATION: oligo

<400> SEQUENCE: 50
ucguggaguc uacuggugu                                                19

<210> SEQ ID NO 51
<211> LENGTH: 19
<212> TYPE: RNA
<213> ORGANISM: Artificial sequence
<220> FEATURE:
<223> OTHER INFORMATION: oligo

<400> SEQUENCE: 51
gugugaacca cgagaaaua                                                19

<210> SEQ ID NO 52
<211> LENGTH: 19
<212> TYPE: RNA
<213> ORGANISM: Artificial sequence

```
<220> FEATURE:
<223> OTHER INFORMATION: oligo

<400> SEQUENCE: 52
ccgucgucuu ccuuuugcu                                                 19

<210> SEQ ID NO 53
<211> LENGTH: 19
<212> TYPE: RNA
<213> ORGANISM: Artificial sequence
<220> FEATURE:
<223> OTHER INFORMATION: oligo

<400> SEQUENCE: 53
gaaagagcau cuaugguga                                                 19

<210> SEQ ID NO 54
<211> LENGTH: 19
<212> TYPE: RNA
<213> ORGANISM: Artificial sequence
<220> FEATURE:
<223> OTHER INFORMATION: oligo

<400> SEQUENCE: 54
gguauacuuu gauuuacaa                                                 19
```